US011659350B1

(12) United States Patent
Tran

(10) Patent No.: US 11,659,350 B1
(45) Date of Patent: May 23, 2023

(54) METAVERSE DATING

(71) Applicant: Bao Tran, Saratoga, CA (US)

(72) Inventor: Bao Tran, Saratoga, CA (US)

( * ) Notice: Subject to any disclaimer, the term of this patent is extended or adjusted under 35 U.S.C. 154(b) by 0 days.

(21) Appl. No.: 17/700,545

(22) Filed: Mar. 22, 2022

Related U.S. Application Data

(63) Continuation of application No. 17/023,079, filed on Sep. 16, 2020, now Pat. No. 11,304,023, which is a continuation of application No. 15/414,186, filed on Jan. 24, 2017, now Pat. No. 10,841,724.

(51) Int. Cl.
| | | |
|---|---|---|
| *H04S 7/00* | (2006.01) | |
| *A61F 11/04* | (2006.01) | |
| *H04S 1/00* | (2006.01) | |
| *G06F 3/01* | (2006.01) | |
| *H04R 1/40* | (2006.01) | |
| *G10L 15/26* | (2006.01) | |
| *H04R 5/027* | (2006.01) | |
| *H04R 3/00* | (2006.01) | |
| *G06T 19/00* | (2011.01) | |

(52) U.S. Cl.
CPC .............. *H04S 7/304* (2013.01); *A61F 11/04* (2013.01); *G06F 3/013* (2013.01); *G06F 3/017* (2013.01); *G10L 15/26* (2013.01); *H04R 1/406* (2013.01); *H04R 3/00* (2013.01); *H04R 5/027* (2013.01); *H04S 1/007* (2013.01); *G06T 19/006* (2013.01)

(58) Field of Classification Search
CPC . H04R 1/08; H04R 1/40; H04R 1/406; H04R 3/00; H04R 3/005; H04R 3/04; H04R 5/027; H04R 2201/401; H04R 2201/403; G06F 3/013; G06F 3/17; A61F 11/04; H04S 7/304; H04S 1/007; G06T 19/006
USPC ..................... 381/91, 92, 122, 315, 111–115
See application file for complete search history.

(56) References Cited

U.S. PATENT DOCUMENTS

| | | | | |
|---|---|---|---|---|
| 8,510,166 | B2 * | 8/2013 | Neven ................ | G06Q 30/0242 |
| | | | | 705/14.69 |
| 9,423,872 | B2 * | 8/2016 | Kim ........................ | G06T 11/00 |
| 9,600,743 | B2 * | 3/2017 | Anderson ............... | G06F 3/048 |
| 10,051,402 | B1 * | 8/2018 | Lyren ...................... | H04S 7/304 |
| 10,528,614 | B2 * | 1/2020 | Kochura ................. | G06F 16/51 |
| 10,841,724 | B1 * | 11/2020 | Tran ........................ | G06F 3/011 |
| 11,304,023 | B1 * | 4/2022 | Tran ........................ | G10L 15/26 |
| 2003/0107649 | A1 * | 6/2003 | Flickner ............... | G06V 10/758 |
| | | | | 348/169 |
| 2010/0228633 | A1 * | 9/2010 | Guimaraes ......... | G06Q 30/0273 |
| | | | | 705/14.69 |
| 2019/0332804 | A1 * | 10/2019 | Qi ......................... | H04L 63/101 |
| 2020/0387341 | A1 * | 12/2020 | Robinson ............... | H04R 25/70 |
| 2021/0051129 | A1 * | 2/2021 | Zhang .................... | H04W 4/21 |

* cited by examiner

*Primary Examiner* — Xu Mei

(74) *Attorney, Agent, or Firm* — PowerPatent Patent PC

(57) ABSTRACT

A metaverse dating system is disclosed with a first camera to capture an image of a dating prospect and a second camera to capture eye gazing; a processor coupled to the second camera to determine interest in the dating prospect, the processor coupled to the first camera to analyze prospect information including appearance and body shape therefrom, the processor comparing the interest and prospect information with prior likings; and a projector aimed at a retina, the projector providing information and recommendations on approaching the dating prospect.

20 Claims, 20 Drawing Sheets

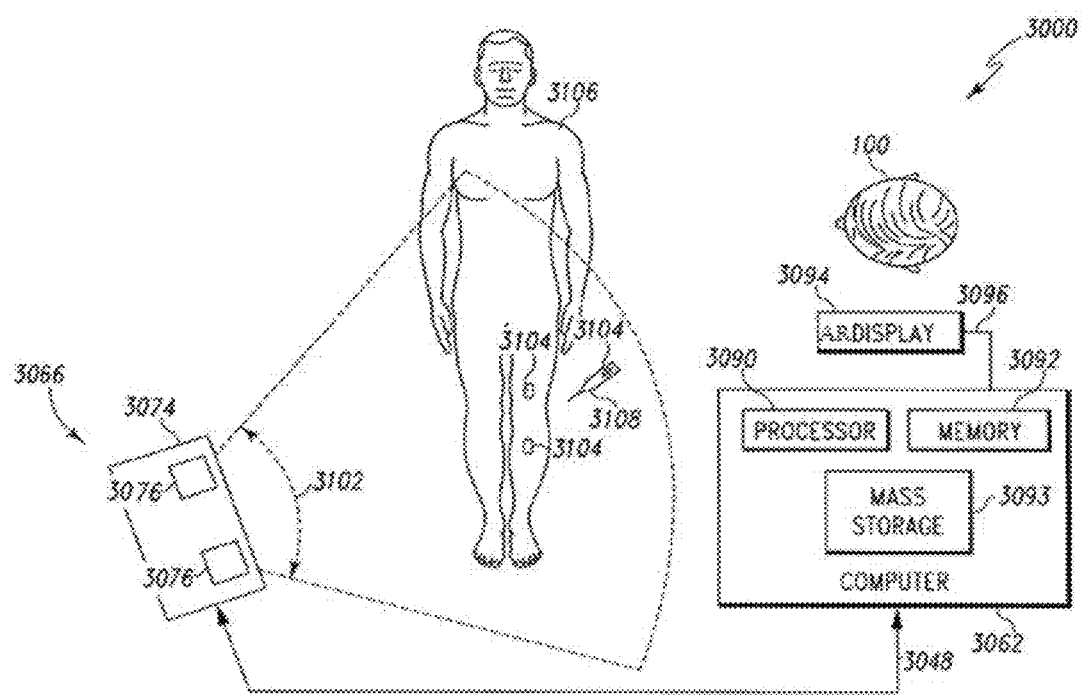
FIG. 18A
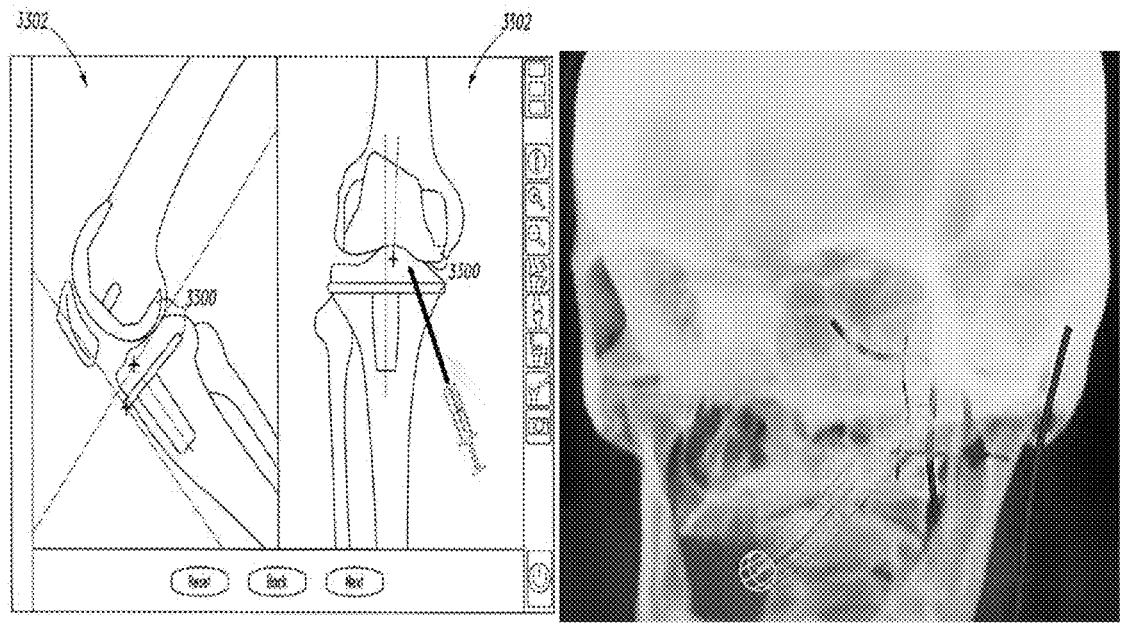
FIG. 18B
FIG. 18C

US 11,659,350 B1

METAVERSE DATING

BACKGROUND

Hearing enhancement is needed in various situations including surveillance, hearing aid, or part of a virtual reality or augmented reality system. Present hearing enhancement systems include a headphone, headset, or a hearing aid.

SUMMARY OF THE INVENTION

In one aspect, a hearing system includes an eye tracking module to detect a sound region of interest; one or more microphone arrays coupled to the eye tracking module and focused on the detected sound region of interest; and one or more amplifiers wirelessly coupled to the one or more microphone arrays and to render sound from the sound region of interest for one or more ears.

The system can be used for hearing assistance, surveillance, or virtual/augmented reality applications to enhance audio communications with computers or humans.

BRIEF DESCRIPTION OF THE DRAWINGS

FIG. 18A shows an exemplary AR surgical system, while FIG. 18B shows an exemplary template superimposed on bones and tissues using the AR display of FIG. 1.

FIG. 18C shows an exemplary AR view of a placement of a neuromodulator to mask pain.

DETAILED DESCRIPTION

Arrangements and embodiments may now be described more fully with reference to the accompanying drawings, in which exemplary embodiments may be shown. Embodiments may, however, be embodied in many different forms and should not be construed as being limited to embodiments set forth herein; rather, embodiments may be provided so that this disclosure will be thorough and complete, and will fully convey the concept to those skilled in the art.

The suffixes 'module', 'unit' and 'part' may be used for elements in order to facilitate the disclosure. Significant meanings or roles may not be given to the suffixes themselves and it is understood that the 'module', 'unit' and 'part' may be used together or interchangeably.

Figure 1:
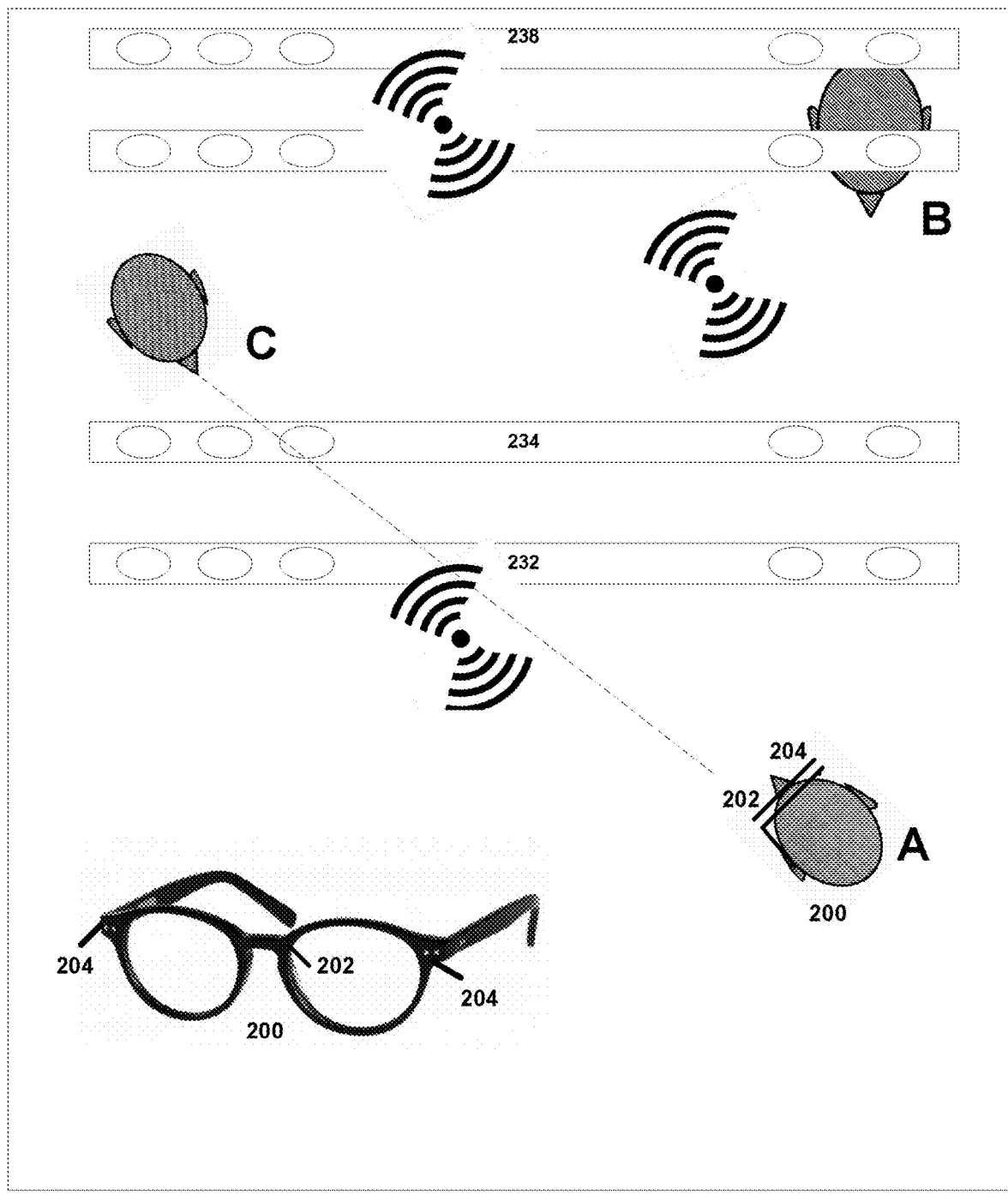
FIG. 1 shows an exemplary audio system.

FIG. 1 shows an exemplary hearing system 200 that includes an eye tracking module 202 to detect user interest in a sound region of interest. For example, the user can be looking at a person C that the user is talking to, and the eye tracking module 202 determines a direction that is used to control a microphone array 204 to focus the array and enhance sound from that particular person C while deemphasizing sound from others such as person B in FIG. 1. Moreover, background noise not in the proximity of speaker C is removed. One or more amplifiers 206 is then adapted to render sound from the sound region of interest for one or more ears. In addition to the body mounted microphone array, a plurality of remote microphones is positioned around a room. In FIG. 1, various microphone arrays 232-238 capture sound in local regions in the room, each of arrays 232-238 have a plurality of microphones (denoted as circles), and the microphones can be remotely controlled to focus on a particular section of the room.

The microphone array can be a 360 degree microphone array. The eye tracking module can be one or more cameras to detect eye movement or eye gaze. An emotion detection module can be connected to the eye tracking module and can provide sound in response to the detected emotion.

In addition, the remote microphone arrays 232-238 can include a wireless communication module (WiFi or Bluetooth or Zigbee) to connect the remote microphones to the left and right amplifiers so that sounds picked up remotely can be heard by the hearing device. A beam forming module can be used to capture sound from the microphone array and the remote microphones and deliver enhanced sound from the region of interest to the left and right ears. With such selective sound pickup, the hearing device can command the remote microphones to selectively pickup sound in the direction of the eye focus. For example, if the eye is focused on a remote TV screen, the microphone arrays (local and remote) pickup sound from the TV for the user. Then if the user focuses on a conversational group beyond the TV, the microphone array nearest that group of people focuses on the conversation.

Further, a wireless communication (Bluetooth) module can provide wireless communication between the amplifiers and a smart phone. The smart phone can be used to tune or adjust each amplifier performance or audio response. A speech recognizer to transcribe verbal communications delivered to the one or more ears. A display can display the text recognized by the speech recognizer. The eye tracking unit can be an eye glass with one or more cameras to capture eye movement, wherein the microphone array is mounted on the eye glass. The eye tracking unit can be jewelry with one or more cameras to capture eye movement, wherein the microphone array is mounted on the eye glass. One or more remote cameras such as a laptop or mobile device can capture eye movements. A contact lens or eye wearable device can be used to capture eye movement. An accelerometer can be used to detect head rotation. A camera can be used with a facial recognition module. A noise canceller can be connected to the microphone array.

Figure 2A:
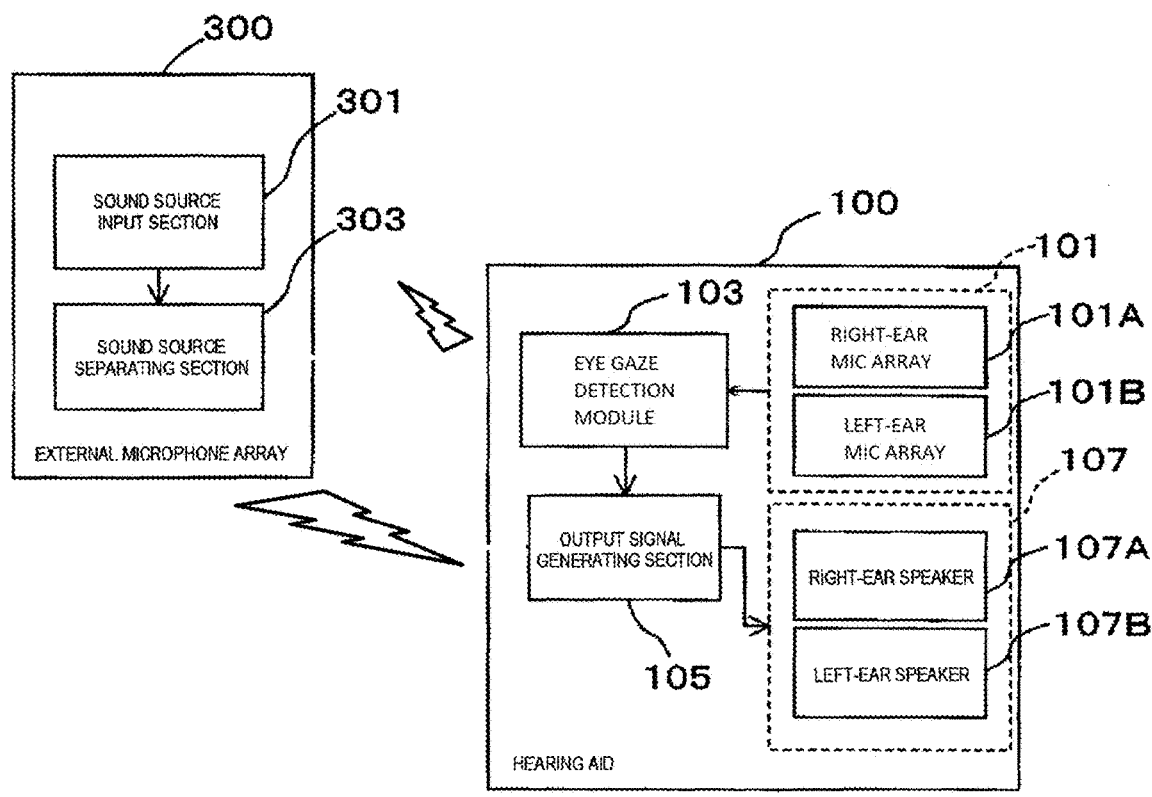
FIG. 2A is a block diagram showing the configuration of a hearing system.

In one embodiment shown in FIG. 2A, a hearing aid 100 and an external microphone array 300 are shown. A plurality of microphone arrays (FIG. 1's 232-238) can be used, with the indoor position of the array of of microphones known in advance and the position can be used in noise cancellation and focusing of the sound capture. The hearing aid 100 has a right unit which is worn on a right ear and a left unit which is worn on a left ear. The left and right units include microphones for respective ears of a binaural microphone array 101, an eye gaze detector 103, an output signal generating section 105, and speakers for respective ears of a binaural speaker 107. The left and right units of the hearing aid 100 perform wireless communication with each other. The left and right units of the hearing aid 100 may perform wireless communication with each other.

The binaural microphone 101 has a right-ear microphone 101A which constitutes a part of the right unit and a left-ear microphone 101B which constitutes a part of the left unit. The binaural microphone 101 receives sound from sound sources for a person who wears the hearing aid 100 as input to the left and right ears of the person who wears the hearing aid 100 and converts the input sound to acoustic signals.

The eye gaze detector 103 acquires a plurality of images of a user's eye and at least one image of at least part of the user's field of view. In one embodiment, images of the user's eye are taken using a high-speed RGB or IR camera capable of shooting, for example, 100 frames per second. The cameras taking the images of both the user's eye and the user's field of view may be integrated into an eye-glass or suitable wearable display. The detector 103 determines at least one gaze target area in the at least one image of at least part of the user's field of view based on at least one of the plurality of images of the user's eye. In one embodiment, gaze target component 304 determines a first estimated gaze based on at least one of the plurality of images of the user's eye. That is, by analyzing the geometry and orientation of the user's eye as captured in an image, gaze target component estimates a gaze line of where the user's eye is looking. In some embodiments, gaze target component considers a 3D model of the human eye and estimates the cornea center for the user's eye and pupil center for the user's eye. A gaze line is calculated that runs from the cornea center through the pupil center, adjusted for any calibration that has been performed. This gaze line is the first estimated gaze. Gaze target component then identifies at least one virtual or real visual target in the at least one image of at least part of the user's field of view corresponding to the first estimated gaze. The first estimated gaze is projected from the user's eye, and real or virtual objects in the user's field of view that are intersected by the first estimated gaze, are near the first estimated gaze, or are likely to viewing targets based on the first estimated gaze and detected acceleration or deceleration are then identified as gaze targets. For each virtual or real visual target, a gaze target area in the user's field of view is determined that encompasses at least part of the corresponding virtual or real visual target. The detector 103 segments a plurality of images of the user's eye into a plurality of features according to a segmentation model, the segmentation model including (1) the user's eye and (2) the region around the user's eye. In one embodiment, the region within approximately one and one-half inches of the eyelids when open is included. Various eye segmentation models exist, but none of these models currently provide a comprehensive segmentation that includes the eye itself and the surrounding areas. Segmenting the eye as well as the area around the eye allows for identification of a large number of features that can be matched against stored eye information in the event that particular eye features are occluded in any given image. Various features around the eye change in particular ways for particular movements, and a number of features may be useful for determining user eye gaze. A number of comprehensive segmentation models are contemplated.

In one embodiment, the eye gaze detector 103 calculates the directional sense components of the sound coming from the sound sources directly from the sound reaching the binaural microphone array 101 from the sound sources. For this reason, the hearing system can truly reproduce the direction of the sound coming from the sound sources. The directional sense component calculating section 103 may calculate one of interaural time differences and interaural volume difference as a directional sense component, and may calculate both the interaural time difference and the interaural volume difference as a directional sense component.

The output signal generating section 105 generates left and right acoustic signals, which will be output from the left and right speakers, from the directional sense components calculated by the directional sense component calculating section 103 and the sound source signals received from the external microphone array 300 described below. The output signal generating section 105 determines which of the left unit and the right unit is distant from the sound sources from the interaural time difference The binaural speaker 107 has a right-ear speaker 107A which constitutes a part of the right unit and a left-ear speaker 107B which constitutes a part of the left unit. The binaural speaker 107 outputs the left and right acoustic signals generated by the output signal generating section 105 on the left and right ears of the person who wears the hearing aid 100.

Next, the configuration of the external microphone array 300 which constitutes a part of the hearing system of Embodiment 1 will be described with reference to FIG. 1. The external microphone array 300 includes a sound source input section 301 and a sound source separating section 303. In the hearing system of Embodiment 1, the external microphone array 300 is provided at a closer location than the binaural microphone 101 of the hearing aid 100. The external microphone array 300 performs wireless communication with the left and right units of the hearing aid 100. The external microphone array 300 may perform wired communication with the left and right units of the hearing aid 100.

The sound source input section 301 receives the sound coming from the sound sources to the external microphone array 300 as input, and converts the input sound to acoustic signals. The sound source input section 301 has a plurality of microphones.

The acoustic signals of the respective microphones converted by the sound source input section 301 are transferred to the sound source separating section 303.

The sound source separating section 303 detects the directions of the sound sources with the external microphone array 300 as a base point using the difference in the incoming time of the sound coming from the sound sources to the microphones.

The sound source separating section 303 adds the acoustic signals of the microphones on the basis of the spatial arrangement of the microphones while taking into consideration the delay time of the sound for the microphones. Thus, the sound source separating section 303 generates the sound source signals subjected to directionality processing toward the sound sources with the external microphone array 300 as a base point, and transmits the sound source signals to the output signal generating section 105 of the hearing aid 100 in a wireless manner. With regard to the sound source signals generated by the sound source separating section 303, sound coming from a target sound source is highlighted (subjected to directionality processing) with the external microphone array 300 as a base point. For this reason, with regard to the sound source signals generated by the sound source separating section 303, sound other than the sound of the target sound source is suppressed, and the sound of the target sound source is clarified. When the location of the external microphone array 300 is closer to the location of the sound source than the location of the binaural microphone 101, with regard to the sound source signals generated by the sound source separating section 303, the sound of the target sound source is further clarified.

A user of the hearing system can clearly listen to the sound of the speaker while perceiving the incoming direction on the basis of the sound component having high clearness and the directional sense component.

Although in the above description, the respective sections are connected to each other by the wires L1 and L2, the respective sections may be connected to each other in a wireless manner. For example, a right-ear unit 110R which includes the right-ear microphone 101A and the right-ear speaker 107A, a left-ear unit 110L which includes the left-ear microphone 101B and the left-ear speaker 107B, and the external microphone array 300 may respectively include a power supply, a DSP, a communication section, a storage section, a control section, and the like, and may perform communication with each other in a wireless manner.

One embodiment can be similar to a hearing aid which is inserted in the ear canal as usual. In another embodiment, the hearing device can be an appliance worn by a user in his or her oral cavity. The appliance includes a power chamber that supplies energy to power the appliance. The power chamber includes an energy reservoir such as a battery. The battery is charged by charger electronic which can receive external energy through inductive coupling or can directly receive a charge through two terminals. If the charging is to be done inductively, a recharging coil is also enclosed in the power chamber. The power chamber provides energy for electronics in an actuation chamber. Mechanically, the chambers are connected by a bridge. Inside the bridge are cables that supply power to the actuation chamber. Other devices such as antenna wires can be embedded in the bridge. The chambers and the bridge are made from human compatible elastomeric materials commonly used in dental retainers, among others. In the actuation chamber, an actuator is positioned near the patient's teeth. The actuator is driven by an electronic driver 409A wireless transceiver provides sound information to the electronic driver so that the driver can actuate the actuator to cause sound to be generated and conducted to the patient's ear through bone conduction in one embodiment. For example, the electronic and actuator assembly may receive incoming sounds either directly or through a receiver to process and amplify the signals and transmit the processed sounds via a vibrating transducer element coupled to a tooth or other bone structure, such as the maxillary, mandibular, or palatine bone structure. Other sound transmission techniques in addition to bone conduction can be used and are contemplated by the inventors.

The hearing device may be a custom-made device fabricated through a variety of different process utilizing, e.g., a replicate model of a dental structure obtained by any number of methods, as described below in further detail. The oral appliance may accordingly be created to fit, adhere, or be otherwise disposed upon a portion of the patient's dentition to maintain the electronics and transducer device against the patient's dentition securely and comfortably.

The form of the hearing device 100 is not particularly limited. However, for example, if the hearing aid 100 is in a canal form, the hearing system can generate a directional sense component in which the direction of the head of the person who wears the binaural microphone 101 and an influence of reflection depending on the size or form of each region (pinna, shoulder, torso) of the person who wears the hearing aid 100 are reflected.

Figure 2B:
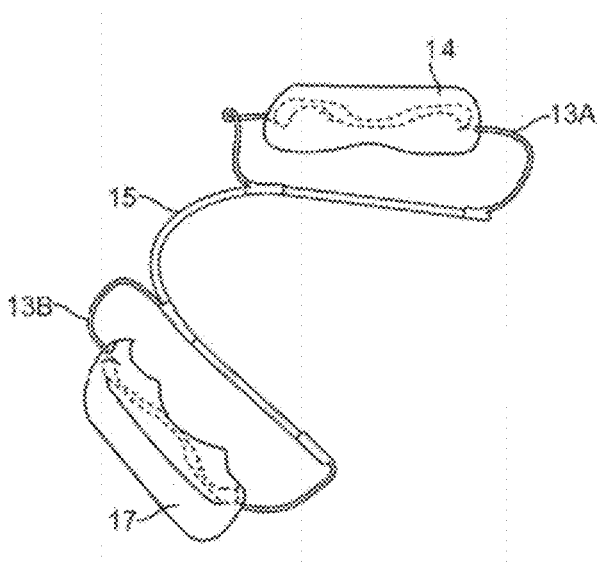
FIG. 2B shows an exemplary bone conduction hearing enhancement while avoidance the appearance of hearing aid.

FIG. 2B shows a second embodiment where the bridge as well as the mechanical supports for the chambers are made from metallic wire frames. As shown in FIG. 2A, chambers 14 and 17 are supported by wire frames 13A and 13B, respectively. The support wire frames 13A-13B are mechanically secured to a main wire frame 15. The cabling for electrical communication between chambers 14 and 17 can he made through wires running along the outside of the wireframes. The main wire frame 15 is hollow to allow wire cabling to run inside the main wire frame 15. In this embodiment, once the cabling exits the main wire frame 15, the wire assembly can be soldered or otherwise connected to electrical contacts on the chambers 14 or 17 as needed to connect circuits between chambers 14 and 17. In another embodiment, the power supply, transceiver, and actuator are housed in a single chamber mounted intra-orally to one or more teeth. An actuator is positioned adjacent the teeth. The actuator can include a mass and a piezoelectric transducer. The actuator is driven by an amplifier, which receives audio input from a transceiver in communication with the mic arrays on the glass, for example. The transceiver contains an antenna to capture wireless signals transmitted by a remote audio device.

Figure 3A:
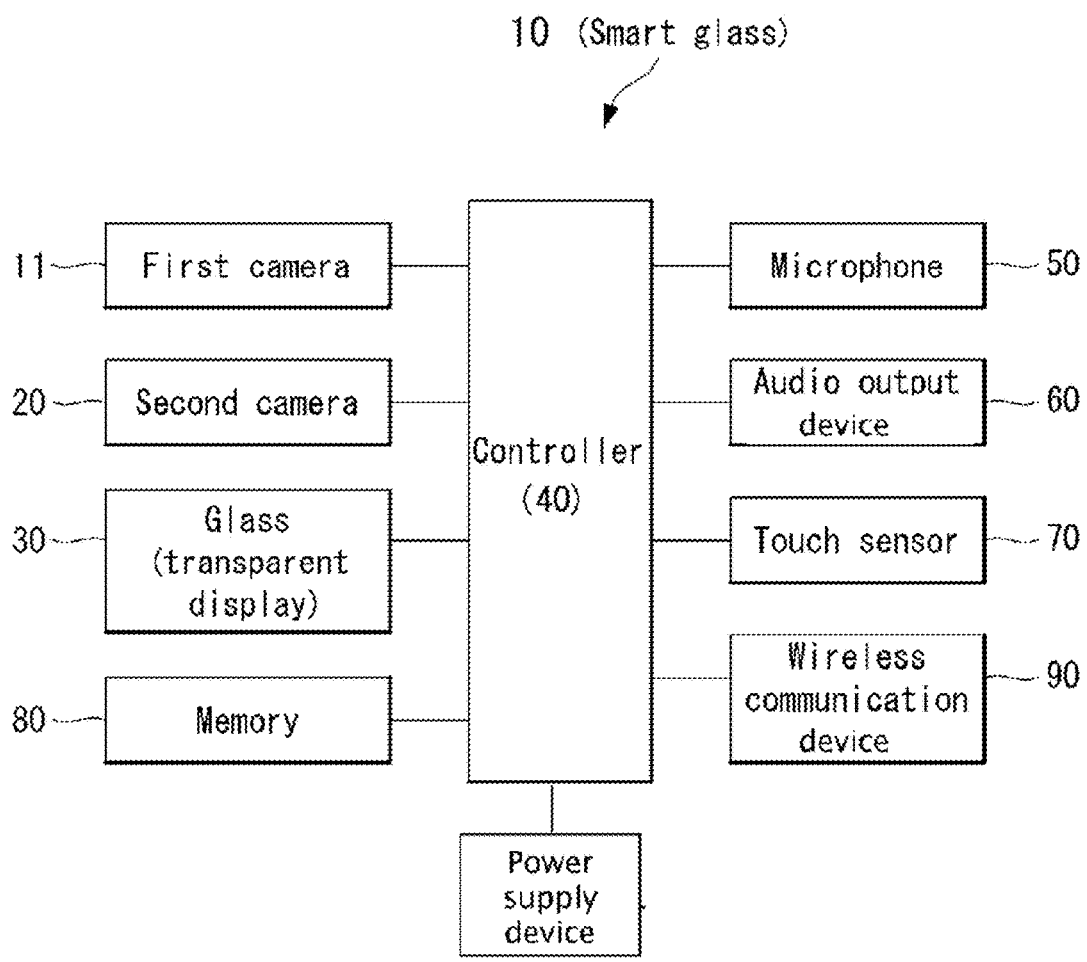
FIG. 3A is a block diagram showing an exemplary virtual or augmented reality system with hearing enhancement.

FIG. 3A shows an exemplary smart glass with hearing enhancement. FIG. 3A shows the smart glass 10 having various components, although other components may also be used. More or less components may alternatively be implemented. The smart glass 10 includes a first camera 11, a second camera 20, a glass 30, a controller 40, a microphone 50, an audio output device 60, a touch sensor 70, a memory 80, and a wireless communication device 90. The first camera 11 is used to take a front image of the smart glass 10 and may rotate up and down and side to side at a predetermined angle. The second camera 20 may be used to take an image of eyes of a user wearing the smart glass 10. The second camera 20 may also rotate up and down and side to side at a predetermined angle. The glass 30 is as transparent as general glasses, and the user wearing the smart glass 10 may watch his or her front through the glass 30. The glass 30 may serve as a transparent display for providing information. The controller 140 entirely controls an operation of the smart glass 100. Namely, the controller 140 entirely controls the components of the smart glass 100. For example, the controller 40 may analyze an image taken with the first camera 11 and the second camera 20. The controller 40 performs an operation for obtaining information about a front object the user watches based on the image analysis and may provide the obtained information for the user through the transparent display area of the glass 30. The controller 40 may analyze an image of the user's eyes taken with the first camera 11 and may execute a specific function corresponding to user's eye gesture recognized based on the result of the image analysis.

The microphone 50 may receive an external audio signal in a call mode, a recording mode and/or a speech recognition mode and may convert the received audio signal into electric audio data. The microphone 50 may employ various noise removal algorithms (or noise canceling algorithms) for removing or reducing a noise generated when the external audio signal is received.

The audio output device 60 may output audio data. The audio output device 60 may include a receiver, a speaker, a buzzer, and/or the like. The audio output device 60 may output sounds through an earphone jack. The user may hear the sounds by connecting an earphone to the earphone jack.

The touch sensor 70 may be configured to convert changes in a pressure or a capacitance applied by touching a predetermined area into an electrical input signal. The touch sensor 70 may be configured to detect a touch pressure as well as a touched position or area. The touch sensor 70 may be implemented as a proximity sensor. The proximity sensor has longer lifespan and more excellent utilization than a contact sensor. The date input through the touch sensor 70 may be used to execute the specific function of the smart glass 10.

The memory 80 may store a program for an operation of the controller 40 and also may temporarily store input/output data (for example, a phonebook, a message, a still image, a motion picture, etc.).

The memory 80 may include at least a flash memory, a hard disk type memory, a multimedia card micro type memory, a card type memory, such as SD or XD memory, a random access memory (RAM), a static RAM (SRAM), a read-only memory (ROM), an electrically erasable programmable ROM (EEPROM), a programmable ROM (PROM) magnetic memory, a magnetic disk and/or an optical disk. The smart glass 10 may also operate in relation to a web storage that performs a storing function of the memory 80 on the Internet.

The wireless communication device 90 may include at least one module capable of wireless communication between the smart glass 10 and a wireless communication system. For example, the wireless communication device 90 may include a broadcast receiving module, a mobile communication module, a wireless Internet module, a local area communication module, a position information module, and the like. Other modules may be used for the wireless communication device 90.

A power supply device may receive external power and internal power and may provide power required for operations of the components of the smart glass 10 under the control of the controller 140.

Various embodiments disclosed herein may be implemented within a recording medium that can be read by a computer or a computer-like device using software, hardware, or a combination thereof.

Figure 3B:
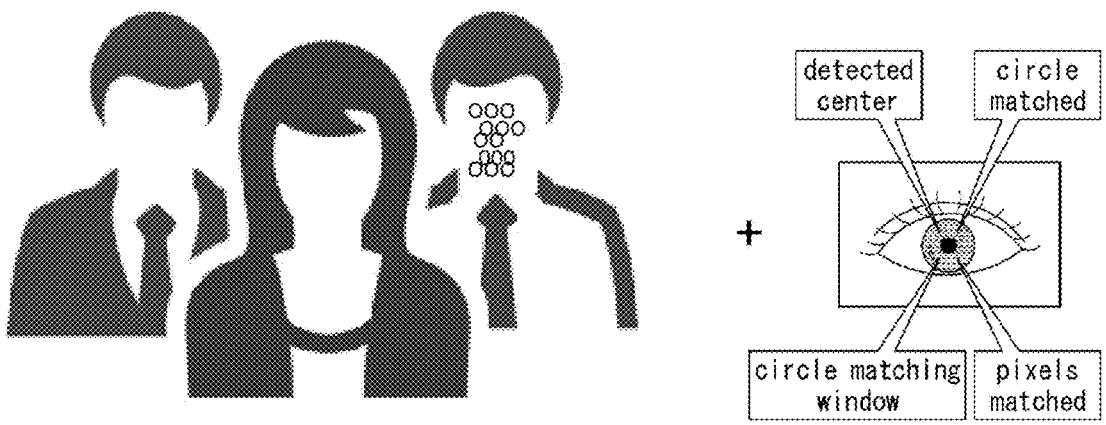
FIG. 3B shows an exemplary eye tracking example.

FIG. 3B illustrates an eye tracking process which performs the image analysis through the controller 40 and grasps a position of the user's gaze toward the front image. The result of the eye tracking is not necessarily provided for the user/displayed on the display area.

Figure 6:
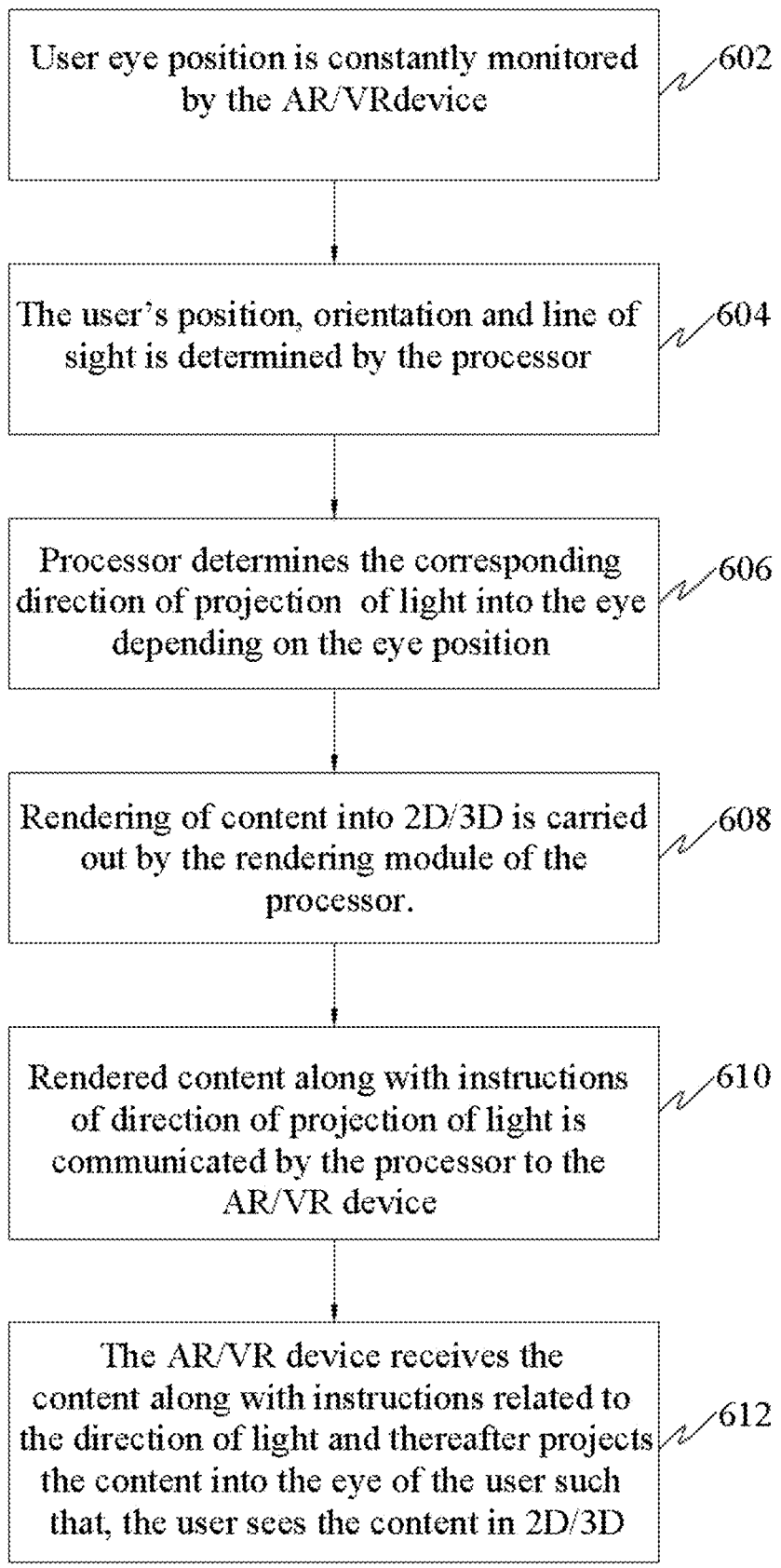
FIG. 6 is a flowchart illustrating the method of displaying virtual reality content to the user, in accordance with an embodiment.

When the front image includes a plurality of humans, the controller 40 performs a first eye tracking on the user's eyes and selects a specific human (in this example a plurality of O on the face). The controller 40 orients the microphones to pick up voice from the direction of the selected human so that the user can hear from the selected human. Optionally, a voice recognizer can transcribe the voice into text and displays for the user to respond. Optionally, the system displays information about the selected specific human and a graphic user interface including a function list for performing a specific function on the specific human on the transparent display area of the glass 30. The specific human is selected, and the function list capable of performing video capability, Facebook, and Twitter of the specific human is included in the graphic user interface 134. The function list may be previously determined based on attributes of the selected object. Namely, the function list may be used when the object selected by the user's gaze is the human. As another example, when a specific article is selected by the user's gaze, the controller 40 may display information about the specific article and the graphic user interface including a function for buying the specific article, a function for obtaining additional information about the specific article, etc. on the transparent display area of the glass 30. After the graphic user interface is provided, the controller 40 may perform a second eye tracking on the user's eyes and may select and execute one function included in the function list of the graphic user interface. For example, FIG. 6 shows that the smart glass 10 may execute a video capability function as the user gazes at an area corresponding to the video capability function of the specific human included in the graphic user interface.

In another example, an object included in the front image is selected by the user's gaze as the result of the eye tracking and information about the selected object is displayed on the transparent display area. As described above, the information about the selected object may be a search result of a specific network or a search result of the memory. The smart glass 10 as embodied and broadly described herein may provide the user with the information about the object selected by his/her gaze. If information about all of a plurality of objects included in the front image are displayed, user's front view may be obstructed. However, the smart glass 10 as embodied and broadly described herein may prevent the user's front view from being obstructed.

A smart phone can serve as a remote control unit for the hearing enhancement unit 100. The smart phone has a basic function for user control, such as changing the output volume level of the hearing aid 100, and when a microphone array having four microphones 131 is mounted, the smart phone may be used as the external microphone array 232-238. Information processing in the hearing system is appropriately distributed between a plurality of units in the hearing aid 100 and the external microphone array 232-238 in consideration of processing delay accompanied with communication or power consumption, regardless of wired or wireless and the configuration of each unit in the hearing system. For example, with the block configuration of FIG. 1, it is preferable that a DSP in the remote microphone performs sound source input processing and sound source separating processing, and a DSP in the hearing aid main body 110 performs other processing. Thus, communication signals between the external microphone array 232-238 and the hearing aid 100 may include only separated sound signals that are emphasized based on location/context, thereby improving sound at the user's ears while reducing a communication capacity. Sound source separation which has a large amount of processing is performed by the external microphone arrays which can use an AC adapter, thereby suppressing power consumption of the hearing aid main body 110.

If an interaural volume difference is used as a directional sense component, it is possible to determine the volume levels of the left and right output signals using a difference between each of the left and right volume levels and a predetermined reference volume level. Thus, there is no processing delay accompanied with the transmission of signals from the left and right units of the hearing aid main body 110 to the smart phone, such that the directional sense component is maintained in a state of nature. Since it is not necessary to directly compare the left and right volume levels with each other, it becomes possible to perform processing separately on the left and right such that the right output signal is generated in the right unit of the hearing aid main body 110, and the left output signal is generated in the left unit of the hearing aid main body 110. Thus, there is no processing delay accompanied with communication between the left and right.

Figure 4:
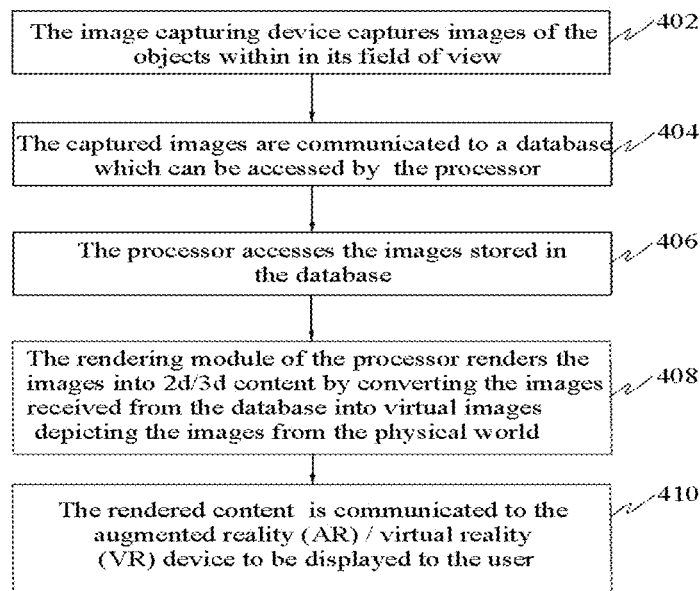
FIG. 4 is a flowchart illustrating the method of rendering virtual reality content to be displayed to a user in accordance with an embodiment.

Referring to FIG. 4, an embodiment discloses a method of rendering content to be displayed to the user, in accordance with an embodiment. At step 402, the image capturing device 312 may capture images of the objects within the field of view of the image capturing device 312. The field of view may include the instant surrounding of the user. The image-capturing device 312 may be a camera or other image sensors and may capture images from the instant surrounding within its field of view. At step 404, the captured images is communicated with the database 308, which can be accessed by the processor 302. At step 406, the processor 302 may access the images stored in the database 308. At step 408, the rendering module 304 of the processor 302 may render the images into two or three-dimensional content by converting the images received from the database into virtual images depicting the images from the instant surrounding of the physical world. The images may be rendered such that the user may see the images in either two or three dimensional formats. At step 410, the rendered content may be communicated to the AR device to be displayed to the user. The AR device may project the virtual content on the AR display device or on one or more display surfaces. This virtual content may be a portion of the entire content such as, the background scenery. The system 300 may further integrate simulated virtual images with the images depicting the instant surrounding and a combined virtual content may be rendered for display to the user. The user may be provided an option to choose content to be integrated with the images of the instant surrounding.

The processor 302 may generate virtual images by accessing the multimedia content. In an embodiment, the AR device may simulate data from the multimedia content and generate images of virtual objects. Such virtual images may be generated based on selection by the user. Virtual content may be generated by integrating the virtual images with the images of the surrounding by simulating the data in time, frequency and space.

Figure 5:
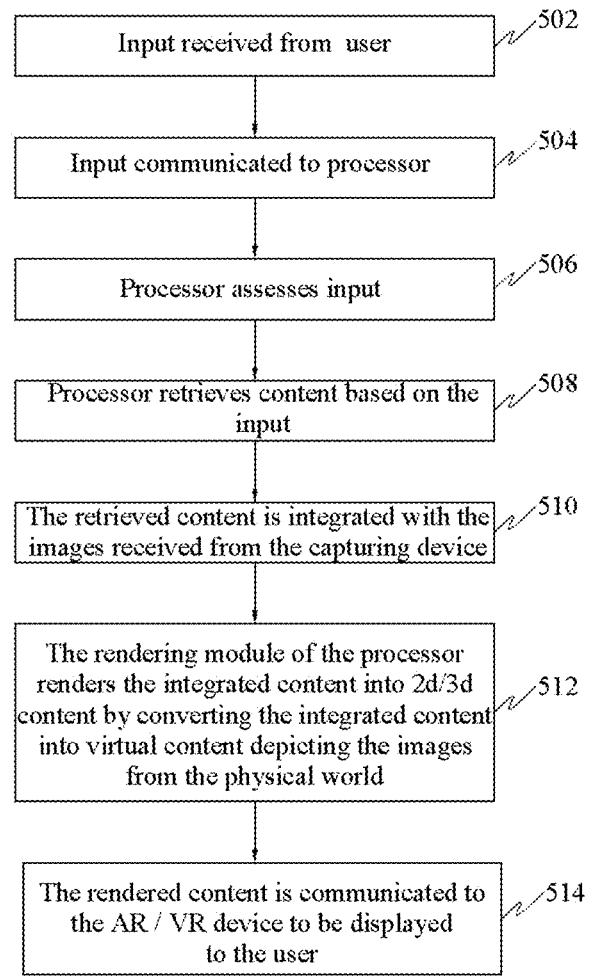
FIG. 5 is a flowchart illustrating the method of rendering virtual reality content to be displayed to the user, based on the input provided by the user.

FIG. 5 is a flowchart illustrating the method of rendering virtual reality content to be displayed to the user, based on the input provided by the user, in accordance with an embodiment. At step 502, the system 300 may receive input from the user. Such input may be information corresponding to what type of content the user is interested in viewing. The input may be provided through a physical keypad, which may be connected to the system 300 or a virtual keypad that the system 300 provides to the user. Alternatively, such input may also be provided by the user by touching or tapping options being provided to the user on a display interface. Such input may also be provided through voice. At step 504, the input received at the previous step may be communicated to the processor 302. At step 506, the processor 302 may assess the input. At step 508, the processor 302 may retrieve content based on the input. The content may be retrieved by accessing the multimedia servers or the database 308. At step 510, the retrieved content may be integrated with the images received from the image-capturing device 312. For this purpose, the processor 302 may determine interest points, define interest operators and construct an optical flow of the images of the instant environment captured through the image capturing device 312. The instant surrounding's pixel coordinates may be determined from the data obtained by processing the image. The processor 302, upon receiving input from users about the type or theme of the content to be rendered, may generate the image and, subsequently, determine the interest points, define interest operators and construct an optical flow of the virtual images that may be retrieved from the multimedia content. At step 512, the rendering module 304 of the processor 302 may render the integrated content into two or three dimensional content by integrating the content depicting the images from the physical world. At step 514, the rendered content may be communicated to the AR device to be displayed to the user. The AR device may display the content on the AR display device or a surface such as a wall, floor, table and ceilings, among others. The display surface may depend on the type of AR device. For example, if the AR device is a device worn like an eyewear, the display may be on the AR device's display surface. If the AR device is a head mounted device, then the display surface may be one or more of the display surfaces mentioned above. The processor 302 may be a self learning artificially intelligent processor to determine the type of content to be presented to the user. The processor 302 may learn from previous activities or selections made by the user and take into consideration such information while generating the content including the virtual images to be integrated with the images of the surroundings.

The sensors may receive inputs corresponding to parameters indicating a set of defined user characteristics. Characteristics may, for example, include head movement speed, head movement acceleration, and/or relationship between head movement and eye movement (e.g., ratio of one to the other), limb movement speed. The characteristics may even include indications of the tendency of a user to pay attention to certain virtual objects such as virtual object type (e.g., text, charts), movement of a virtual object (e.g., large shifts from image to image, fast or rapid movement, direction of movement), and characteristics of the virtual object (e.g., color, brightness, size), among others.

The user's eye and head movements and changes in position may be constantly monitored for displaying virtual content. A sensor, such as a position sensor may be integrated in the AR device which may be configured to monitor the viewer's (user) head and eye positions. The position information may be constantly communicated to the processor 302 and stored in the database 308. The processor 302 may determine the direction of light entering into the eye depending on the eye position. The line of sight may also be determined based on the eye position. The virtual content may be displayed to the user, based on the line of sight of the user.

FIG. 6 is a flowchart illustrating the method of displaying virtual reality content to the user, in accordance with an embodiment. At step 602, the user's eye position may be constantly monitored by the augmented reality device. At step 604, the information relating to the eye position may be constantly communicated to the processor 302. Such information may include how fast the eye movement changes, the position of the eye for each change and the line of sight, among others. Such information may be stored in the database 308 and retrieved by the processor 302 to determine the instantaneous velocity at which the eye may move. At step 606, the processor 302 may determine the corresponding direction of projection of light into the eye depending on the eye position. The determined direction of projection of light into the eye depending on the eye position may be stored in the database 308 for the processor 302 to retrieve in future. At step 608, the rendering module 304 of the processor 302 may carry out rendering of content into two or three-dimensional formats. At step 610, the processor 302 may communicate the rendered content, along with instructions of direction of projection of light to the AR device. At step 612, the AR device may receive the content along with instructions related to the direction of projection of light and thereafter project the content into the eye of the user such that, the user sees the content in two or three-dimensional formats. The processor 302 may further determine the velocity at which frames of images may be rendered based on the user's eye position. The processor 302 may estimate an instantaneous velocity at which the eye position changes and the information relating to the velocity may be communicated to the rendering module 304, such that images may be presented as continuous scene according to change in position of the eye.

Figure 7:
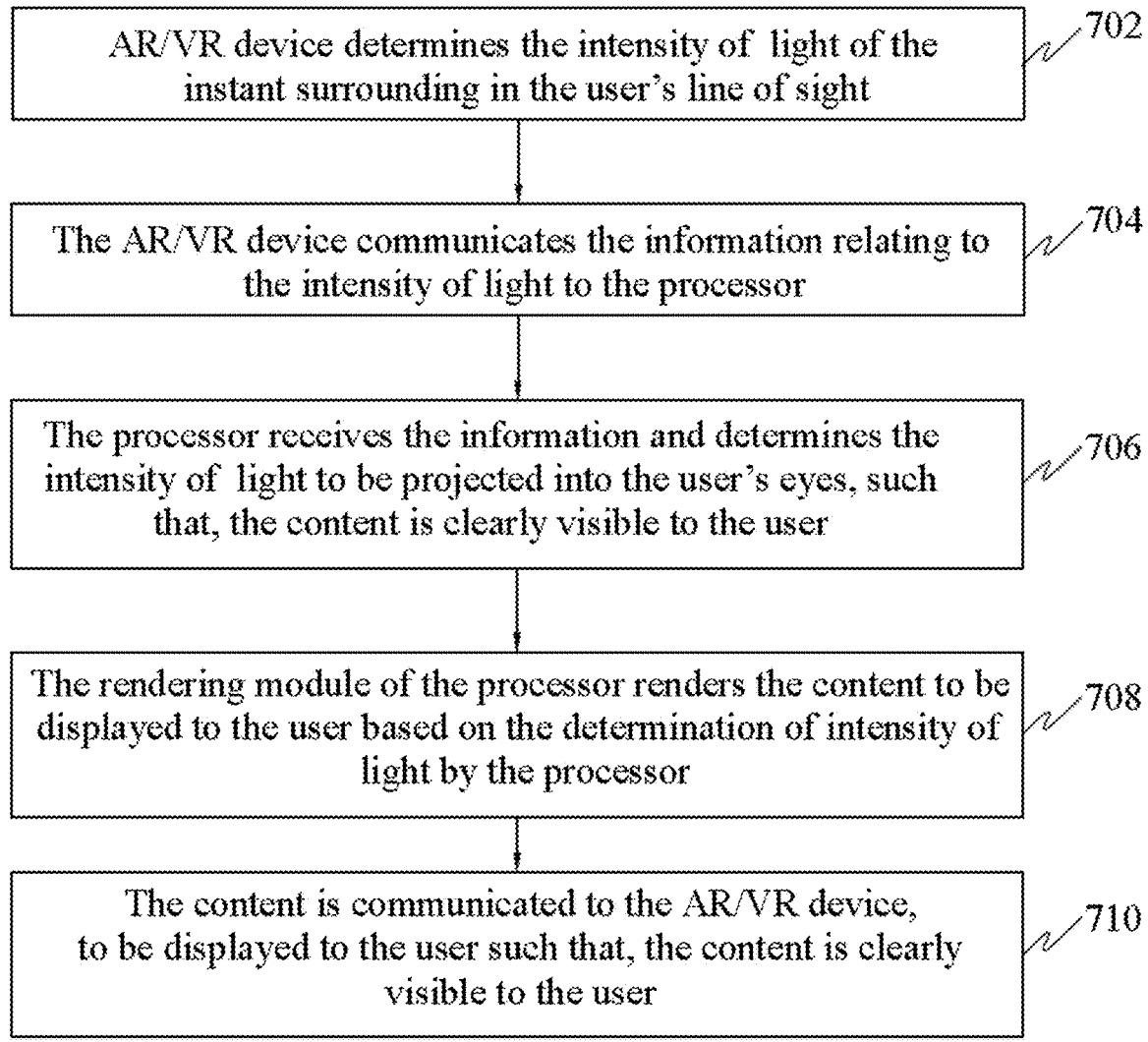
FIG. 7 is a flowchart illustrating the method of displaying virtual reality content to the user, such that the content is clearly visible to the user, in accordance with an embodiment.

Referring to FIG. 7, a method of displaying virtual reality content to the user, such that the content is clearly visible to the user, is illustrated. At step 702, the AR device may determine the intensity of light of the instant surrounding in the user's line of sight. At step 704, the AR device may communicate the information relating to the intensity of light to the processor 302. Such information may include information corresponding to ambient lighting of the environment, brightness of the objects and foreground and background lighting, among others. At step 706, the processor 302 may receive the information and determines the intensity of light to be projected into the user's eyes, such that, the content is clearly visible to the user. For example, the processor 302 may determine the intensity of light to be projected into the user's eye such that the user is clearly able to view an image of the surrounding, depending on the amount of brightness or darkness of the instant surrounding. The processor 302 may define areas of brightness and darkness in a scene and accordingly execute image correction algorithms and apply it on the images to be rendered. At step 708, the rendering module 304 of the processor 302 may render the content to be displayed to the user based on the determination of intensity of light by the processor 302. At step 710, the content may be communicated to the AR device, to be displayed to the user such that, the content is clearly visible to the user.

One or more sensors may receive input such as, tactile and gesture input, data indicating pressure and force vectors, applied through the user's limbs, among others. In an embodiment, the processor 302 may further receive voice data from the one or more sensors such as a microphone. This may be voice input provided by the user, wherein the voice input may correspond to a command. The processor 302 may be configured to receive input from the sensors and synthesize the input and derive the visual output or outcome based on the input. The derived visual output may be applied to the virtual images to alter one or more parameters (location, size etc) of the objects in the image. For example, in a car racing game, the input may correspond to pitch, yaw or roll data of a user's limbs. The user may change the position of the hands to steer a vehicle in the game, thereby altering the pitch, yaw or roll values of the hands. The processor 302 may determine the outcomes of the pitch, yaw and roll data and their effect on the content. The outcome, for example, may be, steering the vehicle to the left or right, or increasing or decreasing the speed of the vehicle.

In an embodiment, the gesture recognition database 310 may store gestures along with the semantics of each gesture received through the sensors. The semantics of the gestures may be predefined and stored in the gesture recognition database 310. The gesture recognition database 310 may also store outcomes of such input. The outcomes may indicate one or more physical actions carried by the user which may be applied to the virtual content to modify or alter parameters of the content. For example, if the user were to provide a gesture indicating expanding or zooming a particular object which is displayed to the user, the outcome would be zooming of the object. The gesture can be the action of zooming with his fingers. The system 300 may receive the input and accesses the gesture recognition database 310 to determine the outcome of the gesture input. The rendering module 304 may receive the outcome of the gesture input and render it in real time to the virtual content in order to alter details of the content. The gesture inputs may for example imply, resizing, adding, deleting, and shifting one or more items or objects of the content from one location to another. Gesture input may not only be limited to gestures made with fingers or hand, such input may also include tactile input, voice input and movement data of the user, among others.

Figure 8A:
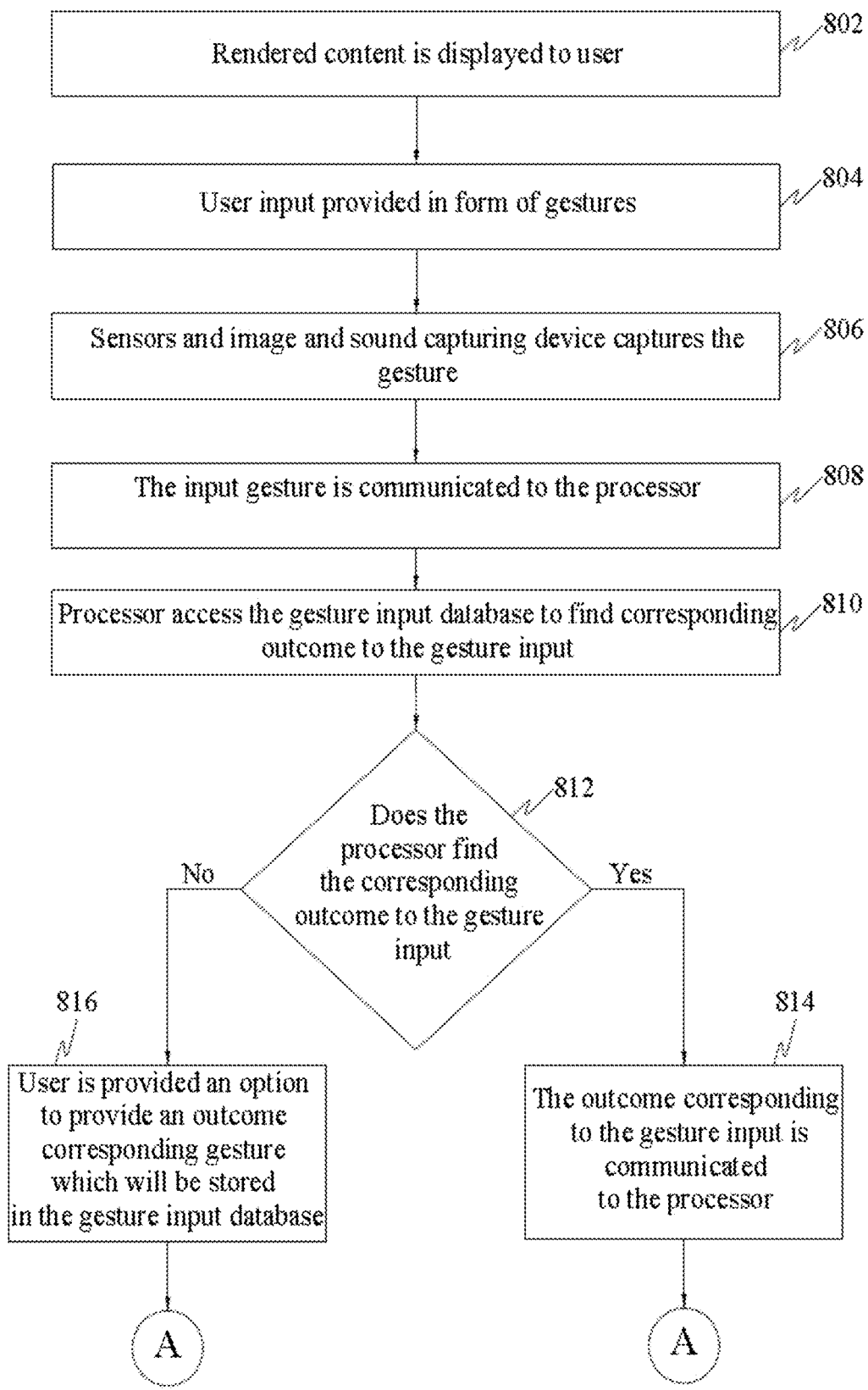
FIGS. 8A-8B is a flowchart illustrating the method of receiving gesture input from the user and thereafter rendering content to be displayed to the user, based on the gesture input, in accordance with an embodiment.
Figure 8B:
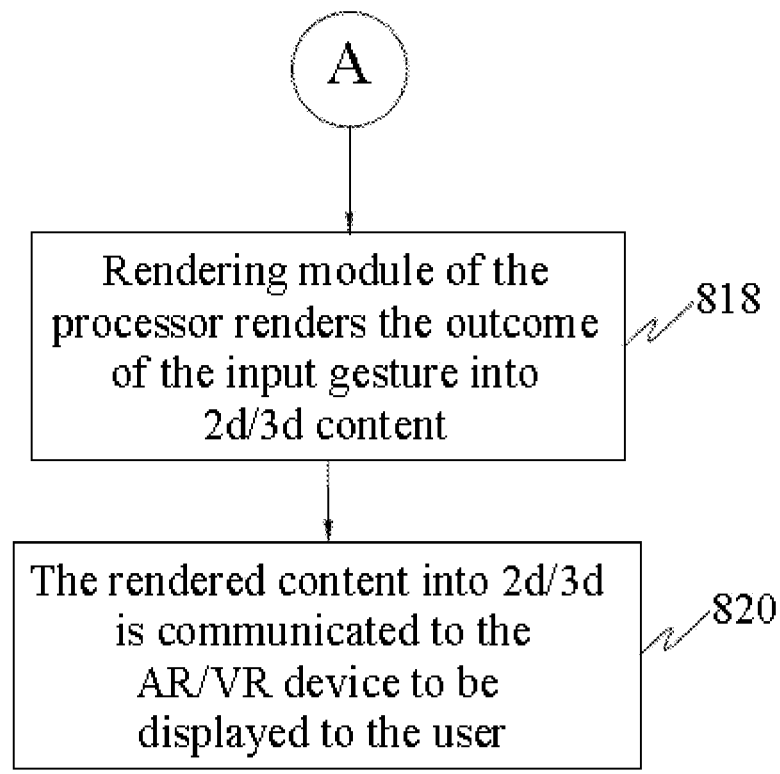

FIGS. 8A-8B is a flowchart illustrating the method of receiving gesture input from the user and thereafter rendering content to be displayed to the user, based on the gesture input, in accordance with an embodiment. At step 802, rendered content may be displayed to user. This rendered content may include the image of the instant surrounding combined with the images of virtual objects. At step 804, user input may be provided in form of gestures. At step 806, sensors and image or sound capturing device may capture the gesture. The image-capturing device 312 may be the image-capturing device that may be implemented to capture gestures. Sound may be captured through one or more microphones. These devices may be the parts of the input unit 306. These devices may be integrated into the system 300 or may be peripheral devices connected to the system 300. Such devices may be detachable from the system 300. At step 808, the input gesture may be communicated to the processor 302. The processor 302 may communicate with the gesture recognition database 310 to find the semantics of such input and derive an outcome corresponding to the input. At step 810, the processor 302 may access the gesture recognition database 310 to determine corresponding outcome to the gesture input. At step 812, the processor 302 may find the corresponding outcome to the gesture input. If the processor 302 is able to find the outcome corresponding to the gesture input, then at step 814, the outcome corresponding to the gesture input may be communicated to the processor 302. If the processor 302 is not able to find the outcome corresponding to the gesture input at step 812, then at step 816, the user may be provided an option to provide an outcome corresponding gesture which will be stored in the gesture recognition database 310. The user may provide outcome corresponding to the gestures through virtual keypads that may be displayed to the user. The user may also provide such input through a physical keypad connected to the system 300. At step 818, the rendering module 304 of the processor 302 may render the outcome of the input gesture into the two or three dimensional augmented reality content. At step 820, the rendered content may be communicated to the AR device to be displayed to the user. The outcome of the gestures may be used to alter, edit, add or delete one or more content in the images that are presented as the augmented reality content. The corresponding outcome may define one or more physical activities performed by the user such as, pointing at some object, moving an object, scrolling, deleting an object, adding objects, walking in virtual reality and speaking, among others. Some or all of the virtual reality content may get altered based on the input provided by the user.

As an example, the rendering module 304 may render the image of a desktop in either 2 dimensional or 3 dimensional form. The user may have set a password for one particular file on the actual desktop. The user may be currently viewing the desktop in virtual reality and the password protected file needs to be unlocked. The user may use the virtual keypad to enter input mapping to the password which may result in unlocking the file on the virtual as well as actual desktop. In another example, the user may be enabled to unlock a programme or show on a television in virtual reality. The system 300 may also enable locking and unlocking of physical or mechanical locks to virtual doors, gates and cars, among others. For example, a door may be rendered in virtual reality and the user may be required to walk through the door which is locked using a mechanical lock. The user may make gestures in space. The gesture may be communicated to the processor 302 to determine the outcome that may imply an unlocking action. The outcome may be rendered to the virtual reality content, thereby allowing the user to unlock the door.

In another example, the system 300 may display a virtual desktop. The files in the desktop may be arranged and displayed on the left side of the desktop. The user may require moving a file from the left hand side of the virtual desktop to the right hand side or to the taskbar of the virtual desktop. The user may use the physical or virtual keypad to enter inputs to the content that may be used to alter the file location on the virtual desktop. Alternatively, user may provide a gesture indicating moving the file from the left hand side to the right hand side. The gesture input may be communicated to the processor 302 through the motion sensors. The processor 302 may determine the outcome of the gesture and communicate the implication of the outcome to the rendering module 304. The rendering module 304 may render the implication and display the change in the virtual content by moving the file from the original position to the desired position.

In yet another example, the user may be enabled to alter content in a virtual football game. The user may be required to run and kick the ball by moving his feet in space to score goals. Pressure sensors may communicate the pressure and force applied by the user's feet. The user may be required to provide an input indicating forwarding the ball to another player. The motion, force and pressure vectors may be taken into account to determine the direction and force at which the ball may move. The output data corresponding to movements of the user's limbs may be rendered on the display. Whether a goal is being scored or whether the user has made a successful pass to another player may be rendered on the virtual reality content display based on the user's inputs.

In an alternate embodiment, the processor 302 may be configured to receive input from the virtual or physical keypad to alter or modify one or more details or objects of the virtual reality content.

Figure 9:
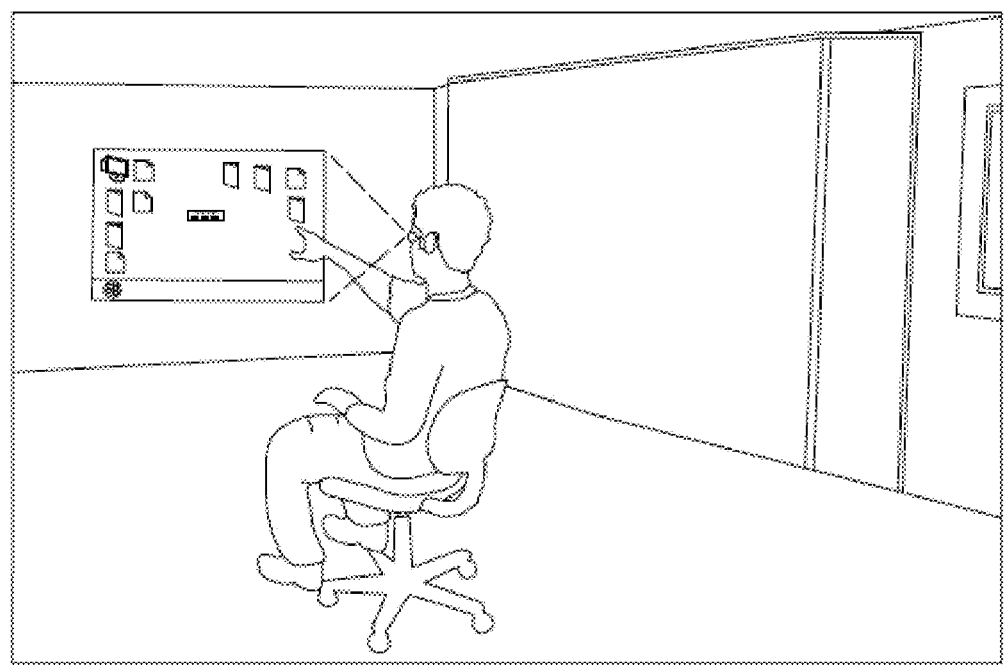
FIG. 9 is an illustration of the virtual reality content being altered by the outcome of a gesture input, in accordance with an embodiment.

FIG. 9 is an illustration of the virtual reality content being altered by the outcome of a gesture input, in accordance with an embodiment. The virtual content is being displayed to the user. The user may wish to view a particular object in the content by expanding the dimensions of the virtual object. The user may provide gesture with his fingers, which may correspond to expand. The portion of the content may be altered by rendering the outcome of the corresponding gesture.

In an embodiment, the depth of field of the user's eye may be calculated based on the eye movement and positions. The rendering module 304 may be configured to render the content into one or more resolutions to enable highlighting certain aspects of the content compared to other aspects of the content. For example, the content in the foreground may be of higher resolution compared to the content in the background. This may enable the user to have a more realistic view of the content, wherein objects nearer to the user are more pronounced in the visibility compared to objects which are farther from the user. The measure of depth of field may and the content being rendered based on the measurement may be applicable in enabling a user to view content in either two or three dimensional formats.

In an embodiment, the field of view of the user's eye may also be calculated based on the eye movement and positions. The field of view may be used to determine the extent to which the user may view the instant surrounding at any given instant.

Figure 10:
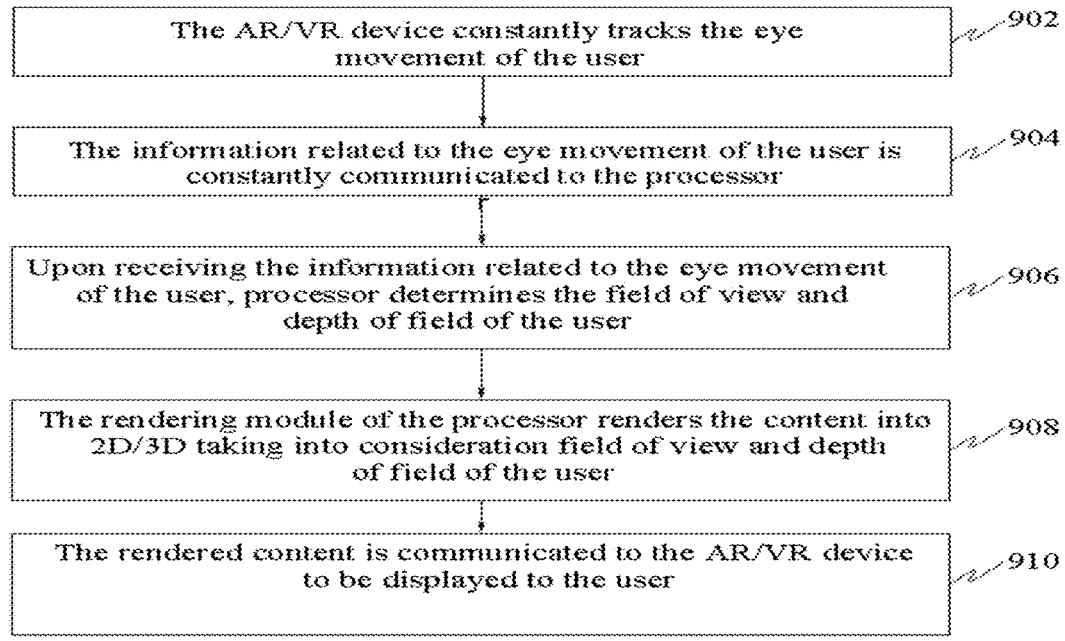
FIG. 10 is a flowchart illustrating the method of displaying virtual reality content to the user considering the field of view and depth of field of the user, in accordance with an embodiment.

FIG. 10 is a flowchart illustrating the method of displaying virtual reality content to the user considering the field of view and depth of field of the user, in accordance with an embodiment. At step 902, the AR device may constantly track the eye movement of the user. At step 904, the information related to the eye movement of the user may be constantly communicated to the processor 302. Such information may include how fast or slow the user' eye may move and change its position and line of sight, among others. Upon receiving the information related to the eye movement of the user, at step 906, the processor 302 may determine the field of view and depth of field of the user's eye. At step 908, the rendering module 304 of the processor 302 may render the content into two or three-dimensional formats taking into consideration field of view and depth of field of the user. At step 910, the rendered content may be communicated to the AR device to be displayed to the user. The user's head position may be constantly changing and the eye position may change relative to the movement of the head. The field of view of the user's eye may be calculated based on the line of sight and the position of the eye. Additionally, the horizontal and vertical field of view of the image-capturing device 312 or the focal length of the image-capturing device 312 may be measured to calculate the field of view of the user's eye.

Further, the rendering module 304 of the processor 302 may render the virtual reality content based on the user's position and orientation. The rendering module 304 may receive from the processor 302 data corresponding to the user's position and orientation. The processor may include pre-configured set of rules pertaining to the user's preferences of the format of display based on the user's position and orientation.

Figure 11:
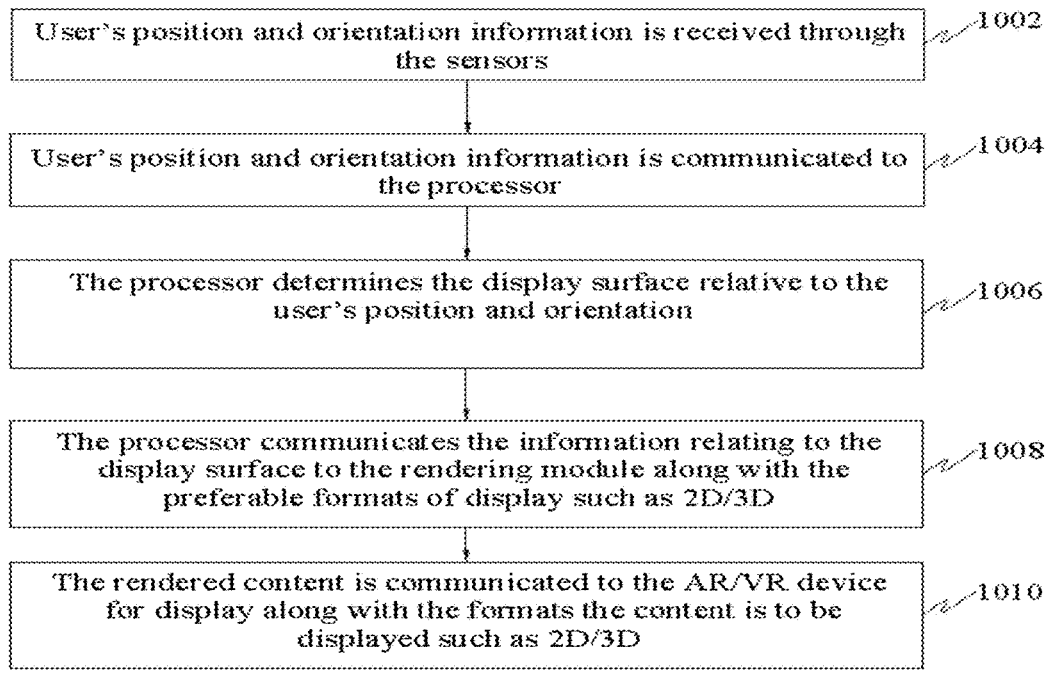
FIG. 11 is a flowchart illustrating the method of rendering virtual reality content based on the display surface, in accordance with an embodiment.

FIG. 11 is a flowchart illustrating the method of rendering virtual reality content based on the display surface, in accordance with an embodiment. At step 1002, the user's position and orientation information may be received through the sensors. At step 1004, the user's position and orientation information may be communicated to the processor 302. Such information may include information corresponding to a user's position such as sitting, standing, walking and lying in a horizontal position, among others. At step 1006, the processor 302 determines the display surface relative to the user's position and orientation. At step 1008, the processor 302 may communicate the information relating to the display surface to the rendering module 304 along with the preferable formats of display such as two or three-dimensional formats. At step 1010, the rendered content may be communicated to the AR device for display along with the formats the content to be displayed.

Displays may be presented to the user based on the user's position and orientation, in accordance with an embodiment. As an example, the user may be presented a holographic display interface based on the position and orientation. Users may be provided options to choose interfaces based on preference, location and orientation, among others. For example, one interface could be displayed while the user is working or taking part in a conference or event, another interface could be displayed while the user is participating in a leisurely activity such as a game. Furthermore, another interface could be displayed while the user is sitting on a couch and watching a movie. Each of these display interfaces may be different from one another. Each of these display interfaces may be configured to display virtual reality content based on the user's position data, movement data, orientation of head and eyes and orientation of limbs, among others.

Further, the display interfaces may be changed for the user based on the theme of the content being displayed. For example, when the user is watching a movie on Netflix, the display interface may be different from the display interface that is presented while the user is watching sports on ESPN. For example, while watching ESPN posters of players or advertisements may be rendered for display on blank walls.

The processor 302 may be a self learning artificially intelligent processor to determine the format of display to be presented, based on the user's position and orientation. Upon rendering the content based on the user's position and orientation, the virtual reality content may be communicated to the VR device to be displayed on the display surface. As an example, if the user is sitting on a couch and the head is tilted towards the right, the display may also be tilted relative to the position of the head. Further, relative to the overall orientation of the user's body, the display surface may be selected by the system 300, such as, wall, ceiling and floor, among others. Furthermore, the display may be a curved display of a straight display. The virtual reality content may be rendered to be displayed on curved display surfaces. The virtual reality content or at least a portion of the content may be remapped such that the virtual reality content may be displayed on curved display surfaces. The rendering module 304 may remap the virtual reality content and render the content to be displayed on curved surfaces.

The rendering module 304 may render two dimensional or three dimensional visual content for display based on the user's position and orientation data. The virtual reality content may, as an example, also be displayed or projected in space as holographic display.

Figure 12:
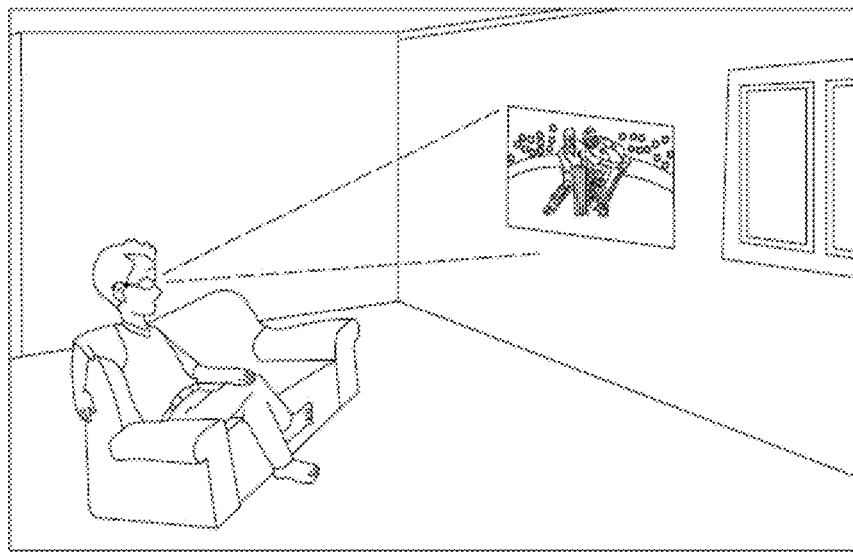
FIG. 12 illustrates display interfaces which may be presented to the user based on the user's position and orientation, in accordance with an embodiment.

Referring to FIG. 12, in another embodiment the system 300 may enable a plurality of users to participate in an activity and communicate, in virtual reality. The system 300 may include a communication module 1202. The system 300 may be configured to communicate with one or more remote servers 1204 via the communication module 1202. The system 300 may be located on a server which may not be located on the VR device and the system 300 may be configured to communicate with the VR device. Alternatively, the system 300 may be located on the VR device. The VR device may project the virtual content based on the instructions received from the processor 302. The virtual content may be images of other users or videos of other users. The system 300 may include one or more image capturing devices. The rendering module 304 may be configured to render virtual content in one or more formats upon receiving instruction from the processor 302.

In an embodiment, the system 300 may be configured to communicate with one or more servers 1204 to retrieve user information. The communication module 1202 may enable the system 300 to communicate with the servers 1204. The communication module 1202 may also enable communication of data from the processor 302 to the AR device. The processor 302 may be configured to store information retrieved from the server 1204 in the database 308. The stored information may be information corresponding to the user's profile, relationship information with other users on one or more social networking platforms and one or more activities the user may be performing, among others. Based on the data stored, the processor 302 may generate lists of preconfigured themes that may represent the activities of the user. The user may be provided an option to select one or more themes depending on the type of the activity, the user may be indulged in. Such lists may be provided to the user on a virtual interface such that the user may select one or more options from the lists.

Figure 13A:
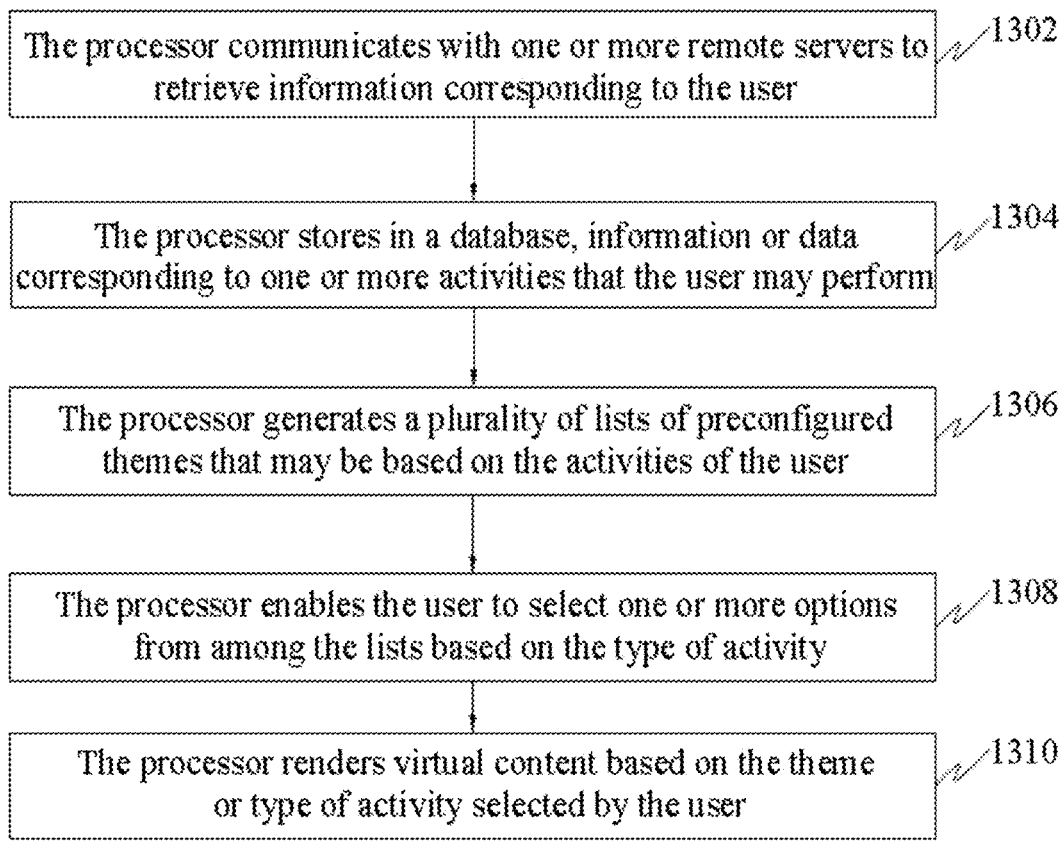
FIG. 13A is a flowchart illustrating the method of rendering virtual content based on the theme or the type of activity a user may be performing, in accordance with an embodiment.

FIG. 13A is a flowchart illustrating the method of rendering virtual content based on the theme or the type of activity the user may be performing, in accordance with an embodiment. At step 1302, the processor 302 may communicate with one or more remote servers 1204 to retrieve information corresponding to the user. At step 1304, the processor 302 may store in the database 308, information or data corresponding to one or more activities that the user may perform. At step 1306, the processor 302 may generate a plurality of lists of preconfigured themes that may be based on the activities. At step 1308, the processor 302 may enable the user to select one or more options from among the lists of themes, which may be based on the type of activity the user may be involved in. At step 1310, the processor 302 may render virtual content based on the theme or type of activity selected by the first user.

Further, a set of machine learning algorithms may enable the processor 302 to learn from the previous choices of theme for an activity selected by the user and thereby automatically select themes based on the activity of the user. Machine learning algorithms may be stored in the database 308 and accessed by the processor 302. Upon selecting the theme, content may be rendered into virtual reality.

Further, the user may be required to provide necessary additional information such that the processor 302 may be able to select the theme based on input provided by the user. Such content may correspond to sceneries that may be able to provide the user experience of the activity the user may be participating in.

Figure 13B:
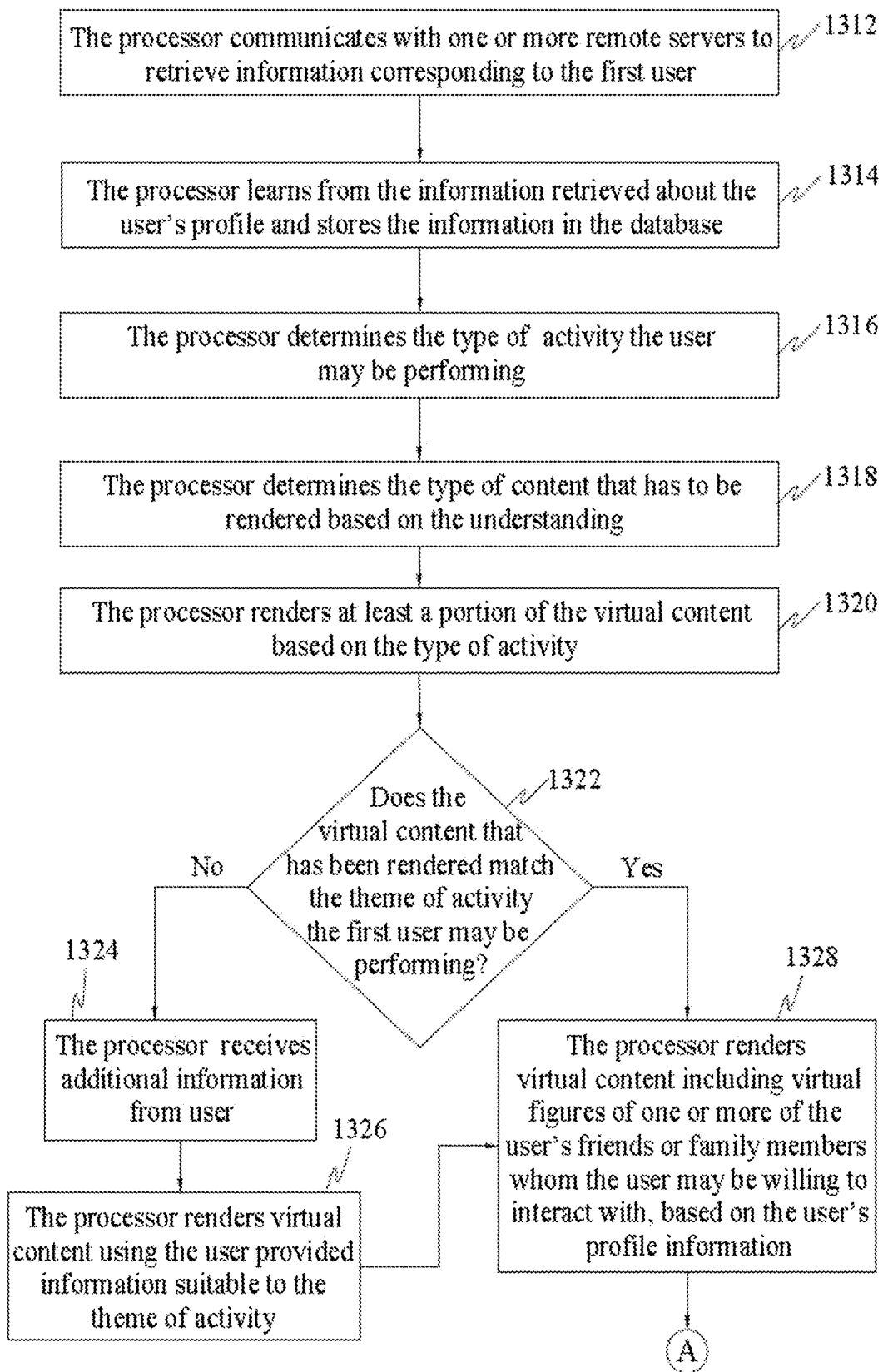
FIG. 13B-13C is another flowchart illustrating the method of rendering virtual content to the user based on the theme or the type of activity the user may be performing, in accordance with an embodiment.
Figure 13C:
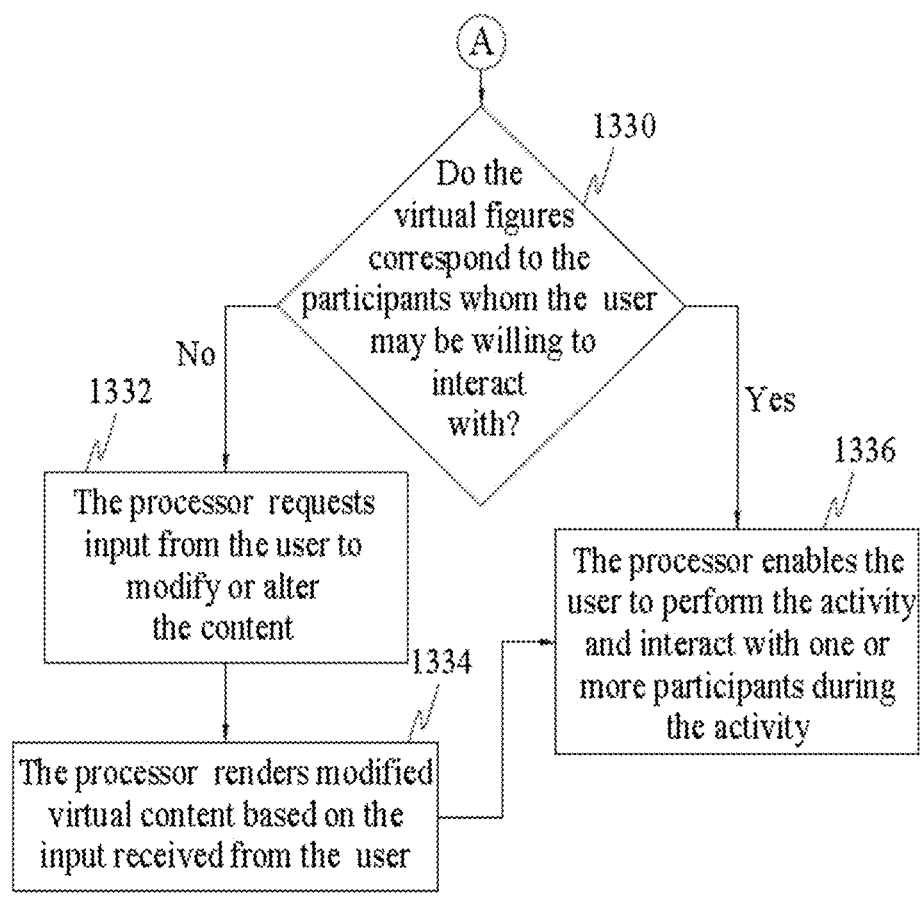

FIG. 13B is another flowchart illustrating the method of rendering virtual content to the user based on the theme or the type of activity the user may be performing, in accordance with an embodiment. At step 1312, the processor 302 may communicate with one or more remote servers 1204 to retrieve information corresponding to the user. At step 1314, the processor 302 may learn from the previous activities of the user, choice of themes by the user, relationships, preferences, hobbies, work schedule among other information and store the information in the database 308. At step 1316, the processor 302 may determine the type of activity the user may be performing. At step 1318, the processor 302 may determine the type of content that has to be rendered based on the determination of the activity. At step 1320, the processor 302 may render at least a portion of the virtual content based on the type of activity. Such virtual content rendered at this step may be only a portion of the entire content, such as, for example, the background and scenery that may form the background, among others. Such content may also include one or more other participant's virtual model. At step 1322, whether the virtual content matches the theme of activity the first user may be performing, may be determined. At step 1324, if the virtual content does not match the theme of activity which the user may be performing, then the processor 302 may request additional information from the user. Based on the received additional information, the processor 302 may, at step 1326, render virtual content using the user provided information suitable to the theme of activity. At step 1322, if the virtual content matches the theme of the activity, then at step 1328, the processor 302 may render virtual images of one or more other participants whom the user wishes to be participants in the activity. The selection of other participants in the activity may also be based on the user's profile information. The processor 302 may be configured to execute step 1328 after step 1326. The virtual images of one or more of the user's friends or family members whom the user may be willing to participate with depends on the information corresponding to the user's profile. For example, the user may wish to perform yoga with his family members. The processor 302 may receive this information from the user and subsequently may provide or render the virtual images of one or more family members of the user. At step 1330, whether the virtual images correspond to the participants whom the user may be willing to participate with, may be determined. If the virtual images do not correspond to the participants whom the user may be willing to participate with, then the processor 302, at step 1332, may request for input from the user to modify or alter the content based on the input provided by the user. At step 1334, the processor 302 may render modified virtual content based on the input received from the user. If the virtual figures correspond to the users whom the user may be willing to participate with, then, at step 1336, the processor 302 may enable the user to perform the desired activity and interact with one or more participants during the activity. Further, the processor 302 may also be configured to render images of other participants, who may not engage in the activity. The processor 302 may only display images of participants who may not engage in the activity. The processor 302 may be configured to execute step 1336 after step 1334.

In an embodiment, the content that may form the scenery may be displayed on one or more display interfaces. Such content may be in two or three dimensional format based on one or more factors, such as, the type of content, type of display interface and user's preference among others. The display interfaces may be, for example, a wall, floor and ceiling among others. The AR device may be configured to project the rendered images onto the display interface.

Figure 14A:
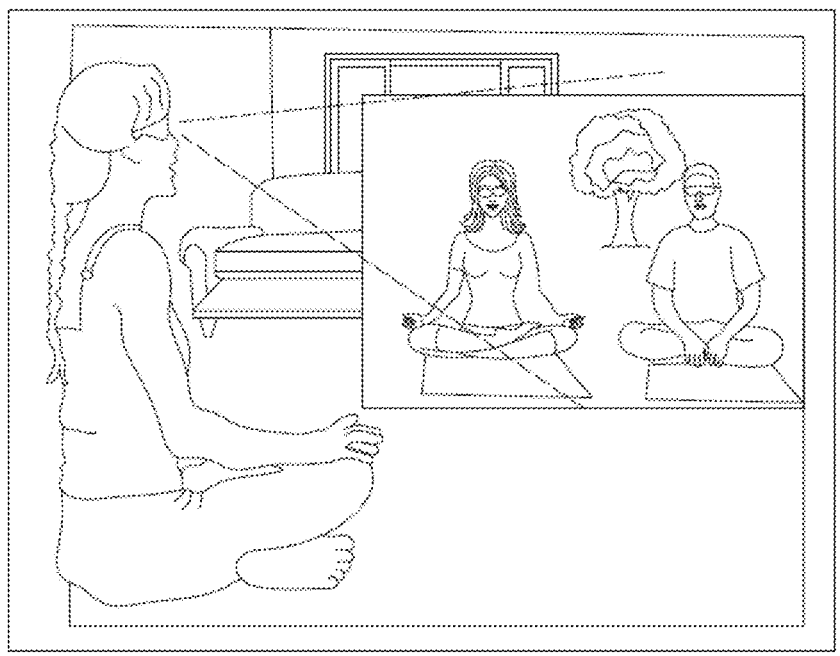
FIGS. 14A-14C illustrate exemplary scenarios wherein the system may be implemented, in accordance with an embodiment.
Figure 14B:
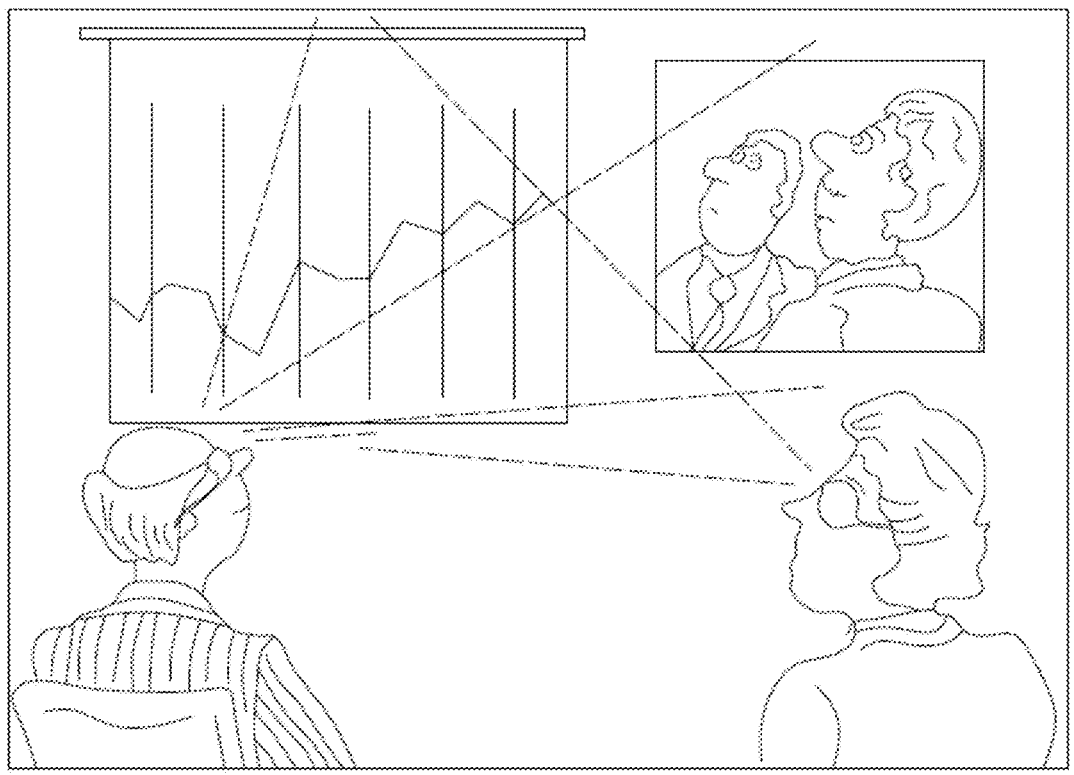
Figure 14C:
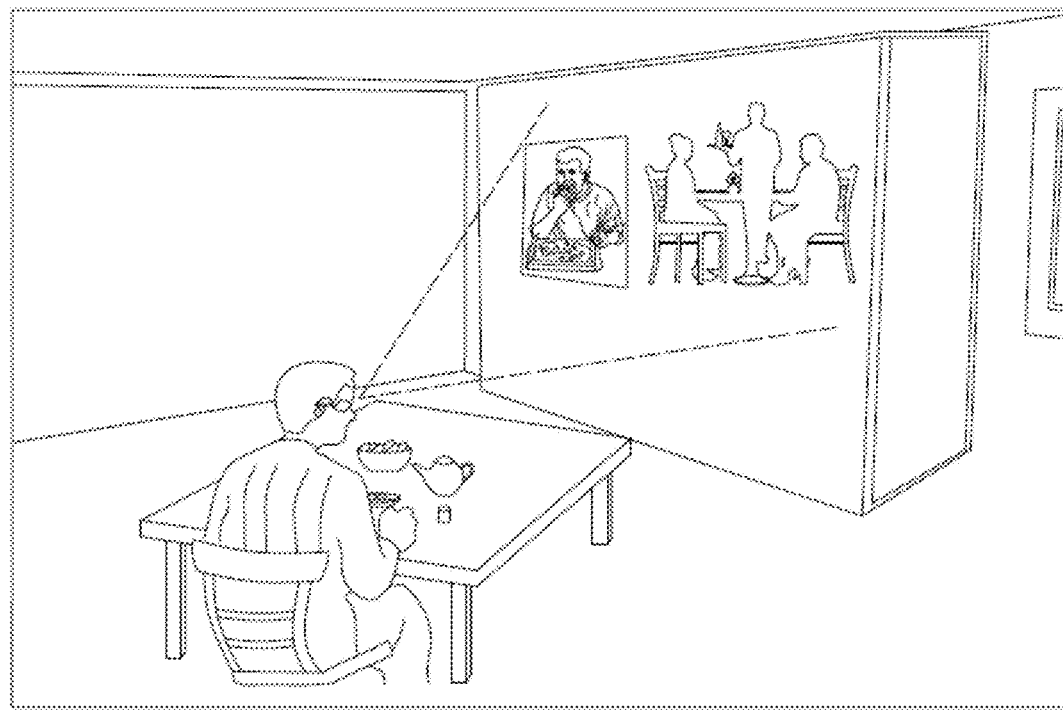

FIGS. 14A to 14C illustrate exemplary scenarios wherein the system 300 may be implemented, in accordance with an embodiment. In an example and referring to FIG. 14A, the system 300 may be configured to render virtual content, showing the virtual presence of one or more participants to a user while the user is at home preparing for a yoga session. The user may be wearing his/her AR device. The system 300 may render virtual content displaying the virtual images of one or more participants whom the user may or may not know in person. The system 300 may also allow the one or more participants to communicate with the user through the communication module 1202 during the session through voice or through texts or both voice and text. The system 300 may render the virtual content such that the user may experience an environment where the user is performing yoga with the plurality of other participants. The system 300 may also render the virtual image of an instructor whom the user may or may not know in person. The system 300 may further render suitable background scenery of a meadow or a meditation hall, among other backgrounds.

In a second exemplary scenario and referring to FIG. 14B, the system 300 may be implemented in a scenario to replace business travel by virtual teleconferences where participants may experience the feeling of physically being present at the location, interacting with their co-workers or clients, even though they may not be physically present at the location. The participants who may be wearing the VR devices may be provided access to other participants who may be participating in the conference virtually.

However, the participants participating virtually may be able to see all the participants, who are physically present at the conference and who are virtually participating in the conference. Similarly, the participants, who are physically present at the conference, may be able to see all the virtual participants. This can be enabled by providing a video camera at the conference, which may record the events at the conference as well as images and videos of the participants of the conference. One or more of the participants may be enabled to take control of the session. The participant(s) who may be taking control of the session may be able to initiate the session and allow other participants to provide data to be displayed as virtual content, while the session is in progress. The data provided by the participants may be data related to the teleconference.

In a third exemplary scenario and referring to FIG. 14C, the system 300 may be implemented in a scenario where the user may be willing to dine at home as well as feel the presence of one or more of his friends or family members beside him. The processor 302 may render virtual content by receiving input from the user. The processor 302 displays the background as the scenery of a restaurant. The virtual content representing the scenery of a restaurant may be displayed to the user. The user may be enabled to select one or more friends and family members whose presence the user wishes to feel or whom the user wishes to have as participants while dining. The processor 302 may render the virtual images of those people selected by the user. The processor 302 may render the virtual image of his/her friends on a display interface such as holographic display interface. The user may be enabled to communicate with his friends while dining, through the communication module 1202.

In an embodiment, and referring to the above examples, the processor 302 may, retrieve from the database 308, information corresponding to the user's social networking profile and the user's relationship information with other users on the social networking platform. The profiles of one or more users with whom the user may be connected on the social networking platform may be retrieved and stored in the database 308. The processor 302 may generate the virtual content based on the information retrieved. The processor 302 may further instruct the VR device to display virtual models of one or more of the user's friends whose profiles may be stored in the database 308.

Alternatively or additionally, the system 300 may be configured to receive inputs from the user wherein the input may include information corresponding to the user. Such information may include a user's name, place of work, contact details, home address, list of friends of the user and their contact information, hobbies, activities the user may be involved in and recent activities the user was engaged in and daily activity schedule, among other information. Such information can also be fed to the system 100 by the user, such as, for example, by filling a questionnaire and may be stored in the database 308. The user may also provide information corresponding to his/her friends and family members such as, place of work, hobbies, activities they may like doing and recent activities they were engaged in and daily activity schedule among other such information.

In an embodiment, the processor 302 may be configured to understand the user's interest, preferences and priorities among others based on the information corresponding to the user's profile. The processor 302 may also be configured to learn what activity the user may be performing at a particular time of the day, or on any particular day, based on the user's daily activities and previous activities. Such information may be stored in the database 308 and retrieved from the same whenever necessary. Based on the learning, the processor 302 may generate the virtual content by retrieving the user's profile information from the database 308.

Figure 15A:
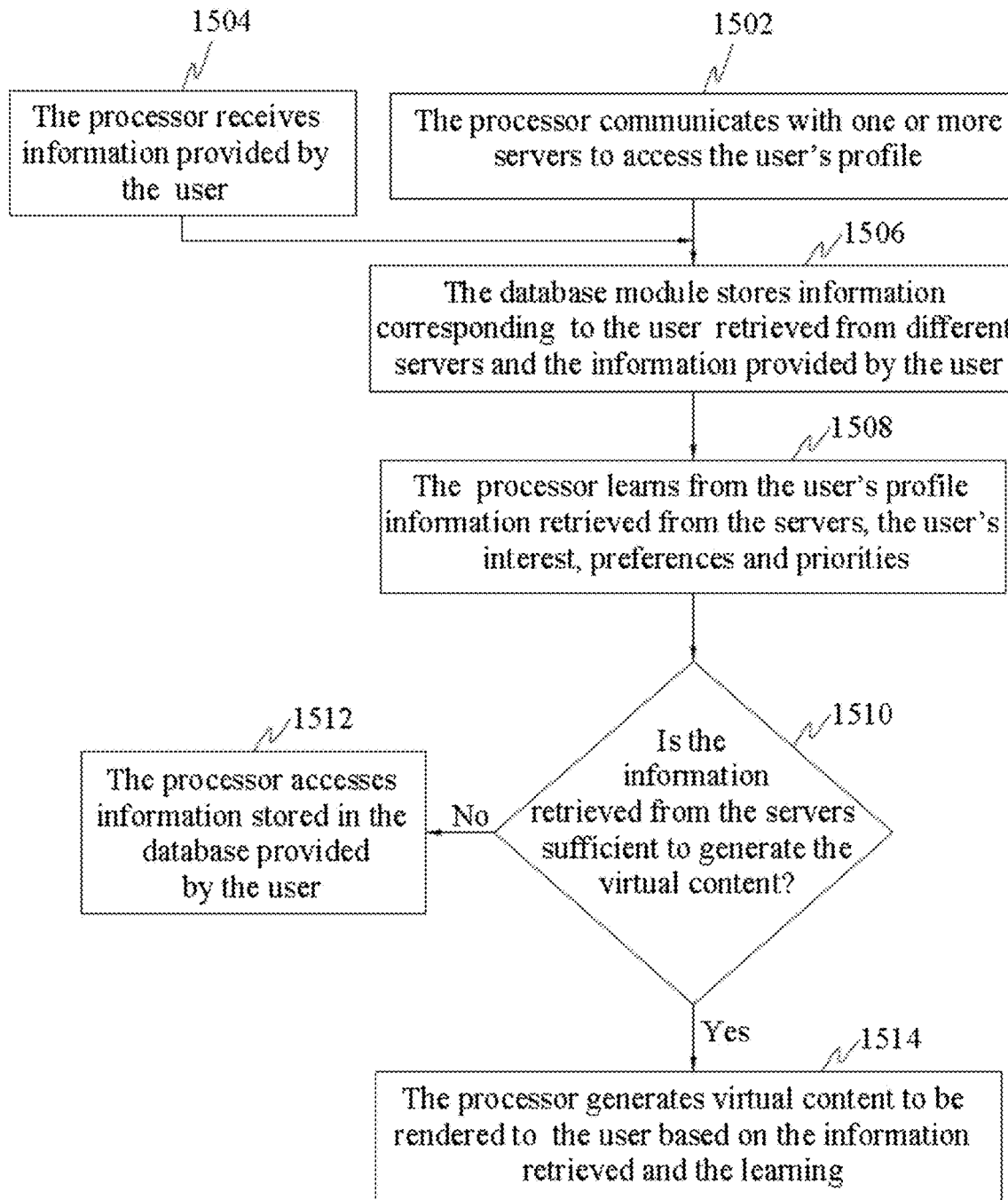
FIG. 15A is a flowchart illustrating a method of receiving information corresponding to the user and generating virtual content based on the information corresponding to the user retrieved from a database module 308, in accordance with an embodiment.

FIG. 15A is a flowchart illustrating a method of receiving information corresponding to the user and generating virtual content based on the information corresponding to the user retrieved from the database 308, in accordance with an embodiment. At step 1502, the processor 302 may communicate with one or more servers 1204 to retrieve information corresponding to the user and other participants the user may be connected with on one or more platforms. The platforms may be for example, social networking platforms. At step 1504, the processor 302 may further receive information corresponding to the user and other participants the user may be connected with on one or more platforms provided by the user. The user may provide such information manually through a user interface that may be associated with the system 300. At step 1506, the database 308 may store the information corresponding to the user retrieved from different servers 1204 and the information provided by the user. Information provided by the user may include information corresponding to one or more users the user may know or may be willing to participate with, in an activity. At step 1508, the processor 302 may learn from the user's profile information retrieved from the servers 1204, the user's interest, preferences and priorities. At step 1510, whether the information retrieved from the servers 1204 is sufficient to generate the virtual content, may be determined. If the information from the servers 1204 is not sufficient, the processor 302, at step 1512, may access the information stored in the database 308, which may be provided by the user. If the information from the servers 1204 is sufficient to generate the virtual content, then, at step 1514, the processor 102 may generate virtual content to be rendered and displayed to the user based on the information retrieved. Also step 1514 may be executed after step 1512.

In an embodiment, the processor 302 may instruct the VR device to display a list showing the names or profiles of one or more users whom the user might have interacted with on one or more platforms earlier. Such profiles may be stored in the database 308. The user may be provided an option to select one or more users to participate in an activity with from the displayed list. Such a list may be generated by the processor 302 by accessing the database 308. The processor 302 may instruct the VR device to provide virtual images of one or more of the users whose names and profile information may be displayed on the list. The processor 302 may render the virtual content and communicate it to the VR device for display.

The processor 302 through the communication module 1202 may further be configured to notify the participants, whose profiles have been selected by the user, about the user's interest in participating in the activity with them. One or more of the participants to whom the notification may have been communicated, may show interest in joining the user in the activity. The processor 302 may accept response from one or more participants who may show interest in joining the user in the activity. The processor 302 may render the virtual content displaying the presence of the participants who may have responded showing interest in joining the user. The virtual content may be videos of the other users. The user may be enabled to communicate or interact with the other users through the communication module 1204. The image capturing device of the system 300 may capture images of the user and communicate it to the other users. Similarly, the respective image capturing devices of the systems 300 of the other users may capture the image and voice of the other users and communicate it to the user.

In yet another embodiment, the user may be enabled to send requests to one or more participants, whom the user may be acquainted with, to join the user during the yoga session. The other participants may accept or decline the request. The processor 302 may display the virtual presence of the participants who may have accepted the user's request. The virtual content may be videos of the other users. The user may be enabled to communicate with the other participants through voice data. Alternatively, the user may be able to send requests to one or more users whom the user may be connected with on a social networking platform. The image capturing device of the system 100 may capture images of the user and communicate it to the other users. Similarly, the respective image capturing devices of the systems 100 of the other users may capture the image and voice of the other users and communicate it to the user. The other users may replicate the actions performed by the user.

Figure 15B:
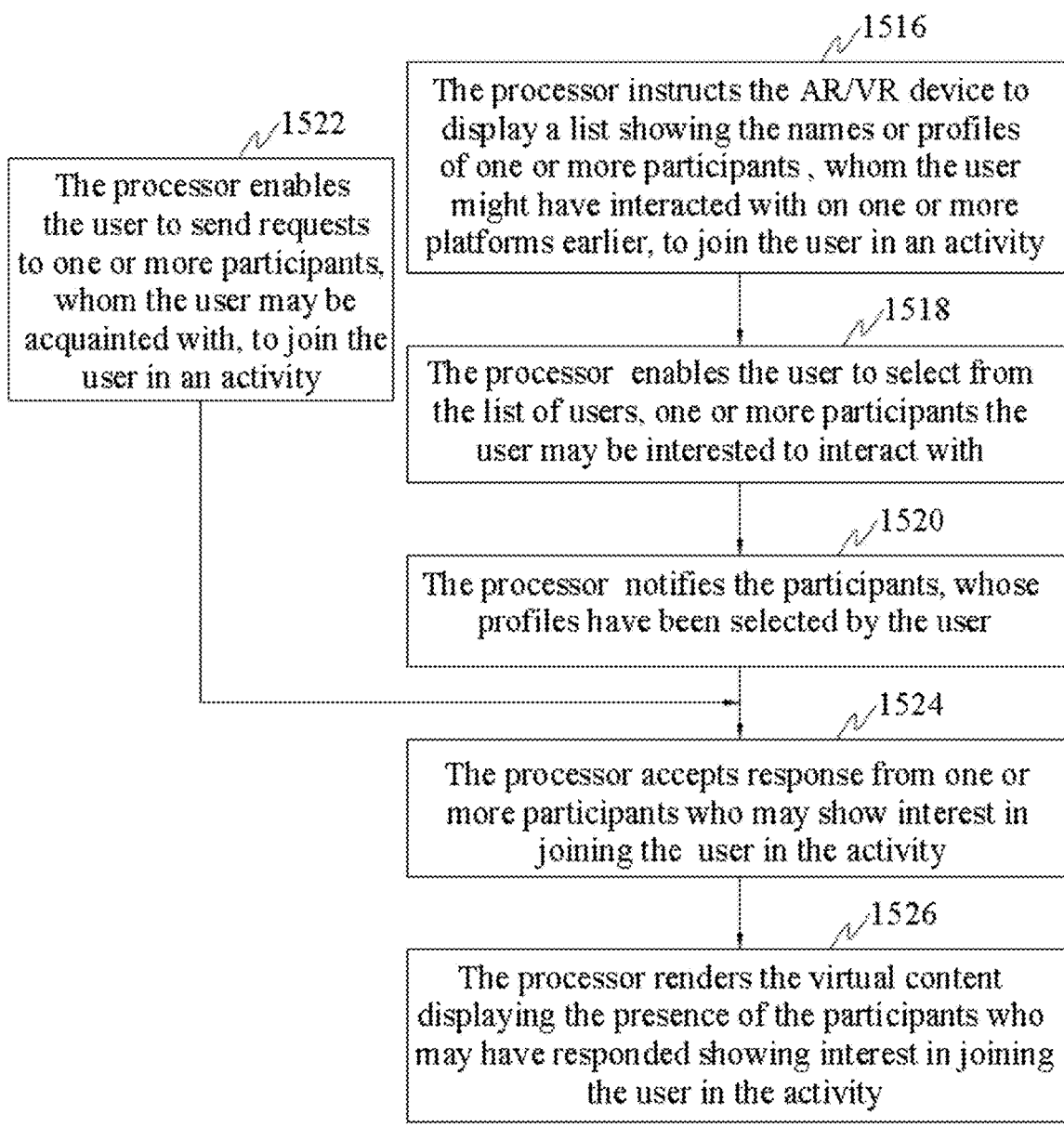
FIG. 15B is a flowchart illustrating the method of rendering virtual content based on the user's selection of participants in the activity, in accordance with an embodiment.

FIG. 15B is a flowchart illustrating the method of rendering virtual content based on the user's selection of participants in the activity, in accordance with an embodiment. At step 1516, the processor 302 may instruct the VR device to display a list to the user, displaying the names or profiles of one or more participants, whom the user might have interacted with on one or more platforms earlier, to join the user in an activity. At step 1518, the processor 302, may enable the user to select from the list of users, one or more participants the user may be interested to participate with. At step 1520, the processor 302 may notify the participants, whose profiles have been selected by the user. At step 1522, the processor 302 may further enable the user to send requests to one or more participants, whom the user may be acquainted with, to join the user in an activity. It may be noted that the steps 1516 and 1522 can be optional and may be executed individually in two different scenarios. At step 1524, the processor 302 may accept response from one or more participants who may show interest in joining the user in the activity. At step 1526, the processor 302 may render the virtual content displaying the presence of the participants who may have responded showing interest in joining the user in the activity.

In another embodiment, the processor 302 may be configured to render virtual content displaying virtual presence of one or more participants whom the user may be willing to participate with, based on preconfigured or configurable set of rules incorporated in the processor 302. The processor 302 may learn from the user's previous interactions and types of activities and thereby determine, whom the user may be willing to participate with for one particular activity. For example, the user may have participated in yoga sessions with users A, B and C on one particular day and with users B, D and G on a second day. On a third day, the processor 302 may render virtual content wherein the virtual content may display virtual model of user B and allow the user to select other users in addition to user B to perform yoga.

Figure 15C:
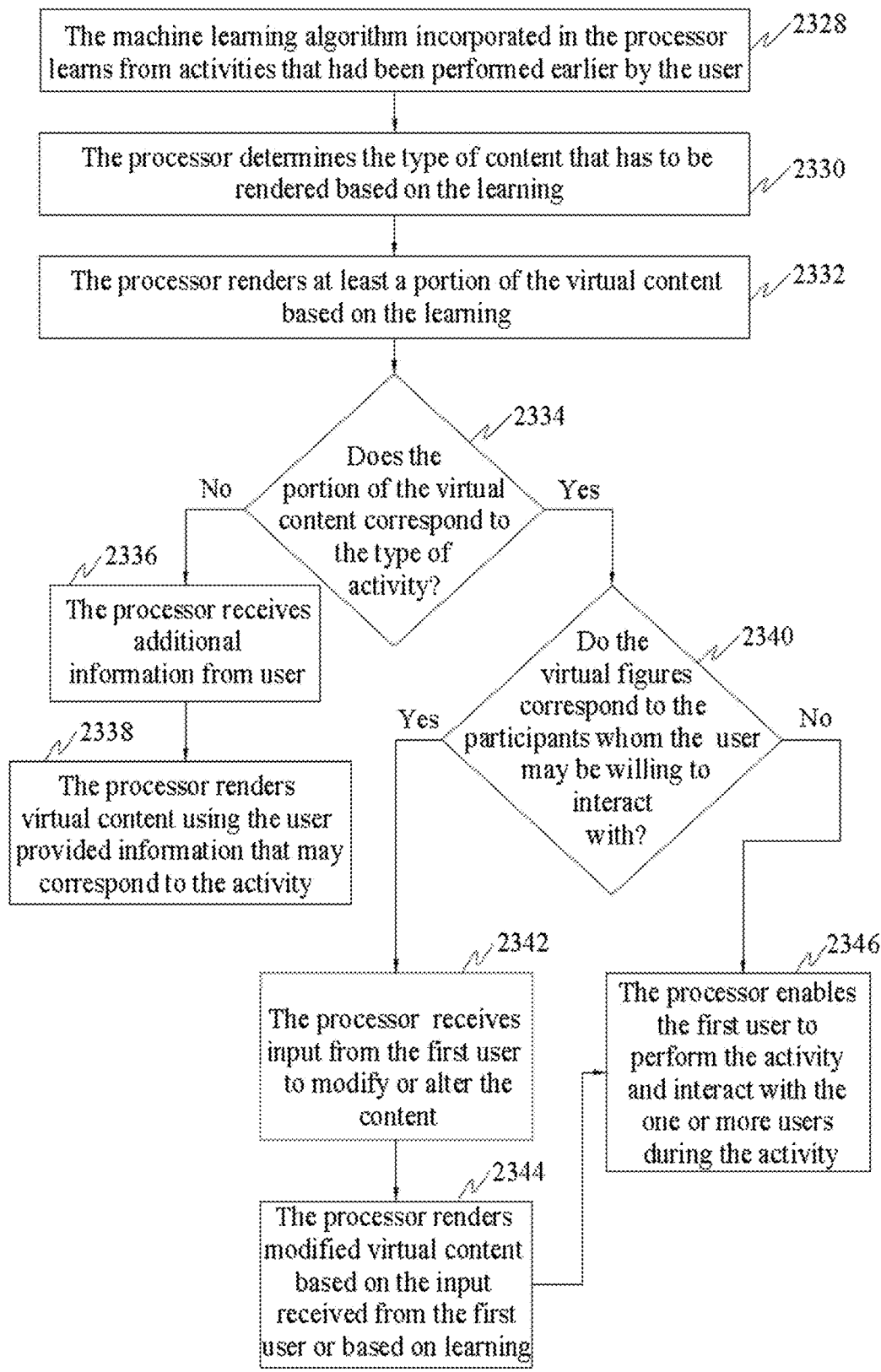
FIG. 15C is a flowchart illustrating the method of rendering virtual content based on machine learning algorithm incorporated in the processor, in accordance with an embodiment.

FIG. 15C is a flowchart illustrating the method of rendering virtual content based on machine learning algorithm incorporated in the processor 302, in accordance with an embodiment. At step 1528, the machine learning algorithm incorporated in the processor 302 may be configured to learn from activities that had been performed earlier by the user. At step 1530, the processor 302 may determine the type of content that has to be rendered based on the learning. At step 1532, the processor 302 may render at least a portion of the virtual content based on the learning. Such content may include images of one or more participants whom the user may have performed an activity with earlier. At step 1534, the processor 302 may determine whether the portion of the virtual content displayed corresponds to a particular activity. For example, the processor 302 may determine whether the model of the user rendered, corresponds to the participant who might have performed the activity with the user earlier. If the portion of the virtual content displayed does not correspond to the particular activity, then, at step 1536, the processor 302 may request for additional information from user. At step 1538, the processor 302 may render virtual content using the user provided information that may correspond to the activity. If the portion of the virtual content displayed corresponds to the particular activity, then, at step 1540, the processor 302 may provide an option to the user to modify the content. Modifying the content may include adding more participants to the content, removing participants from the content and changing the type of activity, among others. If the user wishes to modify the content, then at step 1542, the processor 302 may receive input from the user to modify or alter the content. At step 1544, the processor 102 may render modified virtual content based on the input received from the user. If the user does not wish to modify the content, then at step 1546, the processor 302 may enable the user to perform the activity and communicate with the one or more users during the activity.

The processor 302 may render virtual content to the user, displaying videos of the participants the user might be willing to participate with. The video data may be integrated with voice data. Alternatively, the processor 302 may generate virtual two or three dimensional models of the participants the user might be willing to participate with. The virtual two or three dimensional models of the participants may be integrated with voice data. Further, the processor 302 may be able to render pre recorded voice data to the virtual two or three dimensional models. The user may be able to communicate with the virtual content displaying presence of the participants the user might be willing to participate with, through voice and text.

The system 300 may be integrated with one or more social networking servers 1204 such as Facebook. The system 300 may enable the users to log in to the social networking portal. The user's profile may be connected or related with a plurality of other users on the portal. The user may be provided an option to communicate with one or more of the plurality of users who may be available or online as seen on the page of the social networking portal. The user may be provided an option to participate with a plurality of users whom the user may prefer to communicate with. Virtual models of one or more of the plurality of users may be rendered and displayed to the user for communication. The communication may happen in the form of voice or text.

In an embodiment, the processor 302 may render virtual two or three dimensional models of random users/people that the user may not know in person. Such random profiles of users whom the user may or may not know in person may be preconfigured by the processor 302 by receiving input from the user. Further, such profiles may be preconfigured profiles of other users by the processor 302 may be created by applying intelligence based on the user's preference, interest and priorities, among others. These preconfigured profiles of random people may be stored in the database 308. Examples of random models may include models of celebrities or animated characters, among other profiles. The processor 302 may be configured to voice attributes among other such attributes to such models. Such random virtual three dimensional models of random participants may be rendered when the user may not be willing to communicate with the users who may be connected with the user or such users may not be available to communicate at that instant.

In one embodiment, for the system 300 to enable the users to participate in an activity and communicate with the user in virtual reality, it may be required that all the other users wear their respective VR devices.

Input such as, tactile and gesture input, data indicating pressure and force vectors, applied through the user's limbs, among others may be received through one or more sensors included in the system 300. The processor 302 may be configured to synthesize the input and determine the visual output or outcome based on the input. The outcome may be applied to the virtual images to alter one or more parameters (location, size etc) of the objects in the virtual images. Gestures along with the semantics of each gesture received through the sensors may be stored in the database 308. The semantics of the gestures may be predefined and stored in the database 308. The database 308 may also store outcomes of such input. The outcomes may indicate one or more physical actions carried by the user which may be applied to the virtual content to modify or alter parameters of the content.

Figure 16A:
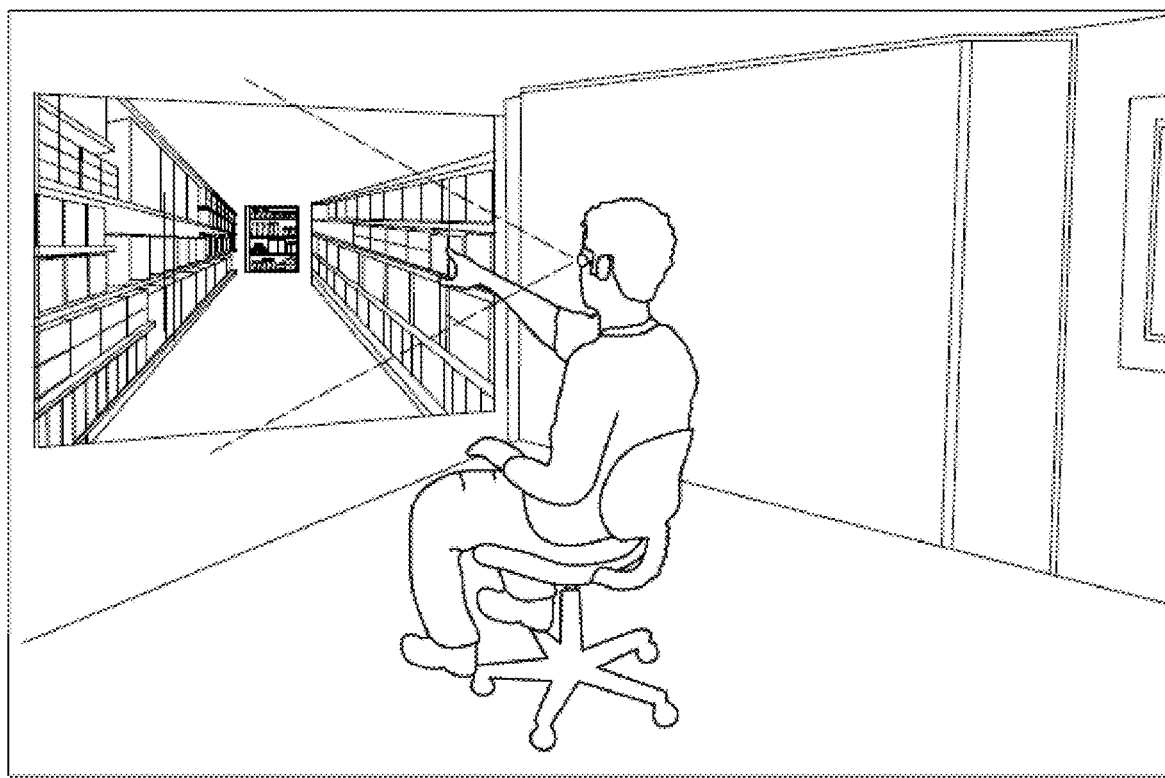
FIGS. 16A and 16B are illustrations of exemplary scenarios wherein virtual content is rendered to a user to provide the user with a shopping experience.
Figure 16B:
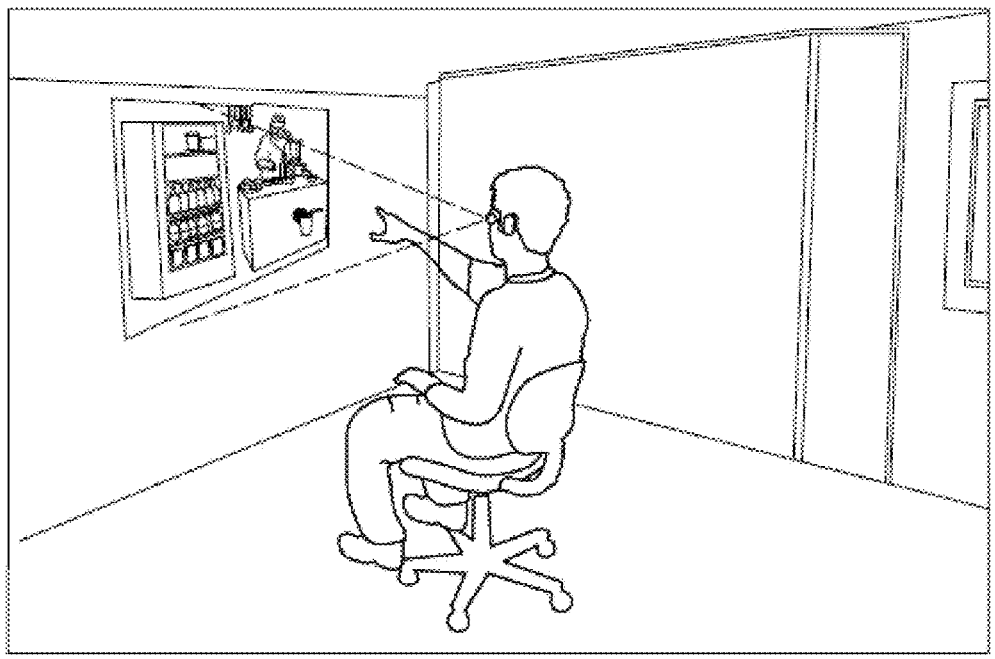

In another exemplary scenario, and referring to FIGS. 16A and 16B, virtual content may be displayed to the user to provide the user with the experience of physically shopping at a location, though the user is indulging in virtual shopping. The system 300 may be able to communicate with one or more remote servers 1204 via the communication module 1202. The servers 1204 may be associated with one or more service providers such as, store websites, online shopping websites and super markets among other service providers. Input may be accepted from the users, through a user interface. The user interface may be portals pertaining to the service providers. Input may include requests to view a shopping location, having at least one store, and displaying the shopping location to the user via the virtual interface of the system 300. The input may be in the form of URLs provided through a virtual browser that may identify a particular service provider's website. The system 300 may provide users with experience of walking beside aisles of the stores, entering the store by opening and walking through its doors, examining the items on the shelves, and placing them into the shopping cart. The gesture of picking up an item and placing it in the shopping cart may be perceived as placing an item in the shopping cart.

The virtual content may be preconfigured or configurable by the service providers. The processor 302 may access the servers 1204 associated with the plurality of service providers and render and display the virtual content to the users. The content may be customized for each user and the customization may be based on the user's profile. The user's profile may include information corresponding to the user's history of purchase, age, gender, location of the user and the user's preferences, among others. The user may create a profile on the portals of the service providers. Alternatively, the servers associated with the service providers may be able to retrieve such information from one or more servers 1204 associated with one or more platforms where the user may have already created a profile. Further, the servers associated with the service providers may be able to retrieve such information corresponding to the user from the processor 302.

In an embodiment, if the user is virtually shopping at a store, the user may request to interact with one or more of the store's shopping assistant while purchasing. The users may post queries and the shopping assistant, who may provide answers to the queries. In addition, the virtual content that may be presented to the users by the service providers may enable the users to learn about the store, its brands, or any other information the store may wish to covey to the user. Further, the users may be able to provide feedback based on their experience.

Alternatively, the users may be assisted by virtual shopping assistants at one or more sections while purchasing. For example, when the user may not be able to decide between two similar items and spends more time browsing at one particular section without placing any item into the shopping cart, the shopping assistant's virtual model may be displayed to the user to assist the user in the purchase. The store keeper may provide reviews and feedbacks of other customers to the user and help the user make the purchase.

In another embodiment, virtual assistance may be rendered into virtual reality by means of one or more among text and voice as opposed to virtual models of shopping assistants providing assistance.

In an embodiment, virtual content for an online shopping website may be pre configured or configurable by the service provider. The processor 302 may access the servers associated with a plurality of service providers and render and display the virtual content to the users. The user may request for the shopping assistant to assist him/her with the purchase. For example, if the user is shopping for apparels, he/she may request virtual assistance from a stylist or may request for the specifications of the product. If the user is purchasing a book, the user may scan through the cover and request for reviews. Reviews provided by other users may be displayed in virtual reality. Virtual assistance may also be rendered into virtual reality by means of one or more among text and voice as opposed to virtual models of random people.

In an embodiment, all information corresponding to a particular product may be rendered and displayed as soon as the user selects the product or places it into the shopping cart, in virtual reality. Information may include all reviews provided by users from across the world, specification of a particular product and a comparison chart between two or more similar products among others may be rendered to the user in virtual reality. Such information may appear as texts. Such information may be presented by random models of users who may have purchased the product earlier or who may be associated with the product through audio output. Further such information may be presented as one or more among texts and voices.

In an embodiment, virtual assistance may be provided to the user based on the user's profile and purchase history, among others. Alternatively, the users may be provided with options to select assistance whenever the user might require assistance.

Figure 16C:
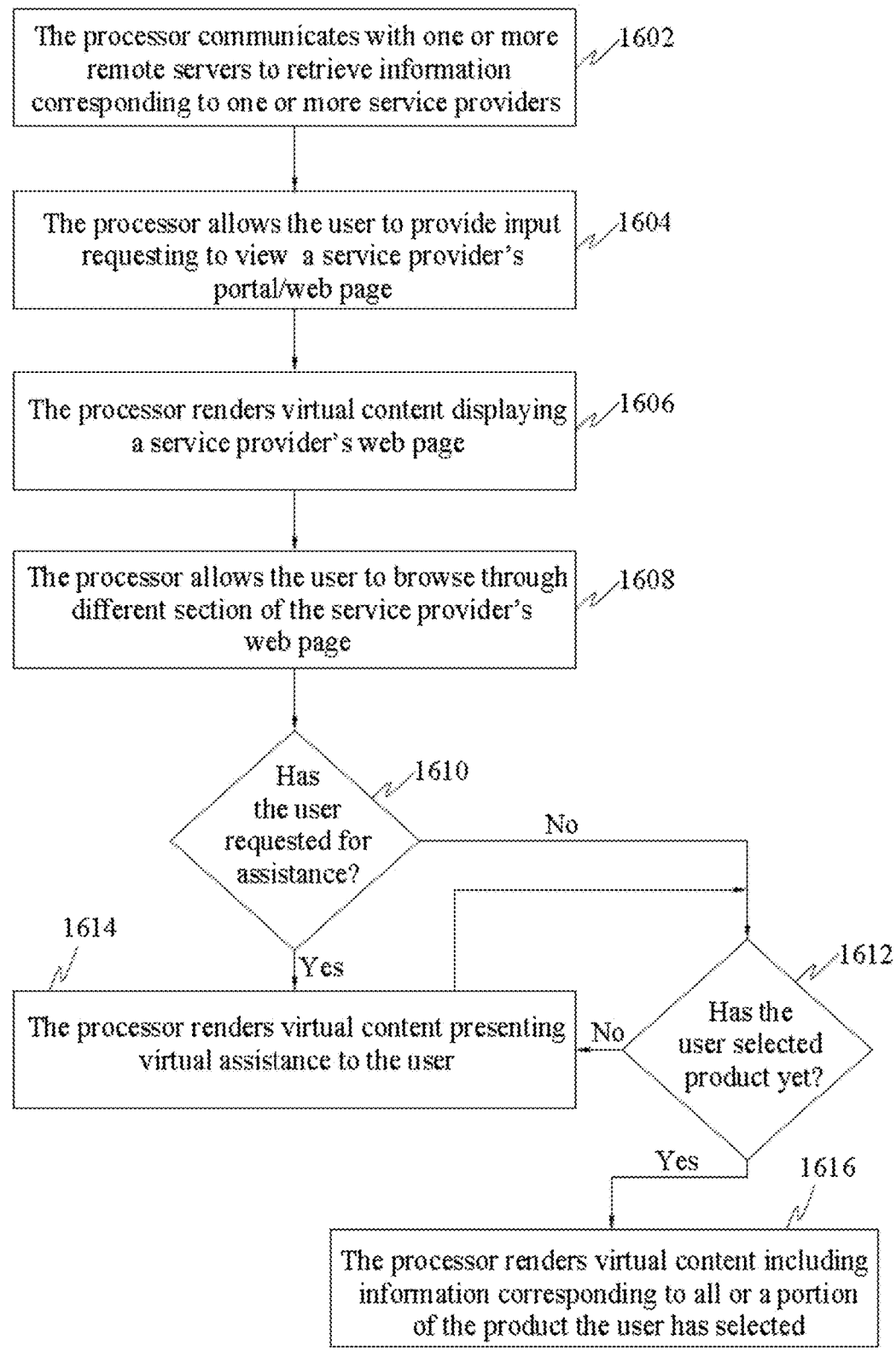
FIG. 16C is a flowchart illustrating the method of rendering virtual content to the user to enable the user to shop online or at virtual stores, in accordance with an embodiment.

FIG. 16C is a flowchart illustrating the method of rendering virtual content to the user to enable the user to shop online or at stores, in accordance with an embodiment. At step 1602, the processor 302 may communicate with one or more remote servers to retrieve information corresponding to one or more service providers. At step 1604, the processor 302 may allow the user to provide input requesting to view a service provider's portal/webpage. At step 1606, the processor 302 may render virtual content displaying a service provider's webpage. At step 1608, the processor 302 may allow the user to browse through different sections of the service provider's webpage. At step 1610, the processor 302 may determine if the user has requested for assistance to make a purchase. If the user has not requested assistance, then the processor 302, at step 1612, determines whether the user has selected any product. If the processor 302 determines that the user has requested for assistance to make a purchase, then at step 1614 the processor 302 may render virtual content presenting virtual assistance to the user. After step 1614 has been executed, the processor 302 may execute step 1612 again until the processor determines that the user has made a selection at step 1612. If the processor 302 determines that the user has made a selection, then, the processor 302, at step 1616 may render virtual content including information corresponding to all or a portion of the products the user has selected.

In an embodiment, the user may be provided an option to proceed with payment after making selection. The user may also be assisted during the payment. Virtual assistance may be provided to the user to select a payment method and accordingly proceed with the steps of payment. Such virtual assistance may be in the form of voice or text or virtual models may be presented to assist the user.

In another embodiment, the system 300 may be integrated with an application module that may be implemented for the purpose of enabling the user to shop online or at physical stores virtually in a two or three dimensional virtual reality interface. The user may be required to log into the application module and browse for shops or products or categories of products through the virtual interface.

In some embodiments, one or more of users participating in the activities in all the above examples may have cameras or any image or video capturing devices integrated with their respective VR devices. Images, photos, videos or live webcam feeds of the users may be communicated to the other users whom they are participating and communicating with.

In an embodiment, the users may communicate with one another in virtual reality via voice communication modules. The users may also communicate with other users using voice data through a telephone module. The users may be enabled to provide voice data through a microphone and receive voice data from other users through headphones or speakers.

In an embodiment, the rendering module 304 may render enlarged lifesize views of three-dimensional content on display surfaces such as walls, floor, ceiling and table surfaces among others.

In an embodiment, live feeds from one or more servers 1204 may be received and processed by the processor 302 in near real time to generate the virtual content.

The system can be used in industrial applications, for example in repair/maintenance augmentation. One exemplary pseudo-code is Repair Augmentation
User selects AR assisted repair mode,
System identifies surface and components mounted thereon
  System looks up repair sequence:
  determines type of component, location of component,
  identifies or highlights on the HUD each component to be opened or removed and provides instructions on removal techniques,
    wait until each component is opened or removed and then show next component until done
    accesses the target component to replace or repair and show instructions to repair or replace,
    sequentially shows instructions to put back components previously opened or removed.

In one example, the AR interface may overlay the objects observed on the sorting surface with highlight in which the various objects are outlined in different colors: e.g. PET as red, PVC, as blue, PE as green, and polycarbonate as purple. Additional information may include compositional information appearing as text or additional coding in the AR interface. In one system, the criticality associated with each object may be indicated by the brightness of the outline color; more vivid colors may indicate that high attention should be paid to the object. Alternatively, object criticality may be displayed in terms of the jaggedness of outlined shapes in which more jagged outlines indicate lesser criticality. In yet another alternative example, the function of the object may be displayed as text superimposed on the object image.

In another implementation, objects may be presented to the illumination and sensors so that their content may be analyzed and their placement on the repair surface may be determined by the computing system. The computing system may then supply augmented reality data streams to the AR interface users to inform them of the composition of each of the sortable objects.

In one embodiment for sorting a stream of small objects, a sorting machine can have a number of lanes on a moving sorting surface, each lane containing objects having the same composition. For example, as the sorting surface moves between a group of sorters, the sorters may simply push the objects into a specific lane based on composition. The AR system can color code each object to be sorted into a particular lane. At the end of the moving surface, a sorter may have pre-arranged bins placed to receive the objects from each lane as they fall off the surface into the appropriate bin. The AR system can provide sensors such as spectral sensors for a majority determination of composition. In the event that an object does not have a consistent spectral response, information may be presented over the AR interface to a sorter, letting him or her know that the object should be set aside for further consideration. The computing system may provide a group of sorters, using augmented reality interfaces, with information regarding how to bin each object. The sorters may continue to place objects by composition into appropriate bins until the bins become full. In one configuration, a sorter may then stop sorting and move the bin to a shipping location. During the time the sorter is away from his or her position by the sorting surface, the sorter may notify a facility operator of this break in the sorting process over a voice transmitting channel associated with the AR interface. Alternatively, another facility worker may move the bin to a post-processing station (such as a station to box the items for shipping to another facility). If the post-processing station becomes overburdened due to a large amount of material to ship out, the post-processing worker may notify the facility operator over an AR interface voice channel that the sorting process for that particular material should be delayed. In either alternative, the facility operator may then direct the computing system to slow the travel of the moving sorting surface or even stop it entirely. In this manner, the sorting process may be adapted to changes in the work flow.

Figure 17A:
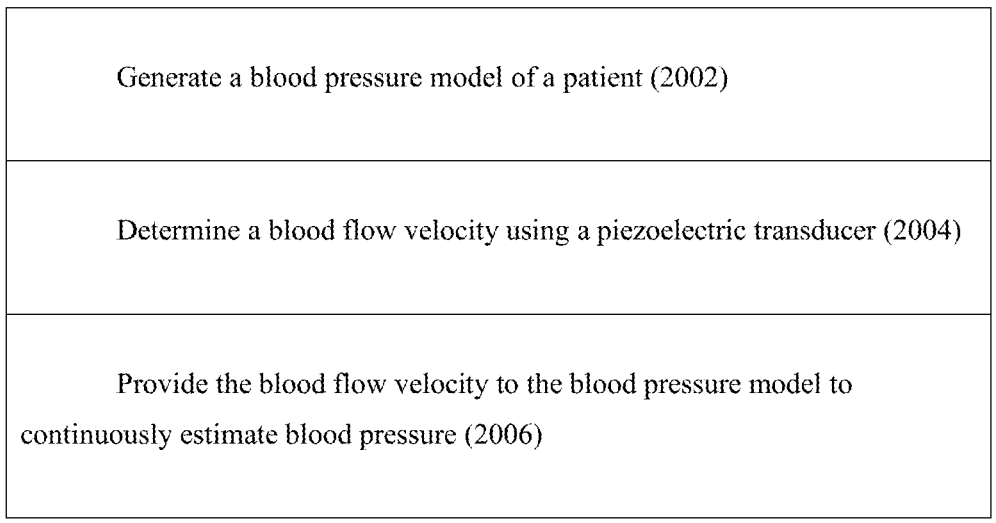
FIGS. 17A to 17B shows exemplary processes to estimate blood pressure for the system of FIG. 2D.
Figure 17B:
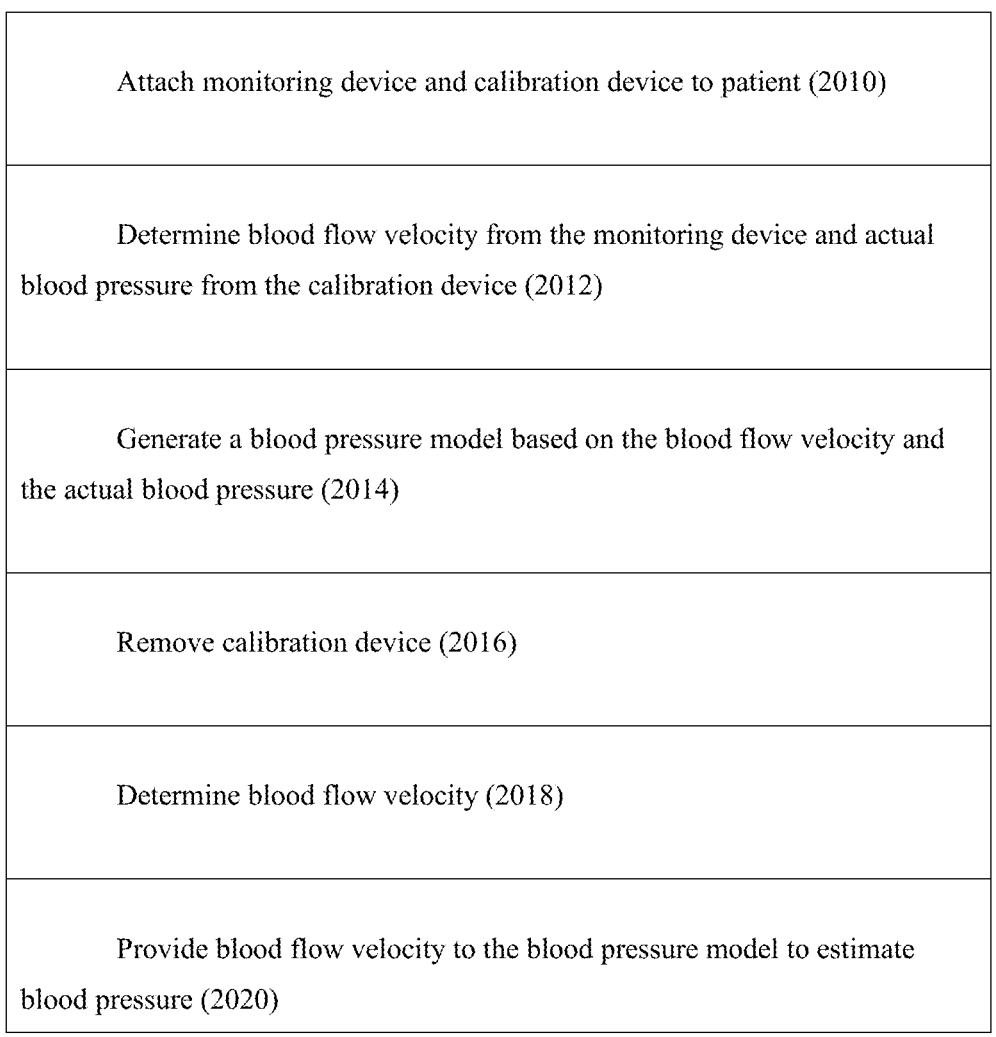

FIG. 17A shows ant exemplary process to continuously determine blood pressure of a patient. The process generates a blood pressure model of a patient (2002); determines a blood flow velocity using a piezoelectric transducer (2004); and provides the blood flow velocity to the blood pressure model to continuously estimate blood pressure (2006). FIG. 17B shows another exemplary process to continuously determine blood pressure of a patient. First, during an initialization mode, a monitoring device and calibration device are attached to patient (2010). The monitoring device generates patient blood flow velocity, while actual blood pressure is measured by a calibration device (2012). Next, the process generates a blood pressure model based on the blood flow velocity and the actual blood pressure (2014). Once this is done, the calibration device can be removed (2016). Next, during an operation mode, the process periodically samples blood flow velocity from the monitoring device on a real-time basis (18) and provides the blood flow velocity as input information to the blood pressure model to estimate blood pressure (20). This process can be done in continuously or periodically as specified by a user.

In one embodiment, to determine blood flow velocity, acoustic pulses are generated and transmitted into the artery using an ultrasonic transducer positioned near a wrist artery. These pulses are reflected by various structures or entities within the artery (such as the artery walls, and the red blood cells within the subject's blood), and subsequently received as frequency shifts by the ultrasonic transducer. Next, the blood flow velocity is determined. In this process, the frequencies of those echoes reflected by blood cells within the blood flowing in the artery differ from that of the transmitted acoustic pulses due to the motion of the blood cells. This well known "Doppler shift" in frequency is used to calculate the blood flow velocity. In one embodiment for determining blood flow velocity, the Doppler frequency is used to determine mean blood velocity. For example, U.S. Pat. No. 6,514,211, the content of which is incorporated by reference, discusses blood flow velocity using a time-frequency representation.

In one implementation, the system can obtain one or more numerical calibration curves describing the patient's vital signs such as blood pressure. The system can then direct energy such as infrared or ultrasound at the patient's artery and detecting reflections thereof to determine blood flow velocity from the detected reflections. The system can numerically fit or map the blood flow velocity to one or more calibration parameters describing a vital-sign value. The calibration parameters can then be compared with one or more numerical calibration curves to determine the blood pressure.

Additionally, the system can analyze blood pressure, and heart rate, and pulse oximetry values to characterize the user's cardiac condition. These programs, for example, may provide a report that features statistical analysis of these data to determine averages, data displayed in a graphical format, trends, and comparisons to doctor-recommended values.

In one embodiment, feed forward artificial neural networks (NNs) are used to classify valve-related heart disorders. The heart sounds are captured using the microphone or piezoelectric transducer. Relevant features were extracted using several signal processing tools, discrete wavelet transfer, fast fourier transform, and linear prediction coding. The heart beat sounds are processed to extract the necessary features by: a) denoising using wavelet analysis, b) separating one beat out of each record c) identifying each of the first heart sound (FHS) and the second heart sound (SHS). Valve problems are classified according to the time separation between the FHS and th SHS relative to cardiac cycle time, namely whether it is greater or smaller than 20% of cardiac cycle time. In one embodiment, the NN comprises 6 nodes at both ends, with one hidden layer containing 10 nodes. In another embodiment, linear predictive code (LPC) coefficients for each event were fed to two separate neural networks containing hidden neurons.

In another embodiment, a normalized energy spectrum of the sound data is obtained by applying a Fast Fourier Transform. The various spectral resolutions and frequency ranges were used as inputs into the NN to optimize these parameters to obtain the most favorable results.

In another embodiment, the heart sounds are denoised using six-stage wavelet decomposition, thresholding, and then reconstruction. Three feature extraction techniques were used: the Decimation method, and the wavelet method. Classification of the heart diseases is done using Hidden Markov Models (HMMs).

In yet another embodiment, a wavelet transform is applied to a window of two periods of heart sounds. Two analyses are realized for the signals in the window: segmentation of first and second heart sounds, and the extraction of the features. After segmentation, feature vectors are formed by using he wavelet detail coefficients at the sixth decomposition level. The best feature elements are analyzed by using dynamic programming.

In another embodiment, the wavelet decomposition and reconstruction method extract features from the heart sound recordings. An artificial neural network classification method classifies the heart sound signals into physiological and pathological murmurs. The heart sounds are segmented into four parts: the first heart sound, the systolic period, the second heart sound, and the diastolic period. The following features can be extracted and used in the classification algorithm: a) Peak intensity, peak timing, and the duration of the first heart sound b) the duration of the second heart sound c) peak intensity of the aortic component of S2(A2) and the pulmonic component of S2 (P2), the splitting interval and the reverse flag of A2 and P2, and the timing of A2 d) the duration, the three largest frequency components of the systolic signal and the shape of the envelope of systolic murmur e) the duration the three largest frequency components of the diastolic signal and the shape of the envelope of the diastolic murmur.

In one embodiment, the time intervals between the ECG R-waves are detected using an envelope detection process. The intervals between R and T waves are also determined. The Fourier transform is applied to the sound to detect S1 and S2. To expedite processing, the system applies Fourier transform to detect S1 in the interval 0.1-0.5 R-R. The system looks for S2 the intervals R-T and 0.6 R-R. S2 has an aortic component A2 and a pulmonary component P2. The interval between these two components and its changes with respiration has clinical significance. A2 sound occurs before P2, and the intensity of each component depends on the closing pressure and hence A2 is louder than P2. The third heard sound S3 results from the sudden halt in the movement of the ventricle in response to filling in early diastole after the AV valves and is normally observed in children and young adults. The fourth heart sound S4 is caused by the sudden halt of the ventricle in response to filling in presystole due to atrial contraction.

In yet another embodiment, the S2 is identified and a normalized splitting interval between A2 and P2 is determined. If there is no overlap, A2 and P2 are determined from the heart sound. When overlap exists between A2 and P2, the sound is dechirped for identification and extraction of A2 and P2 from S2. The A2-P2 splitting interval (SI) is calculated by computing the cross-correlation function between A2 and P2 and measuring the time of occurrence of its maximum amplitude. SI is then normalized (NSI) for heart rate as follows: NSI=SI/cardiac cycle time. The duration of the cardiac cycle can be the average interval of QRS waves of the ECG. It could also be estimated by computing the mean interval between a series of consecutive S1 and S2 from the heart sound data. A non linear regressive analysis maps the relationship between the normalized NSI and PAP. A mapping process such as a curve-fitting procedure determines the curve that provides the best fit with the patient data. Once the mathematical relationship is determined, NSI can be used to provide an accurate quantitative estimate of the systolic and mean PAP relatively independent of heart rate and systemic arterial pressure.

In another embodiment, the first heart sound (S1) is detected using a time-delayed neural network (TDNN). The network consists of a single hidden layer, with time-delayed links connecting the hidden units to the time-frequency energy coefficients of a Morlet wavelet decomposition of the input phonocardiogram (PCG) signal. The neural network operates on a 200 msec sliding window with each time-delay hidden unit spanning 100 msec of wavelet data.

In yet another embodiment, a local signal analysis is used with a classifier to detect, characterize, and interpret sounds corresponding to symptoms important for cardiac diagnosis. The system detects a plurality of different heart conditions. Heart sounds are automatically segmented into a segment of a single heart beat cycle. Each segment are then transformed using 7 level wavelet decomposition, based on Coifian 4th order wavelet kernel. The resulting vectors 4096 values, are reduced to 256 element feature vectors, this simplified the neural network and reduced noise.

In another embodiment, feature vectors are formed by using the wavelet detail and approximation coefficients at the second and sixth decomposition levels. The classification (decision making) is performed in 4 steps: segmentation of the first and second heart sounds, normalization process, feature extraction, and classification by the artificial neural network.

In another embodiment using decision trees, the system distinguishes (1) the Aortic Stenosis (AS) from the Mitral Regurgitation (MR) and (2) the Opening Snap (OS), the Second Heart Sound Split (A2_P2) and the Third Heart Sound (S3). The heart sound signals are processed to detect the first and second heart sounds in the following steps: a) wavelet decomposition, b) calculation of normalized average Shannon Energy, c) a morphological transform action that amplifies the sharp peaks and attenuates the broad ones d) a method that selects and recovers the peaks corresponding to S1 and S2 and rejects others e) algorithm that determines the boundaries of S1 and S2 in each heart cycle f) a method that distinguishes S1 from S2.

In one embodiment, once the heart sound signal has been digitized and captured into the memory, the digitized heart sound signal is parameterized into acoustic features by a feature extractor. The output of the feature extractor is delivered to a sound recognizer. The feature extractor can include the short time energy, the zero crossing rates, the level crossing rates, the filter-bank spectrum, the linear predictive coding (LPC), and the fractal method of analysis. In addition, vector quantization may be utilized in combination with any representation techniques. Further, one skilled in the art may use an auditory signal-processing model in place of the spectral models to enhance the system's robustness to noise and reverberation.

In one embodiment of the feature extractor, the digitized heart sound signal series s(n) is put through a low-order filter, typically a first-order finite impulse response filter, to spectrally flatten the signal and to make the signal less susceptible to finite precision effects encountered later in the signal processing. The signal is pre-emphasized preferably using a fixed pre-emphasis network, or preemphasizer. The signal can also be passed through a slowly adaptive pre-emphasizer. The preemphasized heart sound signal is next presented to a frame blocker to be blocked into frames of N samples with adjacent frames being separated by M samples. In one implementation, frame 1 contains the first 400 samples. The frame 2 also contains 400 samples, but begins at the 300th sample and continues until the 700th sample. Because the adjacent frames overlap, the resulting LPC spectral analysis will be correlated from frame to frame. Each frame is windowed to minimize signal discontinuities at the beginning and end of each frame. The windower tapers the signal to zero at the beginning and end of each frame. Preferably, the window used for the autocorrelation method of LPC is the Hamming window. A noise canceller operates in conjunction with the autocorrelator to minimize noise. Noise in the heart sound pattern is estimated during quiet periods, and the temporally stationary noise sources are damped by means of spectral subtraction, where the autocorrelation of a clean heart sound signal is obtained by subtracting the autocorrelation of noise from that of corrupted heart sound. In the noise cancellation unit, if the energy of the current frame exceeds a reference threshold level, the heart is generating sound and the autocorrelation of coefficients representing noise is not updated. However, if the energy of the current frame is below the reference threshold level, the effect of noise on the correlation coefficients is subtracted off in the spectral domain. The result is half-wave rectified with proper threshold setting and then converted to the desired autocorrelation coefficients. The output of the autocorrelator and the noise canceller are presented to one or more parameterization units, including an LPC parameter unit, an FFT parameter unit, an auditory model parameter unit, a fractal parameter unit, or a wavelet parameter unit, among others. The LPC parameter is then converted into cepstral coefficients. The cepstral coefficients are the coefficients of the Fourier transform representation of the log magnitude spectrum. A filter bank spectral analysis, which uses the short-time Fourier transformation (STFT) may be used alone or in conjunction with other parameter blocks. FFT is well known in the art of digital signal processing. Such a transform converts a time domain signal, measured as amplitude over time, into a frequency domain spectrum, which expresses the frequency content of the time domain signal as a number of different frequency bands. The FFT thus produces a vector of values corresponding to the energy amplitude in each of the frequency bands. The FFT converts the energy amplitude values into a logarithmic value which reduces subsequent computation since the logarithmic values are more simple to perform calculations on than the longer linear energy amplitude values produced by the FFT, while representing the same dynamic range. Ways for improving logarithmic conversions are well known in the art, one of the simplest being use of a look-up table. In addition, the FFT modifies its output to simplify computations based on the amplitude of a given frame. This modification is made by deriving an average value of the logarithms of the amplitudes for all bands. This average value is then subtracted from each of a predetermined group of logarithms, representative of a predetermined group of frequencies. The predetermined group consists of the logarithmic values, representing each of the frequency bands. Thus, utterances are converted from acoustic data to a sequence of vectors of k dimensions, each sequence of vectors identified as an acoustic frame, each frame represents a portion of the utterance. Alternatively, auditory modeling parameter unit can be used alone or in conjunction with others to improve the parameterization of heart sound signals in noisy and reverberant environments. In this approach, the filtering section may be represented by a plurality of filters equally spaced on a log-frequency scale from 0 Hz to about 3000 Hz and having a prescribed response corresponding to the cochlea. The nerve fiber firing mechanism is simulated by a multilevel crossing detector at the output of each cochlear filter. The ensemble of the multilevel crossing intervals corresponding to the firing activity at the auditory nerve fiber-array. The interval between each successive pair of same direction, either positive or negative going, crossings of each predetermined sound intensity level is determined and a count of the inverse of these interspike intervals of the multilevel detectors for each spectral portion is stored as a function of frequency. The resulting histogram of the ensemble of inverse interspike intervals forms a spectral pattern that is representative of the spectral distribution of the auditory neural response to the input sound and is relatively insensitive to noise. The use of a plurality of logarithmically related sound intensity levels accounts for the intensity of the input signal in a particular frequency range. Thus, a signal of a particular frequency having high intensity peaks results in a much larger count for that frequency than a low intensity signal of the same frequency. The multiple level histograms of the type described herein readily indicate the intensity levels of the nerve firing spectral distribution and cancel noise effects in the individual intensity level histograms. Alternatively, the fractal parameter block can further be used alone or in conjunction with others to represent spectral information. Fractals have the property of self-similarity as the spatial scale is changed over many orders of magnitude. A fractal function includes both the basic form inherent in a shape and the statistical or random properties of the replacement of that shape in space. As is known in the art, a fractal generator employs mathematical operations known as local affine transformations. These transformations are employed in the process of encoding digital data representing spectral data. The encoded output constitutes a "fractal transform" of the spectral data and consists of coefficients of the affine transformations. Different fractal transforms correspond to different images or sounds.

Alternatively, a wavelet parameterization block can be used alone or in conjunction with others to generate the parameters. Like the FFT, the discrete wavelet transform (DWT) can be viewed as a rotation in function space, from the input space, or time domain, to a different domain. The DWT consists of applying a wavelet coefficient matrix hierarchically, first to the full data vector of length N, then to a smooth vector of length N/2, then to the smooth-smooth vector of length N/4, and so on. Most of the usefulness of wavelets rests on the fact that wavelet transforms can usefully be severely truncated, or turned into sparse expansions. In the DWT parameterization block, the wavelet transform of the heart sound signal is performed. The wavelet coefficients are allocated in a non-uniform, optimized manner. In general, large wavelet coefficients are quantized accurately, while small coefficients are quantized coarsely or even truncated completely to achieve the parameterization. Due to the sensitivity of the low-order cepstral coefficients to the overall spectral slope and the sensitivity of the high-order cepstral coefficients to noise variations, the parameters generated may be weighted by a parameter weighing block, which is a tapered window, so as to minimize these sensitivities. Next, a temporal derivator measures the dynamic changes in the spectra. Power features are also generated to enable the system to distinguish heart sound from silence.

After the feature extraction has been performed, the heart sound parameters are next assembled into a multidimensional vector and a large collection of such feature signal vectors can be used to generate a much smaller set of vector quantized (VQ) feature signals by a vector quantizer that cover the range of the larger collection. In addition to reducing the storage space, the VQ representation simplifies the computation for determining the similarity of spectral analysis vectors and reduces the similarity computation to a look-up table of similarities between pairs of codebook vectors. To reduce the quantization error and to increase the dynamic range and the precision of the vector quantizer, the preferred embodiment partitions the feature parameters into separate codebooks, preferably three. In the preferred embodiment, the first, second and third codebooks correspond to the cepstral coefficients, the differenced cepstral coefficients, and the differenced power coefficients.

With conventional vector quantization, an input vector is represented by the codeword closest to the input vector in terms of distortion. In conventional set theory, an object either belongs to or does not belong to a set. This is in contrast to fuzzy sets where the membership of an object to a set is not so clearly defined so that the object can be a part member of a set. Data are assigned to fuzzy sets based upon the degree of membership therein, which ranges from 0 (no membership) to 1.0 (full membership). A fuzzy set theory uses membership functions to determine the fuzzy set or sets to which a particular data value belongs and its degree of membership therein.

To handle the variance of heart sound patterns of individuals over time and to perform speaker adaptation in an automatic, self-organizing manner, an adaptive clustering technique called hierarchical spectral clustering is used. Such speaker changes can result from temporary or permanent changes in vocal tract characteristics or from environmental effects. Thus, the codebook performance is improved by collecting heart sound patterns over a long period of time to account for natural variations in speaker behavior. In one embodiment, data from the vector quantizer is presented to one or more recognition models, including an HMM model, a dynamic time warping model, a neural network, a fuzzy logic, or a template matcher, among others. These models may be used singly or in combination.

In dynamic processing, at the time of recognition, dynamic programming slides, or expands and contracts, an operating region, or window, relative to the frames of heart sound so as to align those frames with the node models of each S1-S4 pattern to find a relatively optimal time alignment between those frames and those nodes. The dynamic processing in effect calculates the probability that a given sequence of frames matches a given word model as a function of how well each such frame matches the node model with which it has been time-aligned. The word model which has the highest probability score is selected as corresponding to the heart sound.

Dynamic programming obtains a relatively optimal time alignment between the heart sound to be recognized and the nodes of each word model, which compensates for the unavoidable differences in speaking rates which occur in different utterances of the same word. In addition, since dynamic programming scores words as a function of the fit between word models and the heart sound over many frames, it usually gives the correct word the best score, even if the word has been slightly misspoken or obscured by background sound. This is important, because humans often mispronounce words either by deleting or mispronouncing proper sounds, or by inserting sounds which do not belong.

In dynamic time warping (DTW), the input heart sound A, defined as the sampled time values $A=a(1) \ldots a(n)$, and the vocabulary candidate B, defined as the sampled time values $B=b(1) \ldots b(n)$, are matched up to minimize the discrepancy in each matched pair of samples. Computing the warping function can be viewed as the process of finding the minimum cost path from the beginning to the end of the words, where the cost is a function of the discrepancy between the corresponding points of the two words to be compared. Dynamic programming considers all possible points within the permitted domain for each value of i. Because the best path from the current point to the next point is independent of what happens beyond that point. Thus, the total cost of $[i(k), j(k)]$ is the cost of the point itself plus the cost of the minimum path to it. Preferably, the values of the predecessors can be kept in an M×N array, and the accumulated cost kept in a 2.times.N array to contain the accumulated costs of the immediately preceding column and the current column. However, this method requires significant computing resources. For the heart sound recognizer to find the optimal time alignment between a sequence of frames and a sequence of node models, it must compare most frames against a plurality of node models. One method of reducing the amount of computation required for dynamic programming is to use pruning. Pruning terminates the dynamic programming of a given portion of heart sound against a given word model if the partial probability score for that comparison drops below a given threshold. This greatly reduces computation, since the dynamic programming of a given portion of heart sound against most words produces poor dynamic programming scores rather quickly, enabling most words to be pruned after only a small percent of their comparison has been performed. To reduce the computations involved, one embodiment limits the search to that within a legal path of the warping.

A Hidden Markov model can be used in one embodiment to evaluate the probability of occurrence of a sequence of observations O(1), O(2), . . . O(t), . . . , O(T), where each observation O(t) may be either a discrete symbol under the VQ approach or a continuous vector. The sequence of observations may be modeled as a probabilistic function of an underlying Markov chain having state transitions that are not directly observable. The transitions between states are represented by a transition matrix A=[a(i,j)]. Each a(i,j) term of the transition matrix is the probability of making a transition to state j given that the model is in state i. The output symbol probability of the model is represented by a set of functions B=[b(j)(O(t)], where the b(j)(O(t) term of the output symbol matrix is the probability of outputting observation O(t), given that the model is in state j. The first state is always constrained to be the initial state for the first time frame of the utterance, as only a prescribed set of left-to-right state transitions are possible. A predetermined final state is defined from which transitions to other states cannot occur. Transitions are restricted to reentry of a state or entry to one of the next two states. Such transitions are defined in the model as transition probabilities. For example, a heart sound pattern currently having a frame of feature signals in state 2 has a probability of reentering state 2 of a(2,2), a probability a(2,3) of entering state 3 and a probability of a(2,4)=1−a(2, 1)−a(2,2) of entering state 4. The probability a(2, 1) of entering state 1 or the probability a(2,5) of entering state 5 is zero and the sum of the probabilities a(2,1) through a(2,5) is one. Although the preferred embodiment restricts the flow graphs to the present state or to the next two states, one skilled in the art can build an HMM model without any transition restrictions.

The Markov model is formed for a reference pattern from a plurality of sequences of training patterns and the output symbol probabilities are multivariate Gaussian function probability densities. The heart sound traverses through the feature extractor. During learning, the resulting feature vector series is processed by a parameter estimator, whose output is provided to the hidden Markov model. The hidden Markov model is used to derive a set of reference pattern templates, each template representative of an identified S1-S4 pattern in a vocabulary set of reference patterns. The Markov model reference templates are next utilized to classify a sequence of observations into one of the reference patterns based on the probability of generating the observations from each Markov model reference pattern template. During recognition, the unknown pattern can then be identified as the reference pattern with the highest probability in the likelihood calculator.

FIG. 18A shows an exemplary AR surgical system 3000. The system may include a processor 3090, a memory device 3092, and mass storage device 3093. The computing device is communicatively coupled with a display device 3094. The AR display device 3094 may be a body mounted display such as a heads-up display or a glass mounted in an AR system such as that of FIG. 1, or an additional display device may be positioned away from the computing device. For example, the display device 3094 may be positioned upon the ceiling or wall of the operating room wherein the orthopaedic surgical procedure is to be performed. Additionally or alternatively, the display device 3094 may include a virtual display such as a holographic display and/or other types of displays. The computing device may be communicatively coupled to one or more camera units. The system 3000 may also include sensors or reference arrays 3104 which may be coupled to relevant bones of a patient 3106 and/or with orthopaedic surgical tools 3108. For example, a tibial array can be used that includes a reference array and bone clamp. The bone clamp may be coupled with a tibia bone of the patient using a Schantz pin, but other types of bone clamps may be used. The reference array may be coupled with the bone clamp via an extension arm. The reference array may include a frame and three reflective elements. The reflective elements in one embodiment are spherical, but may have other geometric shapes. Additionally, in other embodiments sensor arrays having more than three reflective elements may be used. The reflective elements may be positioned in a predefined configuration that enables the computing device to determine the identity of the tibial array based on the configuration. That is, when the tibial array is positioned in a field of view of the camera head, the computing device may determine the identity of the tibial array based on the images received from the camera head. Additionally, based on the relative position of the reflective elements, the computing device may determine the location and orientation of the tibial array and, accordingly, the tibia to which the array is coupled.

Reference arrays may also be coupled to other surgical tools. For example, a registration tool may be used to register points of a bone. The registration tool may include a sensor array having reflective elements coupled with a handle of the tool. The registration tool may also include a pointer end that is used to register points of a bone. The reflective elements may be positioned in a configuration that enables the computing device to determine the identity of the registration tool and its relative location (i.e., the location of the pointer end). Additionally, reference arrays may be used on other surgical tools such as a tibial resection jig. The jig may include a resection guide portion that is coupled with a tibia bone at a location of the bone that is to be resected. The jig may include a reference array that is coupled with the portion via a frame. The reference array 146 may include three reflective elements 148 that may be positioned in a configuration that enables the computing device to determine the identity of the jig and its relative location (e.g., with respect to the tibia bone).

During the performance of the orthopaedic surgical procedure, a custom surgical plan may include one or more instructions that program or otherwise configure the HUD to display images of the individual surgical procedure steps which form the orthopaedic surgical procedure being performed. The images may be graphically rendered images or graphically enhanced photographic images. For example, the images may include three dimensional rendered images of the relevant anatomical portions of a patient. The surgeon may interact with the computing device to display the images of the various surgical steps in sequential order. In addition, the surgeon may interact with the computing device to view previously displayed images of surgical steps, selectively view images, instruct the computing device to render the anatomical result of a proposed surgical step or procedure, or perform other surgical related functions. For example, the surgeon may view rendered images of the resulting bone structure of different bone resection procedures. In this way, the custom surgical plan may configure the system 3000 to provide a surgical "walk-through" customized to the patient 106 that the surgeon may follow while performing the surgical procedure.

In one embodiment, the custom surgical plan may include an ordered selection of instructional images that depict individual surgical steps that make up at least a portion of the orthopaedic surgical procedure to be performed. The instructional images may include images of surgical tools and associated text information, graphically rendered images of surgical tools and relevant patient anatomy, and/or other images and/or text information that assist the surgeon during the surgical procedure. The instructional images may be stored in an electronic library, which may be embodied as, for example, a database, a file folder or storage location containing separate instructional images and an associated look-up table, hard-coded information. The surgical plan may include among other things an ordered selection of instructional images that are displayed to the surgeon via the display device 3094 such that the instructional images provide a surgical "walk-through" of the procedure or portion thereof. The surgical plan may also include a number of surgical sub-step images, some of which may or may not be displayed to and performed by the surgeon based on selections chosen by the surgeon during the performance of the orthopaedic surgical procedure.

In some embodiments, the surgeon may also interact with the computing device to control various devices of the system 3000. For example, the surgeon may interact with the system 3000 to control user preferences or settings of the AR display device 3094. Further, the computing device may prompt the surgeon for responses. For example, the computing device 62 may prompt the surgeon to inquire if the surgeon has completed the current surgical step, if the surgeon would like to view other images, and/or other surgical procedure inquiries.

The AR system may be used to generate pre-operative orthopaedic surgical plans, surgical notes created during an orthopaedic surgery, medical images of a patient's bone (and soft tissue) and/or orthopaedic implants coupled thereto, and/or other data. Such data generated via the system 3000 may be stored in the database by, for example, transmitting the data from the system 3000 to the database via the network. Additionally, other medical devices typically found in a hospital or other healthcare facility may be used to generate medical images of a bone (and, in some embodiments, soft tissue) of the patient. Such medical images may also be stored in the database. The medical images may be embodied as any type of medical image providing a visual indication of a relevant bone or bones (and soft tissue if desired) of a patient. For example, the medical images may be embodied as any number of X-ray images, magnetic resonance imaging (MRI) images, computerized tomography (CT) images, or the like. Regardless, such medical images may be stored in the database 28 along with associated data relevant to the particular medical images. Such associated data may include, but is not limited to, the patient's name and other patient identification information, date of the images, surgeon's or doctor's name, the name of the hospital or healthcare facility wherein the medical images were generated, and the like.

In operation, the system can receive a request for surgical plans for a patient, may generate a surgical plan that has been customized for the patient, and may provide the custom surgical plan for the patient to the healthcare facility.

The surgical plan request data may include any data relevant to the surgical plan being requested, any data related to the orthopaedic surgical procedure to be performed, any data related to the patient on which the orthopaedic surgical procedure to be performed, and/or any other data useful for customizing the orthopaedic surgical procedure to the patient. For example, the request data may include, but is not limited to, the type of orthopaedic surgical procedure to be performed, the type of orthopaedic implant to be used, rendered images of the relevant anatomical portions of the patient, digital templates of the orthopaedic implants and/or planned resection lines, pre-operative notes, diagrams, historic patient data, X-rays, medical images, patient medical records, patient identification data, and/or any other data useful for customizing the orthopaedic surgical procedure to the patient.

In creating the surgical plan, the surgical plan system may perform a digital templating procedure on medical images of the surgical plan request to determine an orthopaedic implant to recommend to the surgeon or healthcare facility for use with relevant bone(s) of the patient. To do so, the surgical plan system may be configured to determine relevant aspects of the patient's bone or bony anatomy from the medical images. For example, the surgical plan system may determine one or more mechanical axis of the relevant bones, determine one or more resection planes of the relevant bones, locate particular features of the relevant bones, and/or the like. Based on such determinations, the surgical plan system may select an appropriate orthopaedic implant type and size that also satisfies the implant constraint data of the surgical plan request. The surgical plan system may also be configured to determine recommended range of sizes of the orthopaedic implant. For example, in some embodiments, the surgical plan system may be configured to determine an orthopaedic implant within a range of plus or minus two sizes. For example, the surgical plan system may recommend an orthopaedic implant of a size 5+/−2 sizes (i.e., a range of size 3 to size 7). In creating the surgical plan, the surgical plan system may also retrieve a digital template(s) of the orthopaedic implant. The digital template may be retrieved from, for example, the memory device 48, mass storage device 49 or from any other storage location capable of storing a number of digital templates. The digital template may include one or more two-dimensional and/or three-dimensional electronic renderings of the orthopaedic implant selected for the surgical procedure, or components thereof, that is capable of being superimposed on a medical image of the patient. For example, a digital template may be embodied as a two-dimensional or three-dimensional electronic rendering of an orthopaedic knee implant component that is capable of being superimposed or otherwise incorporated into a medical image of a tibia or femur bone of the patient. As discussed in more detail below, the digital template may be used in conjunction with indicia of the determined aspects or features of the relevant bones such as lines or other indicia of the mechanical axis or resection points/planes of the relevant bones.

The surgical plan system may superimpose or otherwise incorporate the digital template into the medical images of the surgical plan request. For example, in one illustrative embodiment, as illustrated in FIG. 18B, a digital template 3300 of an orthopaedic implant is superimposed on a medical image 3302 of a bone of the patient. As discussed above, although the illustrative digital template 3300 is illustrated as a two-dimensional template, in other embodiments, the digital template may include any number of two-dimensional and/or three-dimensional electronic renderings of the orthopaedic implant.

The surgical plan system may be configured to use any suitable algorithm and data of the surgical plan request to determine a recommended location and orientation of the orthopaedic implant, as represented by the digital template, with respect to the patient's bone. For example, if implant constraint data provides an estimated amount of resection of the patients' bone, the surgical plan system may be configured to position the digital template in the medical images based on such estimated resection. In addition, any one or more of the aspects of the bone as determined above may be used to determine the proper positioning of the digital template. For example, the determined mechanical axis, resection planes, and/or other determined aspects of the relevant bones may be used to determine the proper positioning of the digital template. In this way, the surgical plan system generates a number of digital template medical images having indicia of the relevant bone's of the patient and indicia of the recommended orthopaedic implant positioned in a location and orientation.

In one embodiment, the implant is hyaluronic acid (HA). The HA is naturally found in the synovial fluid found between bones and acts as a lubricant. Current treatments like Hyalgan require weekly injections for three to five weeks. Pain relief is not experienced until a few weeks into the treatment. Even though the pain relief is not quick, it is longer lasting than other pain treatments like corticosteroids, which are fast acting but provide short relief Using a "Visual Analogue Scale and Western Ontario McMaster Universities Osteoarthritis Index score", knees treated with the multiply cross-linked HA can benefit from decreased pain and increased movement as long as two years. Procedure for injections includes:
    Knee area is cleaned
    If area is swollen because of excess fluid in joint, a needle will be used to drain fluid after a local anesthetic is applied
    With drainage system in place, multiply cross-linked HA is injected into knee joint
    The same needle may be used for drainage and injections or two different syringes
The system can be used for augmenting information to a doctor during implantation of HA into the knee as follows:
    obtaining injection location from sensors (such as X-rays, MRI, and CT-Scans);
    determining, from the 3D kinematic data, scores characterizing a joint function of the patient, the scores being relative to one or more and comparing the scores to data in a database which characterize a plurality of treatment plans and/or surgery plans to generate the list of one or more joint treatment plans and/or surgery plans which match the scores.
    System identifies best injection points and displays the point using augmented reality to guide the doctor to inject HA at the right points on the knee.

In another embodiment, the system looks up surgical plan sequence:
    determines body landmarks or key positions,
    identifies or highlights on the HUD each surgical path to surgically operate and provides instructions on surgical techniques,
    optionally overlaying images of the anatomy to guide the doctor
    wait until each surgical technique and then show next technique until done
    accessing the target component to replace or repair and show instructions to repair or replace,
    sequentially showing instructions to seal body portions previously opened or removed.

While knee implant is discussed above, other implants can be used. For example, a surgeon holds a wireless wand-like device near a place where he plans to make an incision, the device sends data about that spot to a computer where it is combined with information from a CT scan of the patient's brain taken previously. This information is compiled into a single X-ray-like image that the surgeon can see in real time with VR/AR displays, allowing her to examine the blood vessels and nerves that surround the place of the incision so that the surgical tool is as precise as possible. Once the incision is made, the AR/VR display can help the surgeon damage as little as possible on its way to the desired nerve, where the surgeon can implant the neuromodulator device.

Embodiments of the present technology are thus described. While the present technology has been described in particular examples, it should be appreciated that the present technology should not be construed as limited by such examples, but rather construed according to the claims.

Embodiments for virtually placing an object in a piece of content can be summarized as follows:

What is claimed is: (EYE BASED HEART MONITORING)

1. A monitoring system for a person, comprising:
a projector aimed at a retina, the projector providing 3D images with different depth view points,
the projector having a camera to capture retinal vascularization;
a processor coupled to the camera to detect blood vessel pulses; and
a wireless transceiver coupled to the transceiver to communicate with a remote processor.

2. The system of claim 1, comprising a gyroscope coupled to the projector.

3. The system of claim 1, comprising a sound transducer coupled to the wireless transceiver to communicate audio.

4. The system of claim 1, comprising one of: EEG detector, EKG detector, ECG detector, electromagnetic detector, ultrasonic detector, optical detector.

5. The system of claim 1, comprising an accelerometer to monitor patient movement.

6. The system of claim 1, wherein the electrodes are mounted on a back of a skin-contacting case.

7. The system of claim 1, comprising a call center to provide a human response.

8. The system of claim 1, comprising a web server coupled to the wireless network and to the POTS to provide information to an authorized remote user.

9. The system of claim 1, wherein the sensor monitors blood pressure.

10. The system of claim 1, wherein the sensor monitors EEG to identify a seizure.

11. The system of claim 1, comprising code to display heart waveforms on a mobile device.

12. The system of claim 1, wherein the sensor determines one of: total body water, compartmentalization of body fluids, cardiac monitoring, blood flow, skinfold thickness, dehydration, blood loss, wound monitoring, ulcer detection, deep vein thrombosis, hypovolemia, hemorrhage, blood loss.

13. The system of claim 1, comprising a patch having a bioelectric impedance (BI) sensor in communication with the wireless transceiver.

14. The system of claim 1, wherein the transceiver transmits and receives voice from the person over a wireless network to one of: a doctor, a nurse, a medical assistant, a caregiver, an emergency response unit, a family member.

15. The system of claim 1, comprising code to store and analyze patient information.

16. The system of claim 15, wherein the patient information includes medicine taking habits, eating and drinking habits, sleeping habits, or exercise habits.

17. The system of claim 1, comprising a patch having one or more sensors in communication with the wireless mesh network.

18. The system of claim 1, wherein the sensor monitors glucose level.

19. A monitoring system, comprising:
a projector aimed at a retina, the projector providing 3D images with different depth view points; a mobile device;
a sensor including one or more electrodes mounted on a case to contact a patient, the sensor having a wireless transceiver adapted to communicate with the mobile device; and a software module to display vital signs on the mobile device.

20. The system of claim 19, comprising code for sensing eye health, code for emotion sensing, or code for authenticating access to a secured device based on retinal blood vessel dilation.

What is claimed is: (EYE BASED BLOOD PRESSURE MONITORING)

1. A monitoring system for a person, comprising:
a projector aimed at a retina, the projector providing 3D images with different depth view points, the projector having a camera to capture retinal vascularization;
a processor coupled to the camera to detect blood vessel pulses, the processor generating a blood pressure based on the blood vessel pulses; and
a wireless transceiver coupled to the transceiver to communicate with a remote processor.

2. The system of claim 1, comprising code to calibrate the blood pressure with an external blood pressure instrument.

3. The system of claim 1, comprising a sound transducer coupled to the wireless transceiver to communicate audio.

4. The system of claim 1, comprising one of: EEG detector, EKG detector, ECG detector, electromagnetic detector, ultrasonic detector, optical detector.

5. The system of claim 4, comprising an accelerometer to monitor patient movement.

6. The system of claim 4, comprising electrodes are mounted on aback of a skin-contacting case.

7. The system of claim 1, comprising a call center to provide a human response.

8. The system of claim 1, comprising a web server coupled to the wireless network and to the POTS to provide information to an authorized remote user.

9. The system of claim 1, wherein the sensor monitors blood pressure.

10. The system of claim 1, wherein the sensor monitors EEG to identify a seizure.

11. The system of claim 1, comprising code to display heart waveforms on a mobile device.

12. The system of claim 1, wherein the sensor determines one of: total body water, compartmentalization of body fluids, cardiac monitoring, blood flow, skinfold thickness, dehydration, blood loss, wound monitoring, ulcer detection, deep vein thrombosis, hypovolemia, hemorrhage, blood loss.

13. The system of claim 1, comprising a patch having a bioelectric impedance (BI) sensor in communication with the wireless transceiver.

14. The system of claim 1, wherein the transceiver transmits and receives voice from the person over a wireless network to one of: a doctor, a nurse, a medical assistant, a caregiver, an emergency response unit, a family member.

15. The system of claim 1, comprising code to store and analyze patient information.

16. The system of claim 15, wherein the patient information includes medicine taking habits, eating and drinking habits, sleeping habits, or exercise habits.

17. The system of claim 1, comprising a patch having one or more sensors in communication with the wireless mesh network.

18. The system of claim 1, wherein the sensor monitors glucose level.

19. A monitoring system, comprising:
a projector aimed at a retina, the projector providing 3D images with different depth view points;
a mobile device;
a sensor including one or more electrodes mounted on a case to contact a patient, the sensor having a wireless transceiver adapted to communicate with the mobile device; and
a software module to display vital signs on the mobile device.

20. The system of claim 19, comprising code for sensing eye health, code for emotion sensing, or code for authenticating access to a secured device based on retinal blood vessel dilation.

What is claimed is: (EYE BASED MEDICAL MONITORING)

1. A monitoring system for a person, comprising:
a laser projector mounted on a lens and aimed at a retina, the projector providing 3D images with different depth view points;
a glucose sensor mounted on the lens;
a processor coupled to the projector and sensor; and
a wireless transceiver coupled to the transceiver to communicate with a remote processor.

2. The system of claim 1, comprising a camera mounted on the lens and aimed at the retina.

3. The system of claim 1, comprising a sound transducer coupled to the wireless transceiver to communicate audio.

4. The system of claim 1, comprising one of: EEG detector, EKG detector, ECG detector, electromagnetic detector, ultrasonic detector, optical detector.

5. The system of claim 1, comprising an accelerometer to monitor patient movement.

6. The system of claim 1, wherein the electrodes are mounted on a back of a skin-contacting case.

7. The system of claim 1, comprising a call center to provide a human response.

8. The system of claim 1, comprising a web server coupled to the wireless network and to the POTS to provide information to an authorized remote user.

9. The system of claim 1, wherein the sensor monitors blood pressure.

10. The system of claim 1, wherein the sensor monitors EEG to identify a seizure.

11. The system of claim 1, comprising code to display heart waveforms on a mobile device.

12. The system of claim 1, wherein the sensor determines one of: total body water, compartmentalization of body fluids, cardiac monitoring, blood flow, skinfold thickness, dehydration, blood loss, wound monitoring, ulcer detection, deep vein thrombosis, hypovolemia, hemorrhage, blood loss.

13. The system of claim 1, comprising a patch having a bioelectric impedance (BI) sensor in communication with the wireless transceiver.

14. The system of claim 1, wherein the transceiver transmits and receives voice from the person over a wireless network to one of: a doctor, a nurse, a medical assistant, a caregiver, an emergency response unit, a family member.

15. The system of claim 1, comprising code to store and analyze patient information.

16. The system of claim 15, wherein the patient information includes medicine taking habits, eating and drinking habits, sleeping habits, or exercise habits.

17. The system of claim 1, wherein the sensor monitors glucose level.

18. A monitoring system, comprising:
a projector aimed at a retina, the projector providing 3D images with different depth view points; a mobile device;
a sensor including one or more electrodes mounted on a case to contact a patient, the sensor having a wireless transceiver adapted to communicate with the mobile device; and
a software module to display vital signs on the mobile device.

19. The system of claim 18, comprising a glucose sensor.

20. The system of claim 18, comprising code for sensing eye health, code for emotion sensing, or code for authenticating access to a secured device based on retinal blood vessel dilation.

What is claimed is: (EYE BASED MEDICAL MONITORING)

1. A monitoring system for a person, comprising:
a laser projector mounted on a lens and aimed at a retina, the projector providing 3D images with different depth view points;
a piezoelectric transducer on the lens emitting a signal to image retinal vascularization; a glucose sensor mounted on the lens;
a processor coupled to the projector and sensor; and
a wireless transceiver coupled to the transceiver to communicate with a remote processor.

2. The system of claim 1, comprising a transducer mounted on the lens and aimed at the retina.

3. The system of claim 1, comprising a sound transducer coupled to the wireless transceiver to communicate audio.

4. The system of claim 1, comprising one of: EEG detector, EKG detector, ECG detector, electromagnetic detector, ultrasonic detector, optical detector.

5. The system of claim 1, comprising an accelerometer to monitor patient movement.

6. The system of claim 1, wherein the electrodes are mounted on a back of a skin-contacting case.

7. The system of claim 1, comprising a call center to provide a human response.

8. The system of claim 1, comprising a web server coupled to the wireless network and to the POTS to provide information to an authorized remote user.

9. The system of claim 1, wherein the sensor monitors blood pressure.

10. The system of claim 1, wherein the sensor monitors EEG to identify a seizure.

11. The system of claim 1, comprising code to display heart waveforms on a mobile device.

12. The system of claim 1, wherein the sensor determines one of: total body water, compartmentalization of body fluids, cardiac monitoring, blood flow, skinfold thickness, dehydration, blood loss, wound monitoring, ulcer detection, deep vein thrombosis, hypovolemia, hemorrhage, blood loss.

13. The system of claim 1, comprising a patch having a bioelectric impedance (BI) sensor in communication with the wireless transceiver.

14. The system of claim 1, wherein the transceiver transmits and receives voice from the person over a wireless network to one of: a doctor, a nurse, a medical assistant, a caregiver, an emergency response unit, a family member.

15. The system of claim 1, comprising code to store and analyze patient information.

16. The system of claim 15, wherein the patient information includes medicine taking habits, eating and drinking habits, sleeping habits, or exercise habits.

17. The system of claim 1, wherein the sensor monitors glucose level.

18. A monitoring system, comprising:
a projector aimed at a retina, the projector providing 3D images with different depth view points; a piezoelectric transducer on the lens emitting a signal to image retinal vascularization; a mobile device;
a sensor including one or more electrodes mounted on a case to contact a patient, the sensor having a wireless transceiver adapted to communicate with the mobile device; and
a software module to display data on the mobile device.

19. The system of claim 18, comprising a glucose sensor.

20. The system of claim 18, comprising code for sensing eye health, code for emotion sensing, or code for authenticating access to a secured device based on retinal blood vessel dilation.

What is claimed is: (CONTACT LENS-BIONIC EYE)

1. A monitoring system for a person, comprising:
a laser projector mounted on a lens and aimed at a retina, the projector providing 3D images with different depth view points;
a piezoelectric transducer to focus the lens;
a processor coupled to the projector and tranducer to autofocus the lens; and
a wireless transceiver coupled to the transceiver to communicate with a remote processor.

2. The system of claim 1, comprising a transducer mounted on the lens and aimed at the retina to image retinal vascularization.

3. The system of claim 1, comprising a sound transducer coupled to the wireless transceiver to communicate audio.

4. The system of claim 1, comprising one of: EEG detector, EKG detector, ECG detector, electromagnetic detector, ultrasonic detector, optical detector.

5. The system of claim 1, comprising an accelerometer to monitor patient movement.

6. The system of claim 1, wherein the electrodes are mounted on a back of a skin-contacting case.

7. The system of claim 1, comprising a call center to provide a human response.

8. The system of claim 1, comprising a web server coupled to the wireless network and to the POTS to provide information to an authorized remote user.

9. The system of claim 1, comprising a sensor that monitors blood pressure.

10. The system of claim 1, comprising a sensor that monitors EEG to identify a seizure.

11. The system of claim 1, comprising code to display heart waveforms on a mobile device.

12. The system of claim 1, comprising a sensor that determines one of: total body water, compartmentalization of body fluids, cardiac monitoring, blood flow, skinfold thickness, dehydration, blood loss, wound monitoring, ulcer detection, deep vein thrombosis, hypovolemia, hemorrhage, blood loss.

13. The system of claim 1, comprising a patch having a bioelectric impedance (BI) sensor in communication with the wireless transceiver.

14. The system of claim 1, wherein the transceiver transmits and receives voice from the person over a wireless network to one of: a doctor, a nurse, a medical assistant, a caregiver, an emergency response unit, a family member.

15. The system of claim 1, comprising code to zoom and view a distant object.

16. The system of claim 15, wherein the patient information includes medicine taking habits, eating and drinking habits, sleeping habits, or exercise habits.

17. The system of claim 1, wherein the sensor monitors glucose level.

18. A monitoring system, comprising:
a projector aimed at a retina, the projector providing 3D images with different depth view points;
a piezoelectric transducer to focus the lens;
a processor coupled to the projector and tranducer to autofocus the lens; and
a sensor including one or more electrodes mounted on a case to contact a patient, the sensor having a wireless transceiver adapted to communicate with a mobile device 19. The system of claim 18, comprising a glucose sensor on the lens.

20. The system of claim 18, comprising code to zoom the lens and view a distant object.

What is claimed is: (BLINDESS COMPENSATION)

1. A vision system for a person, comprising:
a projector aimed at a retina, the projector providing 3D images with different depth view points; a camera to capture vision and transmitting the vision to the projector to paint the retina with images associated with the vision.

2. The system of claim 1, comprising a gyroscope coupled to the projector.

3. The system of claim 1, comprising a sound transducer coupled to the wireless transceiver to communicate audio.

4. The system of claim 1, comprising one of EEG detector, EKG detector, ECG detector, electromagnetic detector, ultrasonic detector, optical detector.

5. The system of claim 1, comprising an accelerometer to monitor patient movement.

6. The system of claim 1, wherein the electrodes are mounted on a back of a skin-contacting case.

7. The system of claim 1, comprising a call center to provide a human response.

8. The system of claim 1, comprising a web server coupled to the wireless network and to the POTS to provide information to an authorized remote user.

9. The system of claim 1, wherein the sensor monitors blood pressure.

10. The system of claim 1, wherein the sensor monitors EEG to identify a seizure.

11. The system of claim 1, comprising code to display heart waveforms on a mobile device.

12. The system of claim 1, wherein the sensor determines one of: total body water, compartmentalization of body fluids, cardiac monitoring, blood flow, skinfold thickness, dehydration, blood loss, wound monitoring, ulcer detection, deep vein thrombosis, hypovolemia, hemorrhage, blood loss.

13. The system of claim 1, comprising a patch having a bioelectric impedance (BI) sensor in communication with the wireless transceiver.

14. The system of claim 1, wherein the transceiver transmits and receives voice from the person over the mesh network to one of a doctor, a nurse, a medical assistant, a caregiver, an emergency response unit, a family member.

15. The system of claim 1, comprising code to store and analyze patient information.

16. The system of claim 15, wherein the patient information includes medicine taking habits, eating and drinking habits, sleeping habits, or exercise habits.

17. The system of claim 1, comprising a patch having one or more sensors in communication with a wireless network.

18. The system of claim 1, wherein the sensor monitors glucose level.

19. A monitoring system, comprising:
a projector aimed at a retina, the projector providing 3D images with different depth view points; a camera to capture vision and transmitting the vision to the projector to paint the retina with images associated with the vision;
a mobile device coupled to the projector;
a sensor including one or more electrodes mounted on a case to contact a patient, the sensor having a wireless transceiver adapted to communicate with the mobile device; and
a software module to display information from the mobile device and the camera using the projector.

20. The system of claim 19, wherein the electrodes are mounted on a back of a case to contact the patient's body.

What is claimed is: (WEIGHT MONITORING)

1. A food intake monitoring system for a person, comprising:
a camera to capture an image of a food item;
a processor coupled to the camera to recognize the food item and determine calorie therefrom; and
a projector aimed at a retina, the projector providing 3D images with calorie information and recommendations.

2. The system of claim 1, comprising one or more computer implemented agents each specializing in a health condition, each agent communicating with another computer implemented agent, the client or the treatment professional, wherein at least one computer implemented agent sends an instruction promoting healthy client behavior to the projector.

3. The system of claim 1, comprising computer readable code to:
collect information on the client; and
select a treatment template based on treatment plan for people with similar characteristics to the client.

4. The system of claim 1, comprising code to automatically collect calorie intake of the food as consumed and detecting calorie count based on consumed food.

5. The system of claim 4, comprising code to automatically identify volume and content of the item.

6. The system of claim 3, comprising code to automatically determine if the item is part of a recommended nutritional guideline and to render on the projector alternatives that replace or supplement the item to at least meet the recommended nutritional guideline.

7. The system of claim 1, comprising code to model patient movements and convert the patient movements into energy consumption.

8. The system of claim 1, comprising code to model calorie usage from exercises and adapt client diet in response to client exercises.

9. The system of claim 1, comprising code to accumulate reward points for the client to encourage healthy activities.

10. The system of claim 1, comprising code to compare client progress with progress for people with a similar health condition to the client and send normative messages to improve client progress.

11. The system of claim 1, comprising a sound transducer coupled to the processor to communicate audio.

12. The system of claim 1, comprising multimedia code to generate an experience of extreme, disturbing, or unexpected fear, stress, or pain, and that involves or threatens serious injury, perceived serious injury, or death to the person or someone else.

13. The system of claim 1, comprising multimedia code to stimulate release of adrenaline and to noradrenaline from the medulla of the adrenal glands.

14. The system of claim 1, comprising multimedia code to stimulate release of catecholamines at neuroreceptor sites.

15. The system of claim 1, comprising code to stimulate neuron firings in a locus ceruleus.

16. The system of claim 1, comprising multimedia code to stimulate release of adrenaline and to noradrenaline from the medulla of the adrenal glands.

17. The system of claim 1, comprising multimedia code to activate a sympathetic nervous system and release of norepinephrine from nerve endings acting on a heart, blood vessels, respiratory center.

18. The system of claim 1, comprising multimedia code to activate a hypothalamic-pituitary-adrenal axis.

19. The system of claim 1, comprising a sensor coupled to the processor to provide data to the projector and code that determines one of: total body water, compartmentalization of body fluids, cardiac monitoring, blood flow, skinfold thickness, dehydration, blood loss, wound monitoring, ulcer detection, deep vein thrombosis, hypovolemia, hemorrhage, blood loss.

20. The system of claim 1, comprising a patch having one or more sensors in communication with a wireless network.

What is claimed is: (DATING)

1. A dating system, comprising:
a first camera to capture an image of a dating prospect and a second camera to capture eye gazing;
a processor coupled to the second camera to determine interest in the dating prospect, the processor coupled to the first camera to analyze prospect information including appearance and body shape therefrom, the processor comparing the interest and prospect information with prior likings; and
a projector aimed at a retina, the projector providing information and recommendations on approaching the dating prospect.

2. The system of claim 1, wherein the processor looks up interests based on social network and professional network postings.

3. The system of claim 1, comprising computer readable code to:
collect information on the dating prospect; and recommend a conversation starter template based on people with similar characteristics.

4. The system of claim 1, comprising code to determine favorite activities of the dating prospects and formulate a dating plan with the activities.

5. The system of claim 4, comprising code to recommend activities to maximize cost and benefits based on the interest and prospect information.

6. The system of claim 5, comprising code to automatically determine if the activity includes dining and providing a recommended nutritional guideline.

7. The system of claim 1, comprising code to model activity movements and convert the movements into energy consumption.

8. The system of claim 1, comprising code to model calorie usage from dating activities and adapt restaurant recommendations in response to the calorie usage.

9. The system of claim 1, comprising code to accumulate reward points to encourage healthy activities.

10. The system of claim 1, comprising code to compare dating progress with progress for people with a similar interests and send normative messages on activities to improve dating progress.

11. The system of claim 1, comprising a sound transducer coupled to the processor to communicate audio.

12. The system of claim 1, comprising multimedia code to generate an experience of extreme, disturbing, or unexpected fear, stress, or pain, and that involves or threatens serious injury, perceived serious injury, or death to the person or someone else.

13. The system of claim 1, comprising multimedia code to stimulate release of adrenaline and to noradrenaline from the medulla of the adrenal glands.

14. The system of claim 1, comprising multimedia code to stimulate release of catecholamines at neuroreceptor sites.

15. The system of claim 1, comprising code to stimulate neuron firings in a locus ceruleus.

16. The system of claim 1, comprising multimedia code to stimulate release of adrenaline and to noradrenaline from the medulla of the adrenal glands.

17. The system of claim 1, comprising multimedia code to activate a sympathetic nervous system and release of norepinephrine from nerve endings acting on a heart, blood vessels, respiratory center.

18. The system of claim 1, comprising multimedia code to activate a hypothalamic-pituitary-adrenal axis.

What is claimed is: PAIN MANAGEMENT

1. A system to treat a person, comprising:
a treatment processor determining a pain experienced by the person at a selected time;
a head-mounted device to be worn by a person; and
a content generator driving the head-mounted device to keep the person busy most of the time and to distract the person with a loud noise or a distracting video at a selected time.

2. The system of claim 1, wherein the head-mounted device comprises an augmented reality device or a virtual reality device.

3. The system of claim 1, wherein the content generator comprises a game or a video.

4. The system of claim 1, wherein the content generator displays content to cause a rush in the person.

5. The system of claim 1, wherein the content generator displays content to cause biological generation of adrenaline in the person.

6. The system of claim 1, comprising sensors to detect pain or discomfort.

7. The system of claim 6, wherein one of the sensors comprises biofeedback sensor, electromyogram (EMG) sensors, electroencephalography (EEG), electrophysiological sensor, electrocorticography (ECoG) sensor, magnetoencephalography (MEG) sensor, positron emission tomography (PET) sensor, functional magnetic resonance imaging (fMRI) sensor, optical imaging sensor, functional Near InfraRed (fNIR) sensor.

8. The system of claim 1, wherein the person is distract at a pain portion of an operation, a treatment, a biological sampling, an irradiation process, or a body scan.

9. The system of claim 1, comprising:
positioning the patient in a targeted area for a medical mission;
sensing biometric and physical conditions of a patient during the mission, and
keeping the patient in a predetermined position with a game or video during medical mission.

10. The system of claim 1, comprising sharing images of a procedure from a healthcare provider with the patient.

11. The system of claim 1, wherein the sensing comprises tracking motion or capturing biofeedback data.

12. The system of claim 1, wherein the sensor determines one of: total body water, compartmentalization of body fluids, cardiac monitoring, blood flow, skinfold thickness, dehydration, blood loss, wound monitoring, ulcer detection, deep vein thrombosis, hypovolemia, hemorrhage, blood loss.

13. The system of claim 1, comprising code to perform gesture recognition, facial recognition and voice recognition.

14. The system of claim 1, comprising a 3-D body sensor, wherein the treatment processor compares a patient position to a reference position, and providing feedback to a patient to move to the reference position.

15. The system of claim 1, comprising a game that mentally shocks the person at the selected time.

16. The system of claim 1, wherein the game provides a virtual world with an avatar for the person, wherein the avatar moves based on the person's head movement.

17. A system for monitoring a patient, comprising:
sensors to detect pain based on biometric and physical conditions of a patient; and
a multimedia wearable device to provide a mental shock blocking pain when the sensors detect a pain condition for the patient.

18. The system of claim 17, comprising a projector aimed at a retina, the projector providing 3D images with different depth view points.

19. A monitoring system, comprising:
a projector aimed at a retina, the projector providing 3D images with different depth view points;
a camera to capture vision and transmitting the vision to the projector to paint the retina with images associated with the vision;
a mobile device coupled to the projector;
sensors coupled to a body to detect pain based on biometric and physical conditions, the sensor having a wireless transceiver adapted to communicate with the mobile device; and
a software module to display information from the mobile device and the camera using the projector to provide mental stimulation during pain episodes to distract the patient from feeling the pain.

20. The system of claim 19, wherein the software module displays content to cause biological generation of adrenaline in a person.

Being Still for Medical/Dental Operation to Avoid Sedation

1. A system, comprising:
a head-mounted device to be worn by a person;
a content generator driving the head-mounted device to engage the person to keep the person still in a predetermined position with a visualization for the patient and
sensors to detect a body position of the person and if the person have moved the body position, the sensors notify the content generator to encourage the person to move back into the predetermined position.

2. The system of claim 1, wherein the head-mounted device comprises an augmented reality device or a virtual reality device.

3. The system of claim 1, wherein the content generator comprises a game or a video.

4. The system of claim 1, comprising a transducer to stimulate pleasure for the person when the body is in the predetermined position.

5. The system of claim 1, wherein the content generator displays content to cause biological generation of adrenaline in the person.

6. The system of claim 1, comprising sensors to detect pain or discomfort.

7. The system of claim 6, wherein one of the sensors comprises biofeedback sensor, electromyogram (EMG) sensors, electroencephalography (EEG), electrophysiological sensor, electrocorticography (ECoG) sensor, magnetoencephalography (MEG) sensor, positron emission tomography (PET) sensor, functional magnetic resonance imaging (fMRI) sensor, optical imaging sensor, functional Near InfraRed (fNIR) sensor.

8. The system of claim 1, wherein the person is distract at a pain portion of an operation, a treatment, a biological sampling, an irradiation process, or a body scan.

9. The system of claim 1, comprising:
positioning the patient in a targeted area for a medical mission;
sensing biometric and physical conditions of a patient during the mission, and
keeping the patient in a predetermined position with a game or video during medical mission.

10. The system of claim 1, comprising sharing images of a procedure from a healthcare provider with the patient.

11. The system of claim 1, wherein the sensing comprises tracking motion or capturing biofeedback data.

12. The system of claim 1, wherein the sensor determines one of: total body water, compartmentalization of body fluids, cardiac monitoring, blood flow, skinfold thickness, dehydration, blood loss, wound monitoring, ulcer detection, deep vein thrombosis, hypovolemia, hemorrhage, blood loss.

13. The system of claim 1, comprising code to perform gesture recognition, facial recognition and voice recognition.

14. The system of claim 1, comprising a 3-D body sensor, wherein the treatment processor compares a patient position to a reference position, and providing feedback to a patient to move to the reference position.

15. The system of claim 1, comprising a game that mentally shocks the person at the selected time.

16. The system of claim 1, wherein the game provides a virtual world with an avatar for the person, wherein the avatar moves based on the person's head movement.

17. A system for monitoring a patient, comprising:
a frame with a target position for the patient in a medical mission;
sensors to detect patient movement away from the target position; and
a multimedia wearable device to drive the patient to restore the target position.

18. The system of claim 17, comprising a projector aimed at a retina, the projector providing 3D images with different depth viewpoints.

19. A monitoring system, comprising:
a projector aimed at a retina, the projector providing 3D images with different depth view points; a camera to capture vision and transmitting the vision to the projector to paint the retina with images associated with the vision;
a mobile device coupled to the projector;
sensors coupled to a body to detect pain based on biometric and physical conditions, the sensor having a wireless transceiver adapted to communicate with the mobile device; and
a software module to display information from the mobile device and the camera using the projector to provide mental stimulation during pain episodes to distract the patient from feeling the pain.

20. The system of claim 19, wherein the software module displays content to cause biological generation of adrenaline in a person.

3D Kinematics and Image Fusion Surgical Visualization System

1. A method for treating a patient, comprising:
wearing a head-mounted device during surgery;
accessing patient medical data from one or more medical scanning devices;
capturing patient movement data;
fusing the medical data and movement data and driving the head-mounted device to provide surgical instructions customized to the patient.

2. The method of claim 1, wherein the head-mounted device comprises an augmented reality device or a virtual reality device.

3. The method of claim 1, comprising generating a list of one or more joint treatment plans and/or surgery plans for a joint of a patient.

4. The method of claim 1, comprising: obtaining 3D kinematic data of the joint in movement; characterizing a joint function and applying the function to a plurality of treatment plans and/or surgery plans to identify one or more joint treatment plans and/or surgery plans for the patient.

5. The method of claim 1, comprising simulating the one or more joint treatment plans and/or surgery plans using the 3D kinematic data to produce a plurality of modified 3D kinematic data and rendering the simulated images on the head-mounted device.

6. The method of claim 5, further comprising comparing the plurality of modified 3D kinematic data to kinematic data for a healthy joint model to optimize one or more treatment plans and/or surgery plans for the patient.

7. The method of claim 5, comprising applying a pattern recognition technique on the modified 3D kinematic data, the pattern recognition technique comprising one of a parametric or non-parametric technique, a hidden Markov model (HMM) network, a neural network, a nearest neighbor classification technique, a projection technique, a decision tree technique, a stochastic method, a genetic algorithms and an unsupervised learning and clustering technique.

8. The method of claim 7, wherein the comparing further comprises classifying the modified 3D kinematic data of the joint of the patient, to which were applied the pattern recognition technique, in one of several classes of known knee joint treatment plan and/or surgery plan.

9. The method of claim 1, wherein the obtaining 3D kinematic data from a 3D kinematic sensor comprises obtaining 3D kinematic data from at least one of a camera, an accelerometer, an electromagnetic sensor, a gyroscope, an optical sensor.

10. The method of claim 1, further comprising: obtaining, from a 3D static imagery sensor, 3D static imagery data of the joint in a static position; merging the 3D kinematic data and the 3D static imagery data of the joint, to produce merged 3D joint data for the joint of the patient; and using the 3D joint data to produce and display a 3D animation of the joint.

11. The method of claim 1, further comprising simulating the one or more joint treatment plans and/or surgery plans using the 3D joint data to produce a plurality of modified 3D joint data.

12. The method of claim 4, further comprising calibrating the 3D joint data for a healthy joint model to adapt to measurements of the patient and thereby produce calibrated 3D joint data for use as 3D joint data for comparison to the plurality of modified 3D joint data.

13. The method of claim 12, further comprising recalibrating the 3D joint data for a healthy joint model to adapt to measurements of the patient and thereby produce recalibrated 3D joint data for use as the 3D joint data for comparison to the plurality of modified 3D joint data.

14. The method of claim 12, wherein the recalibrating comprises performing one of a dot by dot technique and a regionalization technique.

15. The method of claim 3, wherein the joint comprises one of a knee, a shoulder, a wrist, an ankle, an elbow and a hip.

16. The method of claim 3, comprising: obtaining, from motion sensors, 3D kinematic data of the joint in movement; obtaining, from a 3D static imagery sensor, 3D static imagery data of the joint in a static position; merging the 3D kinematic data and the 3D static imagery data of the joint, to produce merged 3D joint data for the joint of the patient; and using the 3D joint data to produce and display a 3D animation of the joint.

17. The method of claim 16, further comprising simulating the one or more joint treatment plans and/or surgery plans using the 3D joint data to produce a plurality of modified 3D joint data.

18. The method of claim 16, further comprising comparing the plurality of modified 3D joint data to joint data for a healthy joint model to determine which one from the list of one or more joint treatment plans and/or surgery plans will produce optimal results for the patient.

19. The method of claim 16, wherein the obtaining 3D static imagery data from a static imagery sensor comprises obtaining 3D static imagery data from a radiological examination device comprising one of an X-ray machine, a Magnetic Resonance Imaging machine and a CT scanning machine.

20. A method for treating a knee, comprising:
mapping injection location(s) from one or more sensors (such as X-rays, MRI, and CT-Scans);
determining, from 3D kinematic data, scores characterizing a joint function of the patient, the scores being relative to one or more and comparing the scores to data in a database which characterize a plurality of treatment plans and/or surgery plans to generate the list of one or more joint treatment plans and/or surgery plans which match the scores.

identifying best injection points and displaying the point using augmented reality to guide the doctor to inject HA at selected points on the knee.

Doctor Scribe

1. A method to capture consultation between a professional and a patient, comprising:
   wearing a head-mounted device on the professional; and
   augmenting performance of a healthcare provider during a patient meeting by rendering custom medical data on the patient and supplemented by communications from multi-disciplinary group of professionals to serve the patient.

2. The system of claim 1, wherein the head-mounted device comprises an augmented reality device or a virtual reality device.

3. The system of claim 1, comprising accepting patient-related data captured during the patient meeting for transmission to said remote site, at least one element for transmitting the captured patient data and at least one element for presenting patient-related data transmitted from said remote site.

4. The method of claim 1, comprising selecting and opening a pre-completed note based on patient's chief complaint and automatically importing vital signs, laboratory results, nursing notes from current patient encounter into note.

5. The method of claim 1, comprising storing a multimedia recording of a current encounter and using machine translation and human review, documenting date and time of patient arrival or initiation of current encounter; documenting date and time patient seen by physician; documenting physician's name; documenting scribe's name; documenting resident physician's name, if applicable; documenting physician assistant's name, if applicable; documenting primary care physician's name, if applicable; documenting specialist physician's name, if applicable; documenting historical medication list or import medication profile from current encounter; documenting historical allergy list or import allergy profile from current encounter; documenting history source(s) for current encounter; documenting arrival mode of patient for current encounter; and importing or cutting and pasting nursing triage narrative into freetext field of note.

6. The method of claim 5, comprising documenting or importing active problem list from current encounter; documenting or importing past medical history; documenting or importing past surgical history; documenting or importing family history; documenting or importing social history; and scribe saving of document.

7. The method of claim 5, comprising saving a problem list from most recent hospital admission history and physical examination, if available; importing patient's problem list, active problem list control, or patient's active problem list profile from current encounter.

8. The method of claim 5, comprising documenting patient's family history based on patient's patient medical history questionnaire responses; saving family history from most recent hospital admission history and physical examination, if available; importing patient's family history control or patient's family history profile from current encounter.

9. The method of claim 1, comprising documenting patient's past surgical history based on patient's patient medical history questionnaire responses; cutting and pasting past surgical history from most recent hospital admission history and physical examination, if available; importing patient's past surgical history control or patient's past surgical history profile from current encounter.

10. The method of claim 1, comprising documenting or importing social history from the patient.

11. The method of claim 10, comprising documenting patient's social history based on patient's patient medical history questionnaire responses; cutting and pasting social history from most recent hospital admission history and physical examination, if available; importing patient's social history control or patient's family history profile from current encounter.

12. The method of claim 1, comprising: documenting history and physical examination or progress note of patient through the end of the physical examination portion of patient documentation; scribe saving of document 6. The method of claim 1, comprising 13. The method of claim 1, comprising generating: a graphical representation of status of a single task or series of tasks related to an event; a graphical sequence of symbolic representations of status of the patient meeting or a linear sequence of graphical representations of status of patient encounter or patient encounter documentation status.

14. The method of claim 1, comprising documenting patient's past medical history based on patient's patient medical history questionnaire responses; cutting and pasting past medical history from most recent hospital admission history and physical examination, if available; importing patient's past medical history control or patient's past medical history profile from current encounter.

15. The method of claim 1, comprising documenting results of tests, exams, and treatments for said patient encounter comprising: documenting lab results when becoming available for said patient encounter; documenting radiology report results when becoming available for said current patient encounter; completing tasks associated with all events represented in the scribe task column on patient tracking board; documenting any additional physician activities completed in relation to care of said patient during said encounter; scribe saving of document;

16. The method of claim 1, comprising capturing a predetermined set of electrocardiogram data elements and physician interpretation by appropriate pre-completed electrocardiogram basic physician interpretation macro based on whether an old electrocardiogram is available or not, and whether there is a change from old electrocardiogram or not; documenting date and time of electrocardiogram; documenting electrocardiogram rate; documenting electrocardiogram PR interval; documenting electrocardiogram QRS duration time interval; documenting electrocardiogram QTc interval; documenting those electrocardiogram computer rhythm interpretations, or portions thereof, noted for inclusion by physician by way of checking, circling, or underlining on paper electrocardiogram; not documenting those electrocardiogram computer rhythm interpretations, or portions thereof, not noted for inclusion by physician by way of checking, circling, or underlining on paper electrocardiogram; not documenting those electrocardiogram computer rhythm interpretations, or portions thereof, noted for exclusion by physician by way of single line strike-through on paper electrocardiogram; documenting any additional physician electrocardiogram interpretations as noted in writing by physician on paper electrocardiogram; documenting interpretation completed by physician; indicating scribe completion of physician electrocardiogram interpretation documentation in the electronic medical record by way of initialing the upper right corner of the paper electrocardiogram; and completing the scribe electrocardiogram documentation event;

17. The method of claim 1, comprising capturing an addendum note for said patient and inserting a procedure note template based on information obtained from the physician.

Doctor Treatment Plan Info Fusion

1. A method for dispensing medication to a patient, comprising:
   wearing a display providing an augmented reality view;
   identifying the patient by sensing eye fixation on the patient;
   displaying patient medical issue and overlaying patient history or financials on the augmented reality view of the machine in a mashed-up and aligned manner; and providing an audio or visual link to another professional during a consultation with the patient using the augmented reality view.

2. The method of claim 1, comprising generating the augmented reality view from a laser scan, a video or other imaging mechanism.

3. The method of claim 1, wherein display of the augmented reality view and user interaction therewith are implemented by an augmented reality application; and the database is one of external to or embedded in the augmented reality application.

4. The method of claim 1, comprising scanning and analyzing a composition of the patient.

5. The method of claim 1, comprising applying medical knowledge with patient and other professionals 6. The method of claim 1, comprising searching, retrieving drug information and providing literature to a doctor to perform critical evaluation of the drug information and automatically checking and recommending low cost alternatives for the prescribed drug.

7. The method of claim 1, comprising providing at least one augmented reality interface including one or more of the following: a visual interface, an audio interface, a voice recognition interface, and a localization interface.

8. The method of claim 1, comprising generating at least one augmented reality data stream comprises one or more of the following: data related to a composition of a plurality of medication; data related to a location of a plurality of medication on a plurality of sorting surfaces; data related to the at least one bin to receive at least one of the plurality of medication; and data related to an identity of an augmented reality interface user that separates the at least one of the plurality of sortable medications from the remainder of the plurality of sortable medications.

9. The method of claim 1, comprising generating one or more of the following: an audible instruction to the at least one augmented reality interface user; a readable text superimposed on a field of view of the at least one augmented reality interface user; and at least one visual indicium superimposed on the field of view of the at least one augmented reality interface user.

10. The method of claim 1, comprising tracking a location of the plurality of pill on at least one surface.

11. The method of claim 1, comprising automatically recommending a generic replacement or substitute for the pill.

12. The method of claim 11, comprising displaying instructions on fabricating a target pill using chemical ingredients available at a predetermined location including instructions on clean room practices.

13. The method of claim 1, comprising displaying vital sign history, hospital medical data, out-patient data or in-office medical data during a consultation.

14. The method of claim 1, comprising analyzing effects of behavior change and recommending the best change during a consultation.

15. The method of claim 1, comprising transmitting a consultation history to a remote station, wherein relevant parts of the consultation are saved or streamed, and updates to an EHR are entered for provider confirmation after the patient encounter.

16. A method for surgical data augmentation, comprising:
   obtaining, from sensors, medical imaging of a patient and determining body landmarks or key positions and aligning data from different imaging modalities;
   scoring the patient and comparing a score to data in a database which characterize a plurality of treatment plans and/or surgery plans to generate the list of one or more treatment plans and/or surgery plans matching the score.
   displaying on the augmented view each surgical path to surgically operate and provides instructions on surgical techniques,
   iteratively displaying instructions and tracking performance of the surgical techniques to access a target body component to replace or repair, and
   sequentially showing instructions to finalize the surgery.

17. The method of claim 16, comprising capturing images from X-rays, MRI, or CT-Scans.

18. The method of claim 16, comprising overlaying images of the anatomy and medical images.

Pharmacist Info Fusion

1. A method for dispensing medication to a patient, comprising:
   wearing a display providing an augmented reality view;
   detecting interest in a drug by sensing eye fixation on the drug or hand interaction with the drug;
   in response to user interaction with the drug, searching a drug interaction database and displaying pharmacology data on the drug;
   overlaying patient history or financials on the augmented reality view of the machine in a mashed-up and aligned manner; and providing an audio or visual link to another professional during a consultation with the patient using the augmented reality view.

2. The method of claim 1, comprising generating the augmented reality view from a laser scan, a video or other imaging mechanism.

3. The method of claim 1, wherein display of the augmented reality view and user interaction therewith are implemented by an augmented reality application; and the database is one of external to or embedded in the augmented reality application.

4. The method of claim 1, comprising recognizing pills on a surface using computer vision.

5. The method of claim 1, wherein the pills are placed on a belt for pharmacy review.

6. The method of claim 1, comprising applying medical knowledge with patient and other professionals.

7. The method of claim 1, comprising searching, retrieving drug information and providing literature to the pharmacist to perform critical evaluation of the drug information.

8. The method of claim 1, comprising automatically checking and recommending low cost alternatives for the prescribed drug.

9. The method of claim 1, comprising scanning and analyzing a composition of a pill.

10. The method of claim 1, comprising providing at least one augmented reality interface including one or more of the following: a visual interface, an audio interface, a voice recognition interface, and a localization interface.

11. The method of claim 1, comprising generating at least one augmented reality data stream comprises one or more of the following: data related to a composition of a plurality of medication; data related to a location of a plurality of medication on a plurality of sorting surfaces; data related to the at least one bin to receive at least one of the plurality of medication; and data related to an identity of an augmented reality interface user that separates the at least one of the plurality of sortable medications from the remainder of the plurality of sortable medications.

12. The method of claim 1, comprising generating one or more of the following: an audible instruction to the at least one augmented reality interface user; a readable text superimposed on a field of view of the at least one augmented reality interface user; and at least one visual indicium superimposed on the field of view of the at least one augmented reality interface user.

13. The method of claim 1, comprising tracking a location of the plurality of pill on at least one surface.

14. The method of claim 1, comprising automatically recommending a generic replacement or substitute for the pill.

15. The method of claim 14, comprising displaying instructions on fabricating a target pill using chemical ingredients available at a predetermined location including instructions on clean room practices.

17. The method of claim 1, comprising displaying vital sign history of the patient during a consultation.

18. The method of claim 1, comprising displaying hospital medical data, out-patient data or in-office medical data during a consultation.

19. The method of claim 1, comprising analyzing effects of behavior change and recommending the best change during a consultation.

20. The method of claim 1, comprising rendering data directly on a retina with a laser.

AR for Facility Design and Repair

1. A computer aided design (CAD) modeling method comprising:
generating an augmented reality view of a facility, the facility having various objects displayed in the augmented reality view;
in response to user interaction with one of the facility objects as displayed in the augmented reality view, searching a CAD database for a corresponding CAD model of the one object, the CAD database storing a CAD model of the facility from a CAD modeling system, said searching resulting in obtaining the CAD model of the facility that contains the corresponding CAD model of the one object;
displaying a CAD model view of the one facility object overlaying on the augmented reality view of the one facility object in a mashed-up and aligned manner such that the CAD model view is displayed contemporaneously and contiguously to the augmented reality view; and
enabling user interaction with the displayed CAD model view to update the CAD model of the facility in the CAD modeling system.

2. The method of claim 1 wherein the facility is a building, plant, factory, refinery, city, entity or other asset.

3. The method of claim 1 comprising generating the augmented reality view from a laser scan, a video or other imaging mechanism.

4. The method of claim 1 wherein display of the augmented reality view and user interaction therewith are implemented by an augmented reality application; and the CAD database is one of external to or embedded in the augmented reality application.

5. The method of claim 4 further comprising the step of federating the CAD modeling system with the augmented reality application.

6. The method of claim 1 wherein the step of enabling user interaction with the displayed CAD model view is implemented by the CAD modeling system that was originally used to generate the CAD model of the facility and/or used to store said CAD model in the CAD database.

7. The method of claim 1 comprising in response to user interaction with the displayed CAD model view, the CAD modeling system updating the corresponding CAD model of the object and the CAD model of the facility in the CAD database.

8. The method of claim 1 wherein displaying of the CAD model view of the one facility object overlaying the augmented reality view is aligned in size, dimensions and/or orientation.

9. The method of claim 1, comprising:
identifying buildings and building structures positioned thereon; and retrieving a building repair sequence.

10. The method of claim 1, comprising:
determining type and location of a building structure, and
highlighting on the augmented reality view each building structure to be opened or removed and provides instructions on opening or removal techniques.

11. The method of claim 11, comprising
iteratively providing instructions to allow each structure to be opened or removed and then show next structure;
accessing a target structure to replace or repair and showing instructions to repair or replace; and
showing instructions in sequence to put back structures previously opened or removed.

13. The method of claim 1, wherein the facility comprises a vehicle, a car, a plane, a ship.

14. The method of claim 13, comprising rendering in the augmented view maintenance or repair techniques.

AR for Industrial Equipment Repair

1. A method for building, maintaining or repairing a machine, comprising:
generating an augmented reality view of the machine, the machine having various automatically detected objects displayed in the augmented reality view;
in response to user interaction with one of the objects in the machine as displayed in the augmented reality view, searching a CAD database for a corresponding CAD model of the one object, the CAD database storing a CAD model of the machine from a CAD modeling system, said searching resulting in obtaining the CAD model of the machine that contains the corresponding CAD model of the one object;
displaying a CAD model view of the object overlaying on the augmented reality view of the machine in a mashed-up and aligned manner such that the CAD model view is displayed contemporaneously and contiguously to the augmented reality view; and identifying in the augmented reality view each object to be opened or removed and providing instructions on how to open or move the object in order to access a targeted object.

2. The method of claim 1, comprising enabling user interaction with the displayed CAD model view to update the CAD model of the facility in the CAD modeling system.

3. The method of claim 1, comprising generating the augmented reality view from a laser scan, a video or other imaging mechanism.

4. The method of claim 1, wherein display of the augmented reality view and user interaction therewith are implemented by an augmented reality application; and the CAD database is one of external to or embedded in the augmented reality application.

5. The method of claim 1, comprising recognizing objects on a surface and instructing a user to select a sequence of objects to build an assembly.

6. The method of claim 1, wherein the objects are on a conveyor belt.

7. The method of claim 1, comprising automatically identifying the machine and retrieving parts and components in the machine.

8. The method of claim 1, comprising
after each component is opened or removed, detecting the next object to be opened or removed to reach the targeted object to be replaced or repaired;
showing instructions to repair or replace the object; and
showing instructions in the augmented reality view to put back objects previously opened or removed.

9. The method of claim 1, comprising scanning and analyzing a composition of one object.

10. The method of claim 1, comprising providing at least one augmented reality interface including one or more of the following: a visual interface, an audio interface, a voice recognition interface, and a localization interface.

11. The method of claim 1, comprising generating at least one augmented reality data stream comprises one or more of the following: data related to a composition of a plurality of sortable items; data related to a location of a plurality of sortable items on a plurality of sorting surfaces; data related to the at least one bin to receive at least one of the plurality of sortable items; and data related to an identity of an augmented reality interface user that separates the at least one of the plurality of sortable items from the remainder of the plurality of sortable items 12. The method of claim 1, comprising generating one or more of the following: an audible instruction to the at least one augmented reality interface user; a readable text superimposed on a field of view of the at least one augmented reality interface user; and at least one visual indicium superimposed on the field of view of the at least one augmented reality interface user.

13. The method of claim 1, comprising tracking a location of the plurality of object on at least one surface.

14. The method of claim 1, comprising automatically recommending a replacement or substitute for the object if a spare object is not available.

15. The method of claim 14, comprising displaying instructions on alternate ways to reconstruct the target object using parts available at a predetermined location.

What is claimed is: (AR/R WITH GESTURE RECOGNITION)

1. A method for rendering augmented reality content, the method comprising the steps of
capturing images of an instant surrounding within a field of view of an image capturing device;
generating virtual images by accessing content from a multimedia server;
rendering virtual content by integrating the virtual images retrieved from the multimedia server with the images captured by the image capturing device, wherein the content depicts scenes from the instant surrounding;
displaying the virtual content to a user; and
rendering gesture input, wherein an outcome of the gesture input is applied to the displayed virtual content to alter details of the displayed virtual content.

2. The method of claim 1, wherein the virtual images of objects are generated by simulating content from the multimedia server based on selection made by the user.

3. The method of claim 1, wherein virtual content is rendered based on direction of projection of light into the eye of the user, wherein the movement of the eye and the change in eye position at various instants are constantly monitored.

4. The method of claim 3, wherein the virtual content is displayed based on determination of the direction of projection of light into the user's eye.

5. The method of claim 1, wherein the virtual content is rendered by determining intensity of light to be projected into the user's eyes, such that, the content is clearly visible to the user.

6. The method of claim 5, wherein the virtual content is displayed based on the intensity of light to be projected into the user's eyes.

7. The method of claim 1, wherein one or more details in the displayed virtual content are possible to be altered or modified by rendering one or more gesture input received from the user.

8. The method of claim 1, wherein the outcomes of the gesture input are rendered to the virtual content displayed to the user, to alter or modify one or more details in the virtual content.

9. The method of claim 1, wherein the virtual content is displayed in one or more formats such as two or three-dimensional formats based on field of view and depth of field of the user's eye and the image capturing device, wherein the field of view and depth of field of the user's eye is detected from the user's eye position.

10. The method of claim 1, wherein a display surface and a format of display is selected relative to the user's position and orientation.

Computing devices such as the foregoing generally each include instructions executable by one or more computing devices such as those listed above. Computer-executable instructions may be compiled or interpreted from computer programs created using a variety of programming languages and/or technologies known to those skilled in the art, including, without limitation, and either alone or in combination, Java™, C, C++, Visual Basic, Java Script, Python, Perl, etc. In general, a processor (e.g., a microprocessor) receives instructions, e.g., from a memory, a computer-readable medium, etc., and executes these instructions, thereby performing one or more processes, including one or more of the processes described herein. Such instructions and other data may be stored and transmitted using a variety of known computer-readable media.

A computer-readable medium includes any medium that participates in providing data (e.g., instructions), which may be read by a computer. Such a medium may take many forms, including, but not limited to, non-volatile media, volatile media, and transmission media. Non-volatile media include, for example, optical or magnetic disks and other persistent memory. Volatile media include dynamic random access memory (DRAM), which typically constitutes a main memory. Transmission media include coaxial cables, copper wire and fiber optics, including the wires that comprise a system bus coupled to the processor. Transmission media may include or convey acoustic waves, light waves and electromagnetic emissions, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, Blu-Ray, any other optical medium, punch cards, paper tape, any other physical medium with patterns of holes, a RAM, a PROM, an EPROM, a FLASH-EEPROM, any other memory chip or cartridge, a carrier wave as described hereinafter, or any other medium from which a computer can read.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claimed invention.

Accordingly, it is to be understood that the above description is intended to be illustrative and not restrictive. Many embodiments and applications other than the examples provided would be apparent to those of skill in the art upon reading the above description. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future embodiments. In sum, it should be understood that the invention is capable of modification and variation and is limited only by the following claims.

All terms used in the claims are intended to be given their broadest reasonable constructions and their ordinary meanings as understood by those skilled in the art unless an explicit indication to the contrary in made herein. In particular, use of the singular articles such as "a," "the," "said," etc. should be read to recite one or more of the indicated elements unless a claim recites an explicit limitation to the contrary.

What is claimed is:

1. A system, comprising:
   a first camera to capture an image of a dating prospect and a second camera to capture eye gazing;
   a processor coupled to the second camera to determine interest in the dating prospect, the processor coupled to the first camera to analyze prospect information including appearance and body shape therefrom, the processor comparing the interest and prospect information with prior likings; and
   a projector aimed at a retina, the projector providing information and recommendations on approaching the dating prospect.

2. The system of claim 1, wherein the processor looks up interests based on social network and professional network postings.

3. The system of claim 1, comprising computer readable code to:
   collect information on the dating prospect; and
   recommend a conversation starter template based on people with similar characteristics.

4. The system of claim 1, comprising code to determine favorite activities of the dating prospects and formulate a dating plan with the activities.

5. The system of claim 4, comprising code to recommend activities to maximize cost and benefits based on the interest and prospect information.

6. The system of claim 5, comprising code to automatically determine if the activity includes dining and providing a recommended nutritional guideline.

7. The system of claim 1, comprising code to model activity movements and convert the movements into energy consumption.

8. The system of claim 1, comprising code to model calorie usage from dating activities and adapt restaurant recommendations in response to the calorie usage.

9. The system of claim 1, comprising code to accumulate reward points to encourage healthy activities.

10. The system of claim 1, comprising code to compare dating progress with progress for people with a similar interests and send normative messages on activities to improve dating progress.

11. The system of claim 1, comprising a sound transducer coupled to the processor to communicate audio.

12. The system of claim 1, comprising multimedia code to generate an experience of extreme, disturbing, or unexpected fear, stress, or pain, and that involves or threatens serious injury, perceived serious injury, or death to the person or someone else.

13. The system of claim 1, comprising multimedia code to stimulate release of adrenaline and to noradrenaline from the medulla of the adrenal glands, release of catecholamines at neuroreceptor sites, neuron firings in a locus ceruleus, release of adrenaline and to noradrenaline from the medulla of the adrenal glands, activation of a sympathetic nervous system and release of norepinephrine from nerve endings acting on a heart, blood vessels, respiratory center, or activation of a hypothalamic-pituitary-adrenal axis.

14. The system of claim 1, comprising:
   an eye tracking module to detect a sound region of interest;
   one or more microphone arrays coupled to the eye tracking module and focused on the detected sound region of interest; and
   one or more amplifiers wirelessly coupled to the one or more microphone arrays and to render sound from the sound region of interest for one or more ears.

15. A system, comprising:
   an eye tracking module to detect a sound region of interest;
   a first camera to capture an image of a dating prospect and a second camera to capture eye gazing;
   a processor coupled to the second camera to determine interest in the dating prospect, the processor coupled to the first camera to analyze prospect information including appearance and body shape therefrom, the processor comparing the interest and prospect information with prior likings; and
   one or more microphone arrays coupled to the eye tracking module and focused on the detected sound region of interest; and
   one or more amplifiers wirelessly coupled to the one or more microphone arrays and to render sound from the sound region of interest for one or more ears.

16. The system of claim 15, comprising external sensors to detect user action including temperature, gesture, hand command for use in a virtual reality or augmented reality application.

17. The system of claim 15, wherein the eye tracking module comprises one or more cameras to detect eye movement or eye gaze.

18. The system of claim 15, comprising an emotion detection module coupled to the eye tracking module.

19. The hearing system of claim 15, comprising a plurality of remote microphones positioned around a room.

20. The system of claim 15, comprising a beam forming module to capture sound from the microphone array and the remote microphones and deliver enhanced sound from the region of interest to the left and right ears.

* * * * *